(12) United States Patent
Jackson et al.

(10) Patent No.: US 9,402,775 B2
(45) Date of Patent: Aug. 2, 2016

(54) SINGLE AND DUAL COLUMN PATIENT POSITIONING AND SUPPORT STRUCTURE

(71) Applicant: Roger P. Jackson, Prairie Village, KS (US)

(72) Inventors: Roger P. Jackson, Prairie Village, KS (US); Lawrence E. Guerra, Mission, KS (US); Trevor A. Waggoner, Kansas City, KS (US)

(73) Assignee: Roger P. Jackson, Prairie Village, KS (US)

( * ) Notice: Subject to any disclaimer, the term of this patent is extended or adjusted under 35 U.S.C. 154(b) by 0 days.

(21) Appl. No.: 14/793,359

(22) Filed: Jul. 7, 2015

(65) Prior Publication Data

US 2016/0000627 A1 Jan. 7, 2016

Related U.S. Application Data

(60) Provisional application No. 62/021,481, filed on Jul. 7, 2014, provisional application No. 62/021,630, filed on Jul. 7, 2014, provisional application No. 62/021,643, filed on Jul. 7, 2014, provisional application No. 62/021,595, filed on Jul. 7, 2014, provisional application No. 62/118,305, filed on Feb. 19, 2015.

(51) Int. Cl.
*A61G 13/04* (2006.01)
*A61G 13/10* (2006.01)
(Continued)

(52) U.S. Cl.
CPC .............. *A61G 13/04* (2013.01); *A61B 6/0407* (2013.01); *A61G 13/06* (2013.01); *A61G 13/105* (2013.01)

(58) Field of Classification Search
CPC ........ A61B 5/704; A61B 6/40; A61B 6/0407; A61B 6/0457; A61G 7/002; A61G 7/005; A61G 7/008; A61G 7/012; A61G 7/015; A61G 7/018; A61G 13/00; A61G 13/02; A61G 13/04; A61G 13/06; A61G 13/08; A61G 13/104; A61G 13/105
See application file for complete search history.

(56) References Cited

U.S. PATENT DOCUMENTS

| 377,377 A | 2/1888 | Ferry |
|---|---|---|
| 1,046,430 A | 12/1912 | Beitz |

(Continued)

FOREIGN PATENT DOCUMENTS

| CN | 2467091 Y | 12/2001 |
|---|---|---|
| EP | 2226010 B1 | 6/2014 |

(Continued)

OTHER PUBLICATIONS

Brochure of Smith & Nephew on Spinal Positioning System, 2003, 2004.

(Continued)

*Primary Examiner* — Nicholas Polito
(74) *Attorney, Agent, or Firm* — Polsinelli PC

(57) ABSTRACT

A surgical table for supporting a patient over a floor and including a base assembly, a support column assembly and a patient support structure. The base assembly supported on the floor and including a first end, a second end opposite the first end, and a member extending along a base longitudinal axis between the first and second ends. The support column assembly moveably coupled with the base assembly and configured to translate between the first and second ends of the base assembly along the member extending therebetween, the support column assembly being the only support column assembly coupled with the base assembly. The patient support structure including a first end, a second end opposite the first end, and a longitudinal axis extending between the first and second ends, the second end of the patient support structure supported off of the support column assembly in a cantilevered fashion.

17 Claims, 79 Drawing Sheets

(51) Int. Cl.
    *A61G 13/06*      (2006.01)
    *A61B 6/04*       (2006.01)

(56)              References Cited

U.S. PATENT DOCUMENTS

| | | |
|---|---|---|
| 1,098,477 A | 6/1914 | Cashman |
| 1,160,451 A | 11/1915 | Sanford |
| 1,171,713 A | 2/1916 | Gilkerson |
| 1,482,439 A | 2/1924 | McCullough |
| 1,528,835 A | 3/1925 | McCullough |
| 1,667,982 A | 5/1928 | Pearson |
| 1,780,399 A | 11/1930 | Munson |
| 1,799,692 A | 4/1931 | Knott |
| 1,938,006 A | 12/1933 | Blanchard |
| 1,990,357 A | 2/1935 | Ward |
| 2,188,592 A | 1/1940 | Hosken et al. |
| 2,261,297 A | 11/1941 | Seib |
| 2,475,003 A | 7/1949 | Black |
| 2,636,793 A | 4/1953 | Meyer |
| 2,688,410 A | 9/1954 | Nelson |
| 2,792,945 A | 5/1957 | Brenny |
| 3,046,071 A | 7/1962 | Shampaine et al. |
| 3,049,726 A | 8/1962 | Getz |
| 3,281,141 A | 10/1966 | Smiley et al. |
| 3,584,321 A | 6/1971 | Buchanan |
| 3,599,964 A | 8/1971 | Magni |
| 3,766,384 A | 10/1973 | Anderson |
| 3,814,414 A | 6/1974 | Chapa |
| 3,832,742 A | 9/1974 | Stryker |
| 3,988,790 A | 11/1976 | Mracek et al. |
| 4,101,120 A | 7/1978 | Seshima |
| 4,131,802 A | 12/1978 | Braden et al. |
| 4,144,880 A | 3/1979 | Daniels |
| 4,148,472 A | 4/1979 | Rais et al. |
| 4,175,550 A | 11/1979 | Leininger et al. |
| 4,186,917 A | 2/1980 | Rais et al. |
| 4,227,269 A | 10/1980 | Johnston |
| 4,230,100 A | 10/1980 | Moon |
| 4,244,358 A | 1/1981 | Pyers |
| 4,391,438 A | 7/1983 | Heffington, Jr. |
| 4,435,861 A | 3/1984 | Lindley |
| 4,474,364 A | 10/1984 | Brendgord |
| 4,503,844 A | 3/1985 | Siczek |
| 4,552,346 A | 11/1985 | Schnelle et al. |
| 4,712,781 A | 12/1987 | Watanabe |
| 4,718,077 A | 1/1988 | Moore et al. |
| 4,763,643 A | 8/1988 | Vrzalik |
| 4,771,785 A | 9/1988 | Duer |
| 4,862,529 A | 9/1989 | Peck |
| 4,872,656 A | 10/1989 | Brendgord et al. |
| 4,872,657 A | 10/1989 | Lussi |
| 4,887,325 A | 12/1989 | Tesch |
| 4,937,901 A | 7/1990 | Brennan |
| 4,944,500 A | 7/1990 | Mueller et al. |
| 4,953,245 A | 9/1990 | Jung |
| 4,970,737 A | 11/1990 | Sagel |
| 4,989,848 A | 2/1991 | Monroe |
| 5,013,018 A * | 5/1991 | Sicek ............... A61B 6/0457 378/209 |
| 5,088,706 A | 2/1992 | Jackson |
| 5,131,103 A | 7/1992 | Thomas et al. |
| 5,131,105 A | 7/1992 | Harrawood et al. |
| 5,131,106 A | 7/1992 | Jackson |
| 5,161,267 A | 11/1992 | Smith |
| 5,163,890 A | 11/1992 | Perry, Jr. |
| 5,181,289 A | 1/1993 | Kassai |
| 5,208,928 A | 5/1993 | Kuck et al. |
| 5,210,887 A | 5/1993 | Kershaw |
| 5,210,888 A | 5/1993 | Canfield |
| 5,230,112 A | 7/1993 | Harrawood et al. |
| 5,231,741 A | 8/1993 | Maguire |
| 5,239,716 A | 8/1993 | Fisk |
| 5,274,862 A | 1/1994 | Palmer, Jr. |
| 5,333,334 A | 8/1994 | Kassai |
| 5,393,018 A | 2/1995 | Roth et al. |
| 5,444,882 A | 8/1995 | Andrews et al. |
| 5,461,740 A | 10/1995 | Pearson |
| 5,468,216 A | 11/1995 | Johnson et al. |
| 5,487,195 A | 1/1996 | Ray |
| 5,499,408 A | 3/1996 | Nix |
| 5,524,304 A | 6/1996 | Shutes |
| 5,544,371 A | 8/1996 | Fuller |
| 5,579,550 A | 12/1996 | Bathrick et al. |
| 5,588,705 A | 12/1996 | Chang |
| 5,613,254 A | 3/1997 | Clayman et al. |
| 5,640,730 A | 6/1997 | Godette |
| 5,645,079 A | 7/1997 | Zahiri et al. |
| 5,658,315 A | 8/1997 | Lamb et al. |
| 5,659,909 A | 8/1997 | Pfeuffer et al. |
| 5,673,443 A | 10/1997 | Marmor |
| 5,737,781 A | 4/1998 | Votel |
| 5,754,997 A | 5/1998 | Lussi et al. |
| 5,774,914 A | 7/1998 | Johnson et al. |
| 5,794,286 A | 8/1998 | Scott et al. |
| 5,862,549 A | 1/1999 | Morton et al. |
| 5,870,784 A | 2/1999 | Elliott |
| 5,890,238 A | 4/1999 | Votel |
| 5,901,388 A | 5/1999 | Cowan |
| 5,937,456 A | 8/1999 | Norris |
| 5,996,151 A | 12/1999 | Bartow et al. |
| 6,000,076 A | 12/1999 | Webster et al. |
| 6,035,465 A | 3/2000 | Rogozinski |
| 6,049,923 A | 4/2000 | Ochiai |
| 6,212,713 B1 | 4/2001 | Kuck et al. |
| 6,260,220 B1 | 7/2001 | Lamb et al. |
| 6,282,736 B1 | 9/2001 | Hand et al. |
| 6,282,738 B1 | 9/2001 | Heimbrock et al. |
| 6,286,164 B1 | 9/2001 | Lamb et al. |
| 6,295,671 B1 | 10/2001 | Reesby et al. |
| 6,322,251 B1 | 11/2001 | Ballhaus et al. |
| 6,438,777 B1 | 8/2002 | Bender |
| 6,496,991 B1 | 12/2002 | Votel |
| 6,499,162 B1 | 12/2002 | Lu |
| 6,505,365 B1 | 1/2003 | Hanson et al. |
| 6,526,610 B1 | 3/2003 | Hand et al. |
| 6,634,043 B2 | 10/2003 | Lamb et al. |
| 6,638,299 B2 | 10/2003 | Cox |
| 6,662,388 B2 | 12/2003 | Friel |
| 6,668,396 B2 | 12/2003 | Wei |
| 6,681,423 B2 | 1/2004 | Zachrisson |
| 6,701,553 B1 | 3/2004 | Hand et al. |
| 6,854,137 B2 | 2/2005 | Johnson |
| 6,857,144 B1 | 2/2005 | Huang |
| 6,862,759 B2 | 3/2005 | Hand et al. |
| 6,885,165 B2 * | 4/2005 | Henley ............... A61B 6/0457 318/135 |
| 6,971,131 B2 | 12/2005 | Bannister |
| 6,971,997 B1 | 12/2005 | Ryan et al. |
| 7,003,828 B2 | 2/2006 | Roussy |
| 7,055,195 B2 | 6/2006 | Roussy |
| 7,089,612 B2 | 8/2006 | Rocher et al. |
| 7,103,931 B2 | 9/2006 | Somasundaram et al. |
| 7,137,160 B2 | 11/2006 | Hand et al. |
| 7,152,261 B2 | 12/2006 | Jackson |
| 7,171,709 B2 | 2/2007 | Weismiller |
| 7,189,214 B1 | 3/2007 | Saunders |
| 7,197,778 B2 | 4/2007 | Sharps |
| 7,213,279 B2 | 5/2007 | Weismiller et al. |
| 7,234,180 B2 | 6/2007 | Horton et al. |
| 7,290,302 B2 | 11/2007 | Sharps |
| 7,331,557 B2 | 2/2008 | Dewert |
| 7,343,635 B2 | 3/2008 | Jackson |
| 7,428,760 B2 | 9/2008 | McCrimmon |
| 7,552,490 B2 | 6/2009 | Saracen et al. |
| 7,565,708 B2 | 7/2009 | Jackson |
| 7,596,820 B2 | 10/2009 | Nielsen et al. |
| 7,653,953 B2 | 2/2010 | Lopez-Sansalvador |
| 7,669,262 B2 | 3/2010 | Skripps et al. |
| 7,739,762 B2 | 6/2010 | Lamb et al. |
| 7,874,695 B2 | 1/2011 | Jensen |
| 8,056,163 B2 | 11/2011 | Lemire et al. |
| 8,060,960 B2 | 11/2011 | Jackson |
| 8,381,331 B2 | 2/2013 | Sharps et al. |
| 8,584,281 B2 | 11/2013 | Diel et al. |

(56) References Cited

U.S. PATENT DOCUMENTS

| | | |
|---|---|---|
| 8,635,725 B2 | 1/2014 | Tannoury et al. |
| 8,677,529 B2 | 3/2014 | Jackson |
| 8,707,476 B2 | 4/2014 | Sharps |
| 8,707,484 B2 | 4/2014 | Jackson |
| 8,719,979 B2 | 5/2014 | Jackson |
| 8,826,474 B2 | 9/2014 | Jackson |
| 8,826,475 B2 | 9/2014 | Jackson |
| 8,839,471 B2 | 9/2014 | Jackson |
| 8,844,077 B2 | 9/2014 | Jackson et al. |
| 8,856,986 B2 | 10/2014 | Jackson |
| 8,938,826 B2 | 1/2015 | Jackson |
| 8,978,180 B2 | 3/2015 | Jackson |
| 9,180,062 B2 | 11/2015 | Jackson |
| 9,198,817 B2 | 12/2015 | Jackson |
| 9,205,013 B2 | 12/2015 | Jackson |
| 9,211,223 B2 | 12/2015 | Jackson |
| 2001/0037524 A1 | 11/2001 | Truwit |
| 2003/0074735 A1 | 4/2003 | Zachrisson |
| 2003/0145383 A1 | 8/2003 | Schwaegerle |
| 2004/0098804 A1 | 5/2004 | Varadharajulu et al. |
| 2004/0133983 A1 | 7/2004 | Newkirk et al. |
| 2004/0219002 A1 | 11/2004 | Lenaers |
| 2006/0248650 A1 | 11/2006 | Skripps |
| 2007/0056105 A1 | 3/2007 | Hyre et al. |
| 2007/0107126 A1 | 5/2007 | Koch et al. |
| 2008/0216241 A1 | 9/2008 | Mangiardi |
| 2010/0037397 A1 | 2/2010 | Wood |
| 2010/0107790 A1 | 5/2010 | Yamaguchi |
| 2010/0192300 A1 | 8/2010 | Tannoury et al. |
| 2011/0107516 A1* | 5/2011 | Jackson ................ A61G 13/04 5/608 |
| 2011/0107517 A1 | 5/2011 | Lamb et al. |
| 2012/0144589 A1 | 6/2012 | Skripps et al. |
| 2012/0174319 A1 | 7/2012 | Menkedick |
| 2012/0198625 A1 | 8/2012 | Jackson |
| 2012/0246829 A1 | 10/2012 | Lamb et al. |
| 2012/0246830 A1 | 10/2012 | Hornbach |
| 2013/0111666 A1 | 5/2013 | Jackson |
| 2013/0133137 A1 | 5/2013 | Jackson |
| 2013/0198958 A1 | 8/2013 | Jackson et al. |
| 2013/0219623 A1 | 8/2013 | Jackson |
| 2013/0254995 A1 | 10/2013 | Jackson |
| 2013/0254996 A1 | 10/2013 | Jackson |
| 2013/0269710 A1 | 10/2013 | Hight et al. |
| 2013/0282234 A1 | 10/2013 | Roberts et al. |
| 2013/0312181 A1 | 11/2013 | Jackson et al. |
| 2013/0312187 A1 | 11/2013 | Jackson |
| 2013/0312188 A1 | 11/2013 | Jackson |
| 2014/0007349 A1 | 1/2014 | Jackson |
| 2014/0020181 A1 | 1/2014 | Jackson |
| 2014/0033436 A1 | 2/2014 | Jackson |
| 2014/0068861 A1 | 3/2014 | Jackson et al. |
| 2014/0082842 A1 | 3/2014 | Jackson |
| 2014/0109316 A1 | 4/2014 | Jackson et al. |
| 2014/0173826 A1 | 6/2014 | Jackson |
| 2014/0196212 A1 | 7/2014 | Jackson |
| 2014/0201913 A1 | 7/2014 | Jackson |
| 2014/0201914 A1 | 7/2014 | Jackson |
| 2014/0208512 A1 | 7/2014 | Jackson |
| 2014/0317847 A1 | 10/2014 | Jackson |
| 2015/0007391 A1 | 1/2015 | Xu |
| 2015/0059094 A1 | 3/2015 | Jackson |
| 2015/0113733 A1 | 4/2015 | Diel et al. |
| 2015/0150743 A1 | 6/2015 | Jackson |
| 2016/0000620 A1 | 1/2016 | Koch |
| 2016/0000621 A1 | 1/2016 | Jackson et al. |
| 2016/0000626 A1 | 1/2016 | Jackson et al. |
| 2016/0000629 A1 | 1/2016 | Jackson et al. |
| 2016/0008201 A1 | 1/2016 | Jackson et al. |
| 2016/0038364 A1 | 2/2016 | Jackson |

FOREIGN PATENT DOCUMENTS

| | | |
|---|---|---|
| GB | 569758 | 6/1945 |
| GB | 810956 | 3/1959 |
| JP | S53763 | 1/1978 |
| JP | 2000-060995 | 2/2000 |
| JP | 2000-116733 | 4/2000 |
| WO | WO99/07320 | 2/1999 |
| WO | WO 00/07537 | 2/2000 |
| WO | WO00/62731 | 10/2000 |
| WO | WO01/60308 | 8/2001 |
| WO | WO 02/078589 A1 | 10/2002 |
| WO | WO03/070145 | 8/2003 |
| WO | WO 2007/130679 A2 | 11/2007 |
| WO | WO2009/054969 | 4/2009 |
| WO | WO2009/100692 | 8/2009 |
| WO | WO2010/051303 A1 | 5/2010 |

OTHER PUBLICATIONS

Complaint for Patent Infringement, *Jackson v. Mizuho Orthopedic Sys., Inc.*, No. 4:12-CV-01031 (W.D. Mo. Aug. 7, 2012).

First Amended Complaint for Patent Infringement and Correction of Inventorship, *Jackson v. Mizuho Orthopedic Sys., Inc.*, No. 4:12-CV-01031 (W.D. Mo. Sep. 21, 2012).

Defendant Mizuho Orthopedic Systems, Inc.'s Answer to First Amended Complaint and Counterclaims, *Jackson v. Mizuho Orthopedic Sys., Inc.*, No. 4:12-CV-01031 (W.D. Mo. Nov. 1, 2012).

Plaintiff Roger P. Jackson, MD's, Reply to Counterclaims, *Jackson v. Mizuho Orthopedic Sys., Inc.*, No. 4:12-CV-01031 (W.D. Mo. Nov. 26, 2012).

Roger P. Jackson's Disclosure of Asserted Claims and Preliminary Infringement Contentions, *Jackson v. Mizuho Orthopedic Sys., Inc.*, No. 4:12-CV-01031 (W.D. Mo. Jan. 4, 2013).

Second Amended Complaint for Patent Infringement, for Correction of Inventorship, for Breach of a Non-Disclosure and Confidentiality Agreement, and for Misappropriation of Dr. Jackson's Right of Publicity, *Jackson v. Mizuho Orthopedic Sys., Inc.*, No. 4:12-CV-01031 (W.D. Mo. Jan. 28, 2013).

Defendant Mizuho Orthopedic Systems, Inc.'s Answer to Second Amended Complaint and Counterclaims, *Jackson v. Mizuho Orthopedic Sys., Inc.*, No. 4:12-CV-01031 (W.D. Mo. Feb. 19, 2013).

Defendant Mizuho Osi's Invalidity Contentions Pursuant to the Parties' Joint Scheduling Order, *Jackson v. Mizuho Orthopedic Sys., Inc.*, No. 4:12-CV-01031 (W.D. Mo. Feb. 22, 2013).

Plaintiff Roger P. Jackson, MD's, Reply to Second Counterclaims, *Jackson v. Mizuho Orthopedic Sys., Inc.*, No. 4:12-CV-01031 (W.D. Mo. Mar. 12, 2013).

Roger P. Jackson, MD's Disclosure of Proposed Terms to Be Construed, *Jackson v. Mizuho Orthopedic Sys., Inc.*, No. 4:12-CV-01031 (W.D. Mo. Apr. 5, 2013).

Defendant Mizuho Orthopedic Systems, Inc.'s Disclosure of Proposed Terms and Claim Elements for Construction, *Jackson v. Mizuho Orthopedic Sys., Inc.*, No. 4:12-CV-01031 (W.D. Mo. Apr. 5, 2013).

Mizuho Orthopedic Systems, Inc.'s Disclosure of Proposed Claim Constructions and Extrinsic Evidence, *Jackson v. Mizuho Orthopedic Sys., Inc.*, No. 4:12-CV-01031 (W.D. Mo. May 13, 2013).

Plaintiff Roger P. Jackson, MD's Disclosure of Preliminary Proposed Claim Constructions, *Jackson v. Mizuho Orthopedic Sys., Inc.*, No. 4:12-CV-01031 (W.D. Mo. May 13, 2013).

Defendant Mizuho Osi's Amended Invalidity Contentions Pursuant to the Parties' Joint Scheduling Order, *Jackson v. Mizuho Orthopedic Sys., Inc.*, No. 4:12-CV-01031 (W.D. Mo. May 15, 2013).

Joint Claim Construction Chart and Joint Prehearing Statement, *Jackson v. Mizuho Orthopedic Sys., Inc.*, No. 4:12-CV-01031 (W.D. Mo. Jun. 7, 2013).

Defendant Mizuho Orthopedic Systems, Inc.'s Objections and Responses to Plaintiff's First Set of Interrogatories, *Jackson v. Mizuho Orthopedic Sys., Inc.*, No. 4:12-CV-01031 (W.D. Mo. Jun. 24, 2013).

Defendant Mizuho Orthopedic Systems, Inc.'s Opening Claim Construction Brief, *Jackson v. Mizuho Orthopedic Sys., Inc.*, No. 4:12-CV-01031 (W.D. Mo. Jul. 31, 2013).

(56) References Cited

OTHER PUBLICATIONS

Plaintiff Roger P. Jackson, MD's Opening Claim Construction Brief, *Jackson* v. *Mizuho Orthopedic Sys., Inc.*, No. 4:12-CV-01031 (W.D. Mo. Jul. 31, 2013).
Appendix A Amended Infringement Contentions Claim Chart for Mizuho's Axis System Compared to U.S. Pat. No. 7,565,708, *Jackson* v. *Mizuho Orthopedic Sys., Inc.*, No. 4:12-CV-01031 (W.D. Mo. Aug. 12, 2013).
Appendix B Amended Infringement Contentions Claim Chart for Mizuho's Axis System Compared to U.S. Pat. No. 8,060,960, *Jackson* v. *Mizuho Orthopedic Sys., Inc.*, No. 4:12-CV-01031 (W.D. Mo. Aug. 12, 2013).
Appendix C Amended Infringement Contentions Claim Chart for Mizuho's Proaxis System Compared to U.S. Pat. No. 7,565,708, *Jackson* v. *Mizuho Orthopedic Sys., Inc.*, No. 4:12-CV-01031 (W.D. Mo. Aug. 12, 2013).
Appendix D Amended Infringement Contentions Claim Chart for Mizuho's Proaxis System Compared to U.S. Pat. No. 8,060,960, *Jackson* v. *Mizuho Orthopedic Sys., Inc.*, No. 4:12-CV-01031 (W.D. Mo. Aug. 12, 2013).
Plaintiff Roger P. Jackson, MD's Responsive Claim Construction Brief, *Jackson* v. *Mizuho Orthopedic Sys., Inc.*, No. 4:12-CV-01031 (W.D. Mo. Aug. 16, 2013).
Defendant Mizuho Orthopedic Systems, Inc's Brief in Response to Plaintiff's Opening Claim Construction Brief, *Jackson* v. *Mizuho Orthopedic Sys., Inc.*, No. 4:12-CV-01031 (W.D. Mo. Aug. 16, 2013).
Plaintiff Roger P. Jackson, Md's Suggestions in Support of His Motion to Strike Exhibit a of Mizuho's Opening Claim Construction Brief, *Jackson* v. *Mizuho Orthopedic Sys., Inc.*, No. 4:12-CV-01031 (W.D. Mo. Aug. 16, 2013).
Defendant Mizuho Orthopedic Systems, Inc.'s Opposition to Plaintiff's Motion to Strike, *Jackson* v. *Mizuho Orthopedic Sys., Inc.*, No. 4:12-CV-01031 (W.D. Mo. Sep. 3, 2013).
Transcript of Claim Construction Hearing, *Jackson* v. *Mizuho Orthopedic Sys., Inc.*, No. 4:12-CV-01031 (W.D. Mo. Oct. 11, 2013).
Plaintiff Roger P. Jackson, MD's Claim Construction Presentation for U.S. District Judge Nanette K. Laughrey, *Jackson* v. *Mizuho Orthopedic Sys., Inc.*, No. 4:12-CV-01031 (W.D. Mo. Oct. 11, 2013).
Mizuho's Claim Construction Argument, *Jackson* v. *Mizuho Orthopedic Sys., Inc.*, No. 4:12-CV-01031 (W.D. Mo. Oct. 11, 2013).
Order, *Jackson* v. *Mizuho Orthopedic Sys., Inc.*, No. 4:12-CV-01031 (W.D. Mo. Apr. 4, 2014).
Brochure of OSI on Modular Table System 90D, pp. 1-15, date of first publication: Unknown.
Pages from website http://www.schaerermayfieldusa.com, pp. 1-5, date of first publication: Unknown.
European Search Report, EP11798501.0, dated Mar. 30, 2015.
Canadian Office Action, CA2803110, dated Mar. 5, 2015.
Chinese Office Action, CN 201180039162.0, dated Jan. 19, 2015.
Japanese Office Action, JP 2014-142074, dated Jun. 18, 2015.
Japanese Office Action, JP 2014-132463, dated Jun. 18, 2015.
Quayle Action, U.S. Appl. No. 14/792,216, dated Sep. 9, 2015.
Australian Patent Examination Report No. 2, AU2014200274, dated Oct. 9, 2015.
European Examination Report, EP11798501.0, dated Nov. 12, 2015.
Japanese Final Rejection (English version), JP 2014-142074, dated Dec. 6, 2015.
International Search Report and Written Opinion of the International Searching Authority, PCT/US2015/039400, dated Dec. 7, 2015, 13 pages.
Japanese Office Action, JP 2016-041088, dated Apr. 12, 2016.

\* cited by examiner

SINGLE AND DUAL COLUMN PATIENT POSITIONING AND SUPPORT STRUCTURE

CROSS-REFERENCE TO RELATED APPLICATIONS

The present application claims priority under 35 U.S.C. §119 to U.S. Provisional Patent Application No. 62/118,305, filed on Feb. 19, 2015, titled "SINGLE COLUMN PATIENT POSITIONING AND SUPPORT STRUCTURE", which is hereby incorporated by reference in its entirety into the present application.

The present application claims priority under 35 U.S.C. §119 to U.S. Provisional Patent Application No. 62/021,630, filed on Jul. 7, 2014, titled "SURGICAL TABLE WITH PATIENT SUPPORT HAVING FLEXIBLE INNER FRAME SUPPORTED ON RIGID OUTER FRAME", which is hereby incorporated by reference in its entirety into the present application.

The present application claims priority under 35 U.S.C. §119 to U.S. Provisional Patent Application No. 62/021,643, filed on Jul. 7, 2014, titled "SINGLE COLUMN PATIENT POSITIONING SUPPORT STRUCTURE", which is hereby incorporated by reference in its entirety into the present application.

The present application claims priority under 35 U.S.C. §119 to U.S. Provisional Patent Application No. 62/021,595, filed on Jul. 7, 2014, titled "PATIENT SUPPORT STRUCTURE WITH PIVOTING AND TRANSLATING HINGE", which is hereby incorporated by reference in its entirety into the present application.

The present application claims priority under 35 U.S.C. §119 to U.S. Provisional Patent Application No. 62/021,481, filed on Jul. 7, 2014, titled "RADIOLUCENT HINGE FOR A SURGICAL TABLE", which is hereby incorporated by reference in its entirety into the present application.

TECHNICAL FIELD

Aspects of the present disclosure relate to systems and methods for supporting a patient during examination and treatment, including medical procedures such as imaging and surgery, with and without navigation technologies, and more particularly a single column patient support structure with various positioning capabilities, including supporting and manipulating a patient in prone, supine, lateral-decubitus and seated positions.

BACKGROUND

From scalpels to surgical tables, surgeons rely on a multitude of specially designed tools and apparatuses to perform surgical procedures. In any number of procedures, the surgeon may need to position and, thereafter, manipulate a patient in various positions (e.g., supine, prone, lateral-decubitus, Trendelenburg, reverse Trendelenburg, roll) throughout the surgery in order to perform various steps of the procedure. Positioning the patient in the various positions may require the use of a specialized table or support structure that is uniquely designed to facilitate the required movements for the procedure. In addition to repositioning a patient during the procedure, certain procedures (e.g., spinal surgery) may require the patient to undergo medical imaging during the procedure. To facilitate the medical imaging, the surgeon or another medical professional may generate medical images of the patient while the patient is supported on the support structure. In the case of Computed Tomography Imaging ("CT"), the patient and a portion of the support structure may be positioned within a circular opening of a scanning machine for the generation of medical images and then removed to continue the procedure. In order to generate medical images of the patient without being obstructed by imaging of the support structure, the table must be constructed of radiolucent materials (e.g., carbon fiber, PEEK, polymers, among other materials). Additionally, the support structure must function to appropriately position the patient in the scanning machine (e.g., the "donut" of the machine, such as an O-arm). In addition to the various positioning and materials requirements on surgical support structures, laws and regulations may provide additional requirements for safely positioning patients during a surgical procedure.

In many surgical procedures, a patient is anesthetized for the procedure. Often, a patient's trachea is intubated (i.e., a tube is placed into the trachea to maintain an open airway) while the patient is under anesthesia. Conventionally, the tracheal tube is taped to the patient's face or otherwise to hold the tube in place for the duration of the procedure. As is the case with many surgical procedures (e.g., spinal surgery), the patient and, thus, the surgical table, must be positioned in different orientations (e.g., flexion, extension, Trendelenberg) for a particular portion of the surgical procedure. While articulating the surgical table to position or reposition the patient in flexion, for example, the table must be hinged or pivoted to facilitate bending along the patient's spine. To eliminate dragging of the patient's torso over the table and to facilitate smoother, simultaneous bending of the table and the patient's body, torso sliding platforms, "torso trolleys," or "trunk translators" were developed, wherein these devices can be actively driven. These devices are configured to slide the patient's torso along a portion of the surgical table to reduce or eliminate dragging of the torso that would otherwise occur during simultaneous bending of the table and the patient's body, as well as potentially harmful distraction and compression along the spine.

The use of sliding chest platforms, however, introduces additional challenges into the surgical environment, as well as bulk and complexity including, additional software programming. For example, translating the patient's torso along the surgical table means that the patient's head is also moved along the table. Thus, the tracheal tube and other anesthetic equipment, such as tubes and lines, are forced to be moved along the table with the patient's head and upper torso. These movements increase the chances that the tracheal tube will be dislodged from the patient's trachea causing dangerous and potentially life threatening conditions. Another potential hazard of translating a patient's head during articulating of the surgical table is that pressure points could be introduced on the patient's head and eyes that could cause lasting damage. For example, as the patient's head is translated along the surgical table, the patient's head could come to rest in such a way as to put a dangerous amount of weight and pressure on the patient's eyes, thus risking blindness to the patient.

It is with these observations of surgical tables and the various challenges they introduce, among other observations, that various aspects of the present disclosure were conceived and developed.

SUMMARY

Implementations described and claimed herein address the foregoing problems, among others, by providing a surgical table having a patient support platform extending from a single column support structure that is positioned on a base. The patient platform or support structure includes a rigid outer frame and an articulating inner frame that is coupled with the rigid outer frame via a sliding and pivoting hinge that allows a patient's upper body to remain in substantially the same position while simultaneously articulating the patient's spino-pelvic unit and hips and articulating the table at the sliding hinge. The hinge is configured to translate during pivoting in order to compensate for the movement associated with the bending of the patient's body, as is required for proper spino-pelvic biomechanics. Thus, the sliding and pivoting hinge eliminates the need for a sliding or translating chest platform or "trunk translator" since the hinges compensate for the patient movement by simultaneously translating and pivoting. That is, instead of having a pair of hinges at a fixed location on the patient support structure and using a sliding chest platform to compensate for and provide the required trunk translation, the surgical table described herein includes a translating and pivoting hinge that allows for the upper body of the patient to remain stationary. Since the patient's head remains in the same position during articulating of the surgical table, there is significantly less risk that the anesthetic equipment will be dislodged from the patient, or that other adverse events will occur.

Aspects of the present disclosure involve a surgical table for supporting a patient over a floor and including a base assembly, a support column assembly and a patient support structure. The base assembly supported on the floor and including a first end, a second end opposite the first end, and a member extending along a base longitudinal axis between the first and second ends. The support column assembly moveably coupled with the base assembly and configured to translate between the first and second ends of the base assembly along the member extending therebetween, the support column assembly being the only support column assembly coupled with the base assembly. The patient support structure including a first end, a second end opposite the first end, and a longitudinal axis extending between the first and second ends, the second end of the patient support structure supported off of the support column assembly in a cantilevered fashion.

Aspects of the present disclosure involve a surgical table for supporting a patient over a floor and including a base assembly, a support column assembly coupled with the base assembly, and a patient support structure. The base assembly supported on the floor and including a first end, a second end opposite the first end, and a member extending along between the first and second ends. The patient support structure including a first end, a second end opposite the first end, an upper body portion, a lower body portion, and a hinge comprising an axis of rotation positioned between the first and second ends and coupling the upper and lower body portions. The second end of the patient support structure being coupled to the support column assembly, the hinge configured to articulate the lower body portion relative to the upper body portion about the axis of rotation and into a flexed position and an extended position. The axis of rotation of the hinge configured to move towards the first end of the patient support structure when the lower body portion articulates into the flexed position and configured to move towards the second end of the patient support structure when the lower body portion articulates into the extended position. The upper body portion of the patient support structure remaining in a neutral position when the lower body portion articulates into the flexed position and the extended position.

Aspects of the present disclosure involve a surgical table surgical table for supporting a patient over a floor and including a base assembly, a support column assembly coupled with the base assembly, and a patient support structure. The base assembly supported on the floor and comprising a first end, a second end opposite the first end, and a member extending between the first and second ends. The patient support structure including a first end, a second end opposite the first end, an upper body portion comprising a slot, a lower body portion coupled with the upper body portion via a bearing shaft cooperating with the slot to form a hinge. The bearing shaft configured to slide and translate within the slot to define a movable axis of rotation for the hinge, wherein translational movement of the bearing shaft within the slot shortens or lengthens a distance between the first end of the patient support structure and the movable axis of rotation.

Other implementations are also described and recited herein. Further, while multiple implementations are disclosed, still other implementations of the presently disclosed technology will become apparent to those skilled in the art from the following detailed description, which shows and describes illustrative implementations of the presently disclosed technology. As will be realized, the presently disclosed technology is capable of modifications in various aspects, all without departing from the spirit and scope of the presently disclosed technology. Accordingly, the drawings and detailed description are to be regarded as illustrative in nature and not limiting.

BRIEF DESCRIPTION OF THE DRAWINGS

FIG. 13 is rotated 180 degrees.

FIG. 15 is rotated 180 degrees.

DETAILED DESCRIPTION

Figure 1:
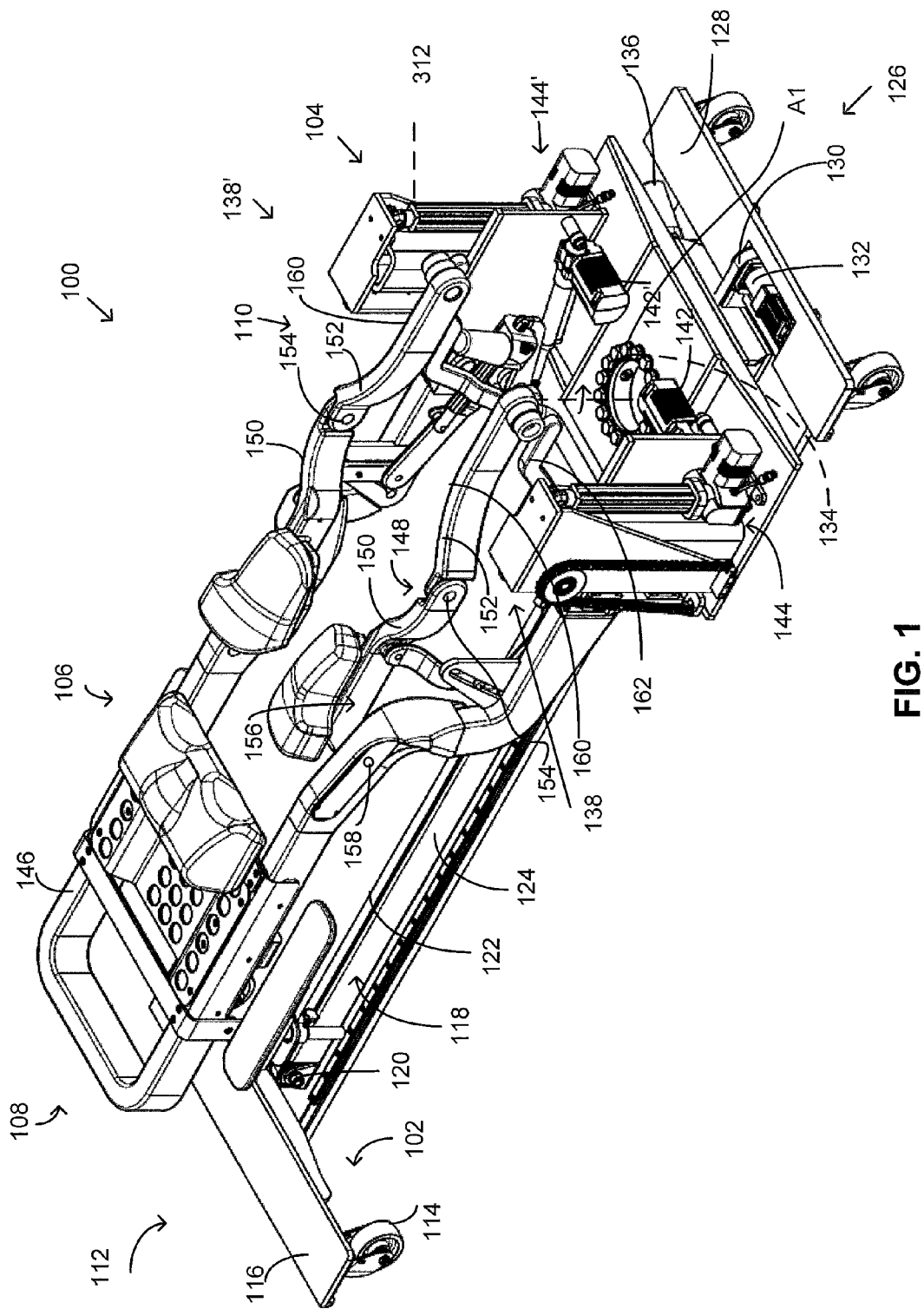
FIG. 1 is an isometric foot end view of an example surgical table with a patient support extending from a support column, wherein the patient support is shown in a neutral position.
Figure 2:
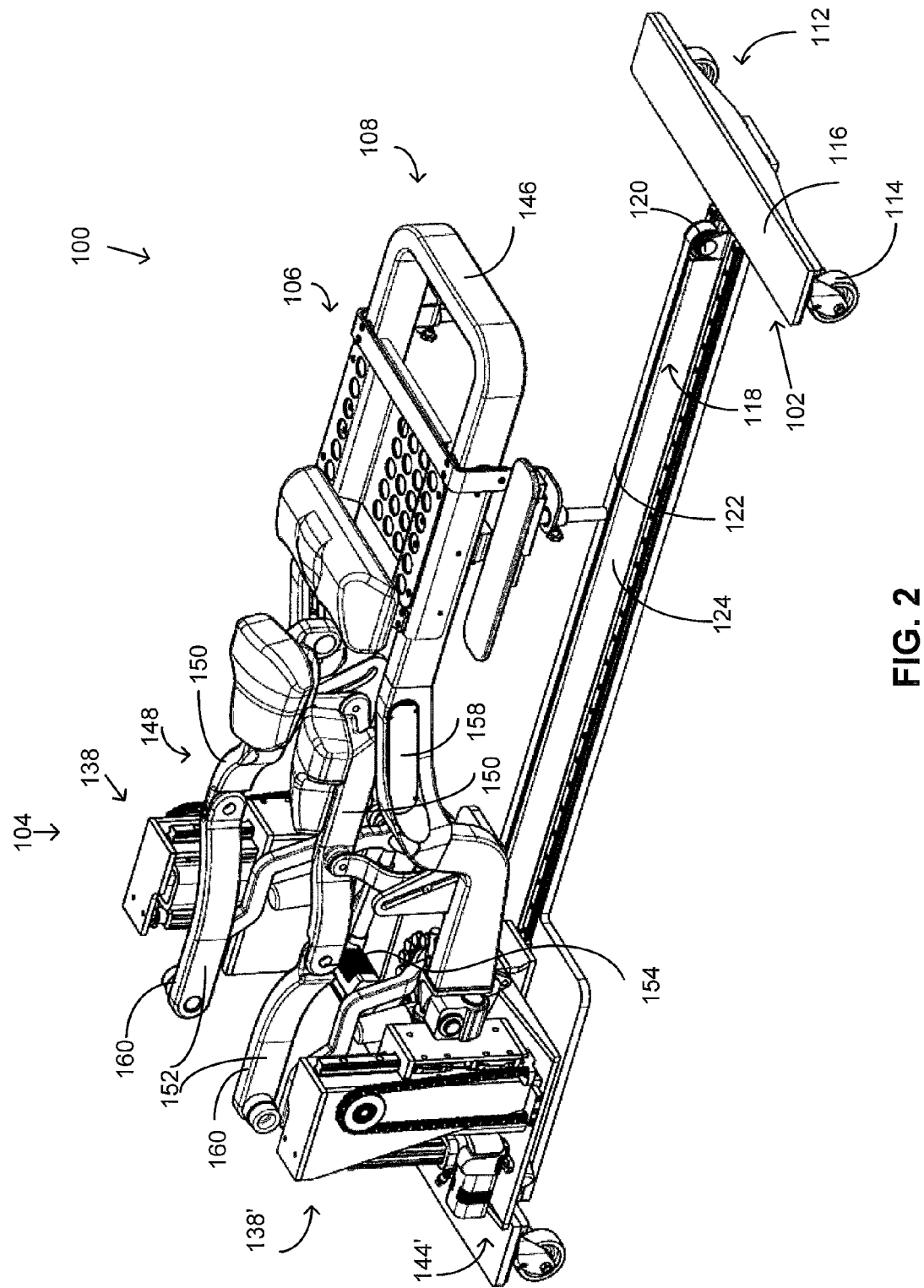
FIG. 2 is another isometric view of the surgical table of FIG. 1.
Figure 3:
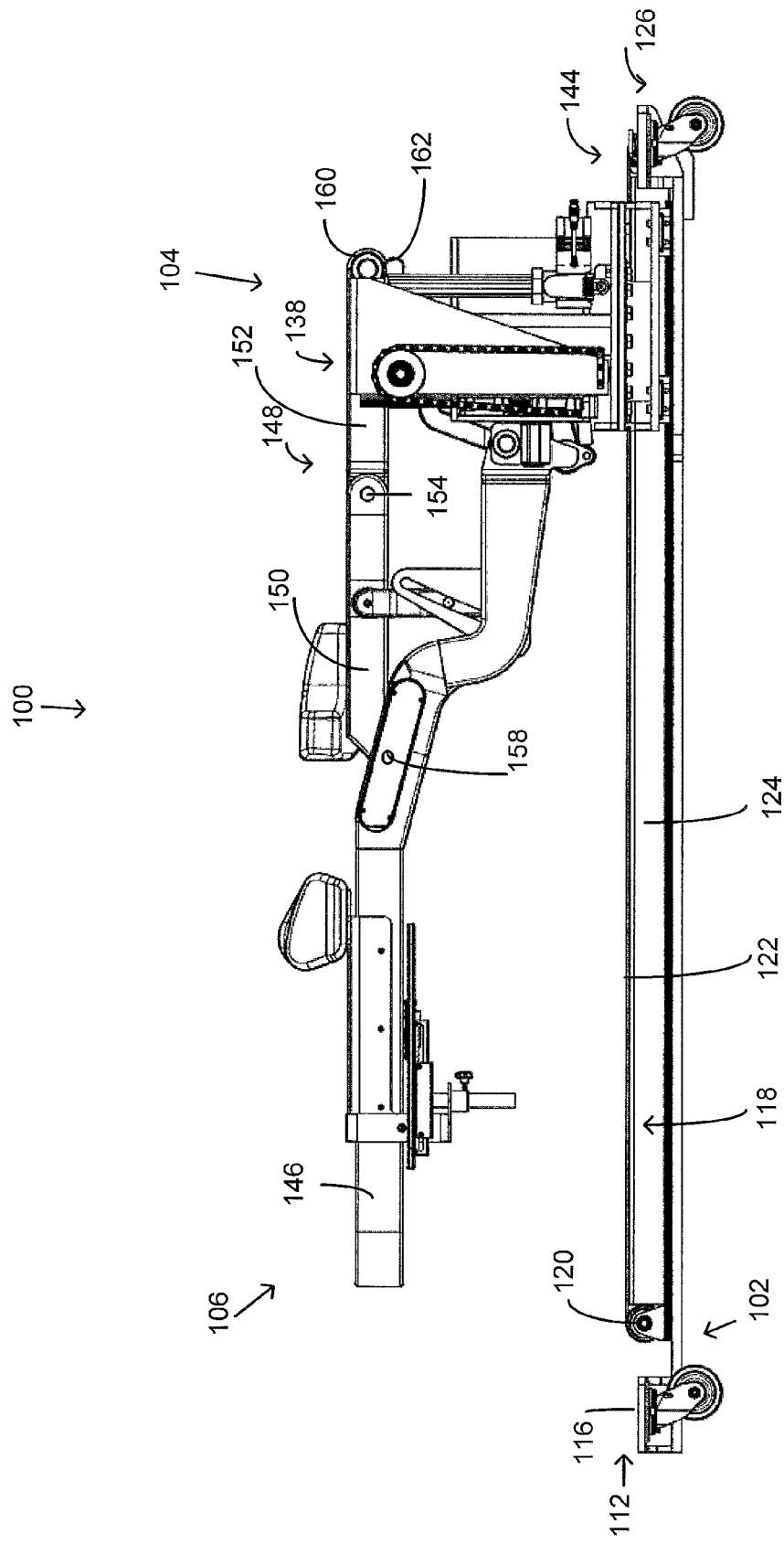
FIG. 3 is a side view of the surgical table of FIG. 1.
Figure 4:
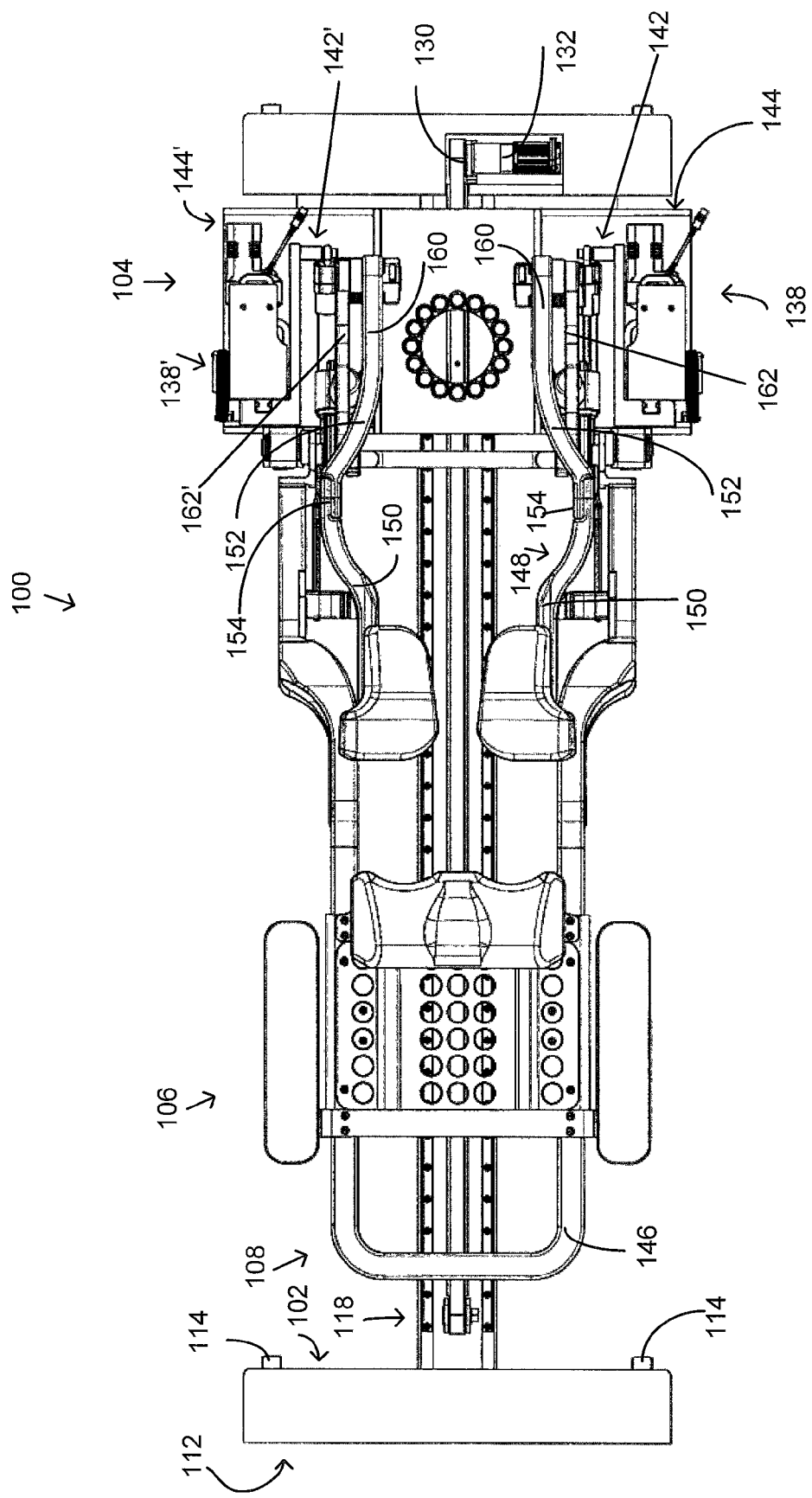
FIG. 4 is a top view of the surgical table of FIG. 1.
Figure 5:
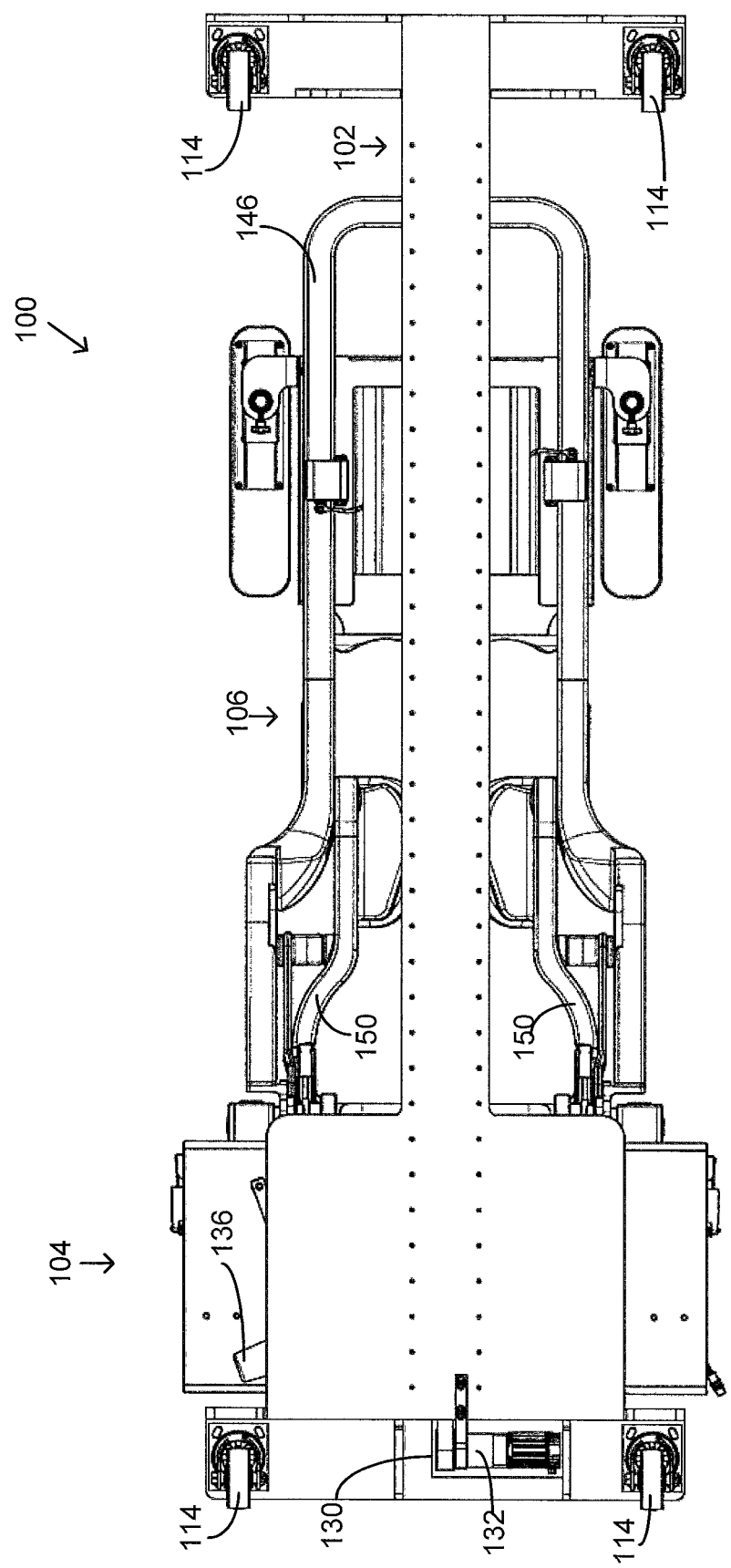
FIG. 5 is a bottom view of the surgical table of FIG. 1.

Aspects of the present disclosure involve a patient positioning and support structure or surgical table with a single, end column assembly that translates and pivots relative to a base assembly and supports one end of a patient support platform in a cantilevered fashion. Generally the surgical table is configured to support the patient in various position while permitting tilting, swiveling, and/or rolling of the patient with respect to the floor, along a horizontal axis, and while simultaneously maintaining the patient's head in a suitable location for administration of anesthesia. The end column assembly is uniquely configured to track along a base structure which acts as a counter balance, as further described herein.

The base includes a forward end having a pair of spaced apart and lockable caster wheels extending downward from a plate and towards a floor. Extending rearwardly from the forward end is a track assembly having a forward end pulley, a belt, and a rigid track supporting a weight of the portions of the surgical table translating thereon. A rearward end of the track assembly is coupled to a base plate at a back end of the base. More particularly, the rearward end of the track assembly includes a back end pulley rotatably coupled with the belt and supported on the track and the base plate. At the back end, the back end pulley is rotatably coupled to a rotary motor (e.g., servo motor) that is configured to rotate the pulleys and belt to translate the single column support assembly fore and aft. The base plate may include a pair of spaced apart and lockable caster wheels extending downward and towards the floor. The base plate may additionally include weights (e.g., steel plates) to offset a tipping force causes by a patient being positioned on the patient support platform when the single column support assembly is in a forward-most position and the platform is positioned beyond the forward end of the base, thereby providing a counter balance.

The single column support assembly or support column is moveably coupled to the base and configured to translate fore and aft on the track assembly between the forward end and the back end. The support column is also configured to pivot side-to-side, angulate the patient support platform up and down (i.e., Trendelenburg, reverse Trendelenburg), elevate and lower the patient support platform, and roll the patient support platform. To facilitate these movements, there are a number of subassemblies that will be subsequently described in detail with specific reference to the figures.

The patient support platform includes a rigid outer frame and a displaceable and articulating inner frame that are operably coupled to the support column. That is, the patient support platform is cantilevered off of the support column. One advantage, among many, of having a cantilevered patient support platform is that the patient can be conveniently positioned within an opening or "donut" of a scanning machine without having the patient moved to a separate imaging table, or having the scanning machine move. Thus, the patient may undergo medical imaging before, during, or after a surgical procedure without relocating to a separate imaging table, etc.

The rigid outer frame is pivotably coupled with the support column and is configured to support a torso region of a patient when the patient is in a prone position (i.e., a body position in which the patient lies flat with the chest down and back up), for example. Additionally, the patient support platform is configured to support a patient in various other positions, including, but not limited to, a supine position (i.e., a body position in which the patient lies flat with the chest up and back down), a lateral-decibitus position (i.e., a body position in which the patient lies on his or her side), a Trendelenburg position (i.e., a body position with the feet higher than the head), a reverse Trendelenburg position (i.e., a body position with the head higher than the feet), and the like.

The inner frame is a hinged structure including an upper leg member and a lower leg member separated by a hinge. The rigid outer frame is coupled with a forward end of the upper leg member of the inner frame via a sliding and translating hinge that is configured to accommodate the patient's moving in flexion and extension without causing the patient's upper body to slide or move on the rigid outer frame. Opposite the forward end of the upper leg member, a rearward end of the lower leg member is in sliding contact with a guide member that is coupled with the support column and guides the rearward end of the lower leg member when the inner frame articulates into a flexed position. A linkage assembly is operably coupled between the support column and the inner frame and is configured to drive or facilitate movement of the upper and lower leg members of the inner frame.

I. The Surgical Table—Single Column

For a detailed description of an example surgical table 100 for positioning and supporting a patient during medical procedures, such as surgery and imaging, reference is made to FIGS. 1-5. In one implementation, the table 100 includes a base assembly (hereinafter "base") 102 supported on a floor surface, a support column assembly (hereinafter "support column") 104 supported on the base 102, and a patient support structure (hereinafter "patient support") 106. The patient support 106 includes a head end 108 and a foot end 110 and is supported on the foot end 110 in a cantilevered fashion by the support column 104. The patient support 106, among other components of the table 100, may include features as described in U.S. Provisional Patent Application No. 62/021,630, filed on Jul. 7, 2014, titled "SURGICAL TABLE WITH PATIENT SUPPORT HAVING FLEXIBLE INNER FRAME SUPPORTED ON RIGID OUTER FRAME", which is hereby incorporated by reference in its entirety into the present application.

It is appreciated that the patient support 106 may be suspended above the floor using other bases, mobile structures, permanent structures (e.g., ceiling, walls, or other building structures), and/or the like. Furthermore, the patient support 106 may include one or more additional patient support structures adapted to hold patients of various sizes and shapes (e.g., pediatric patients, tall patients, obese patients, etc.), to provide support for a particular medical procedure, or the like. The patient support 106 may additionally include more or more removable, replaceable, and/or interchangeable portions and parts, such as flat tops and cushions, as well as other accessories, such as arm supports and traction units.

The base 102 includes a forward end 112 having a pair of spaced apart and lockable caster wheels 114 extending downward from a plate 116 and towards a floor. While caster wheels 114 are shown in the figures, other supports are possible. Extending rearwardly from the forward end 112 is a track assembly 118 having a forward end pulley 120, a belt 122, and a rigid track 124 supporting a weight of the portions of the surgical table 100 translating thereon. A rearward end of the track assembly 118 is coupled to a base plate 128 at a back end 126 of the base 102. More particularly, the rearward end of the track assembly 118 includes a back end pulley 130 rotatably coupled with the belt 122 and supported on the track 124 and the base plate 128. At the back end, the back end pulley 130 is rotatably coupled to a rotary motor 132 (e.g., servo motor) that is configured to rotate the pulleys 120, 130 and belt 122 to translate the support column 104 fore and aft (i.e, towards the forward end 112 of the base 102 and towards the back end 126 of the base 102). The base plate 128 may include a pair of spaced apart and lockable caster wheels 114 extending downward and towards the floor. The base plate 128 may additionally include weights (e.g., steel plates) (not shown) to offset a tipping force caused by a patient being positioned on the patient support 106 when the support column 104 is in a forward-most position and the patient support 106 is positioned beyond the forward end 112 of the base 102. This improved counter balance feature makes the table more stable and safer.

The support column 104 is rotatably coupled with the base 102 via a slewing ring bearing 134 that is driven by an electric linear actuator 136 positioned on the base plate 128. When the linear actuator 136 is actuated, the support column 104 is configured to pivot about an axis A1. The support column 104 includes a pair spaced-apart column assemblies 138, 138' positioned on a mounting plate 140. Each column assembly 138, 138' includes an angulation assembly 142, 142' and a lift assembly 144, 144'. The angulation assemblies 142, 142' are configured to angle the patient support 106 relative to the floor to position the patient in Trendelenberg or Reverse Trendelenberg, for example, by lowering and raising the head end 108 of the patient support 106. The lift assemblies 144, 144' are configured to vertically raise and lower the patient support 106 relative to the floor. When used in conjunction with each other, the assemblies are configured to roll the patient support 106 through a certain degree of rotation about a longitudinal axis of the patient support 106. These and other functions and capabilities of the table 100 will be described in further detail below.

The patient support 106 includes a rigid outer frame 146 that is pivotably coupled with the column assemblies 138, 138' and is configured to support a torso region of a patient when the patient is in the prone position, for example. Additionally, the patient support 106 is configured to support a patient in various other positions as described previously, including, but not limited to, a supine position, a lateral-decibitus position, a Trendelenburg position, a reverse Trendelenburg position, and the like.

The patient support 106 further includes an inner frame 148 that is a hinged structure including an upper leg member 150 and a lower leg member 152 separated by a hinge 154. The rigid outer frame 146 is coupled with a forward end 156 of the upper leg member 150 of the inner frame 148 via a sliding and translating hinge 158 that is configured to accommodate the patient's moving in flexion and extension without causing the patient's upper body to slide or move on the rigid outer frame. Opposite the forward end 156 of the upper leg member 150, a rearward end 160 of the lower leg member 152 is in sliding contact with a guide member 162, 162' that is coupled with the column assemblies 138, 138' and guides the rearward end 160 of the lower leg member 152 when the inner frame 148 articulates into a flexed position.

Referring to FIG. 1, among others, the support column 104 may also include a user device 312, which may be generally any form of computing device capable of interacting with the table 100 and controlling the various operations of the table 100, such as a personal computer, workstation, terminal, portable computer, mobile device, mobile phone, tablet, multimedia console, and the like. The support column 104 may include a control box housing one or more electrical components, such as electrical wiring, junctions, circuitry, and the like, associated with the operation and control of the table 100 as directed by the user device 312 based on input from a user, such as a surgeon, technician, nurse, or other medical personnel. The user device 312 may receive the input from the user, for example, via a graphical user interface (GUI) using an input device, such as a mouse, keyboard, touch screen, or the like. In one implementation, the user device 312 is mounted to one of the column assemblies 138, 138' and includes a control box housing the one or more electrical components for controlling the operations of the table 100. The user device 312 may further receive inputs from and communicates with one or more sensors (e.g., motion sensors) to facilitate control of the operations of the table 100. In this way, the table 100 can translate and pivot into a pre-positioned C-arm in the operating room and then return to a home position to continue the operation or procedure.

A. The Base

Figure 6:
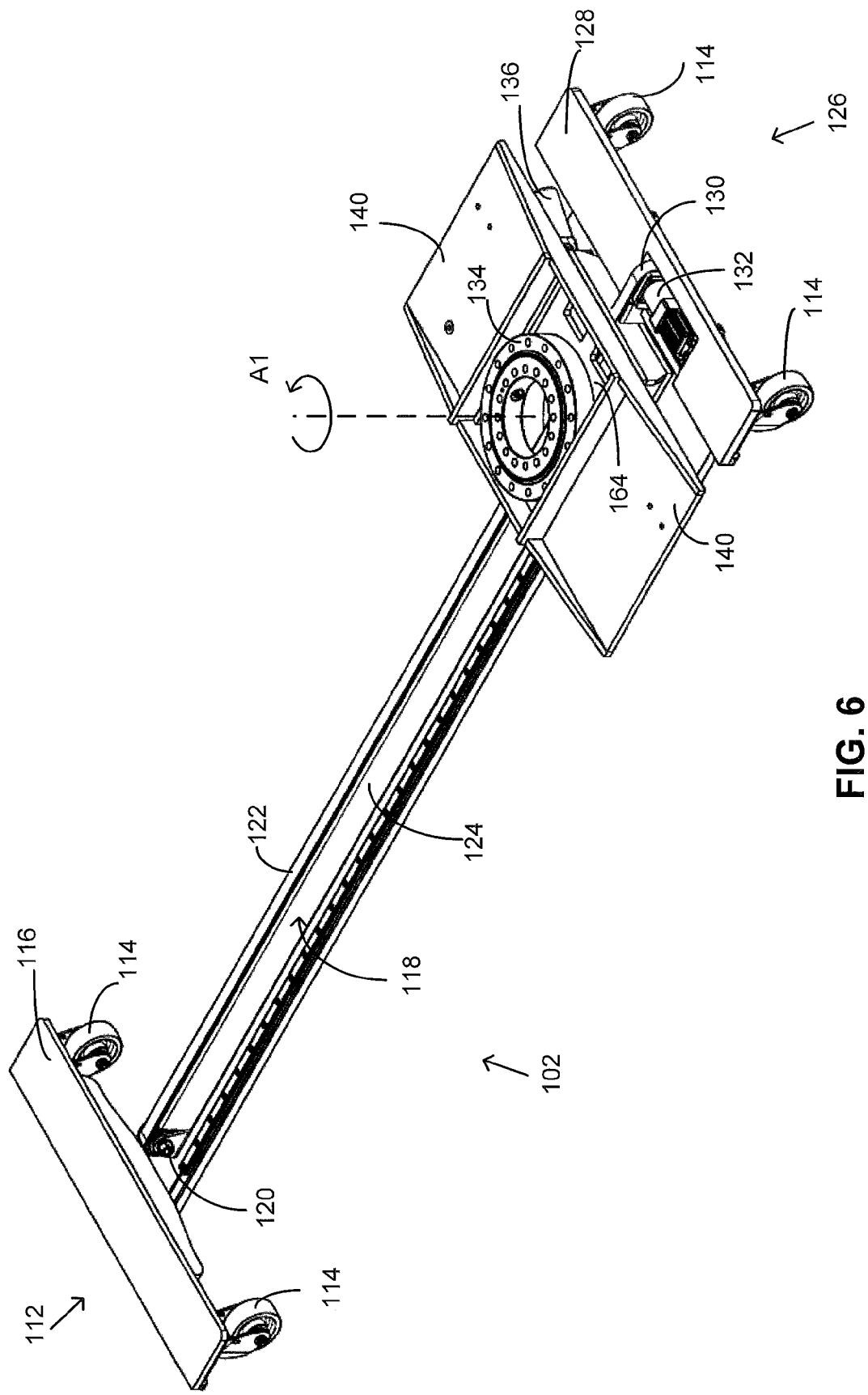
FIG. 6 is an isometric foot end view of the base assembly.
Figure 7:
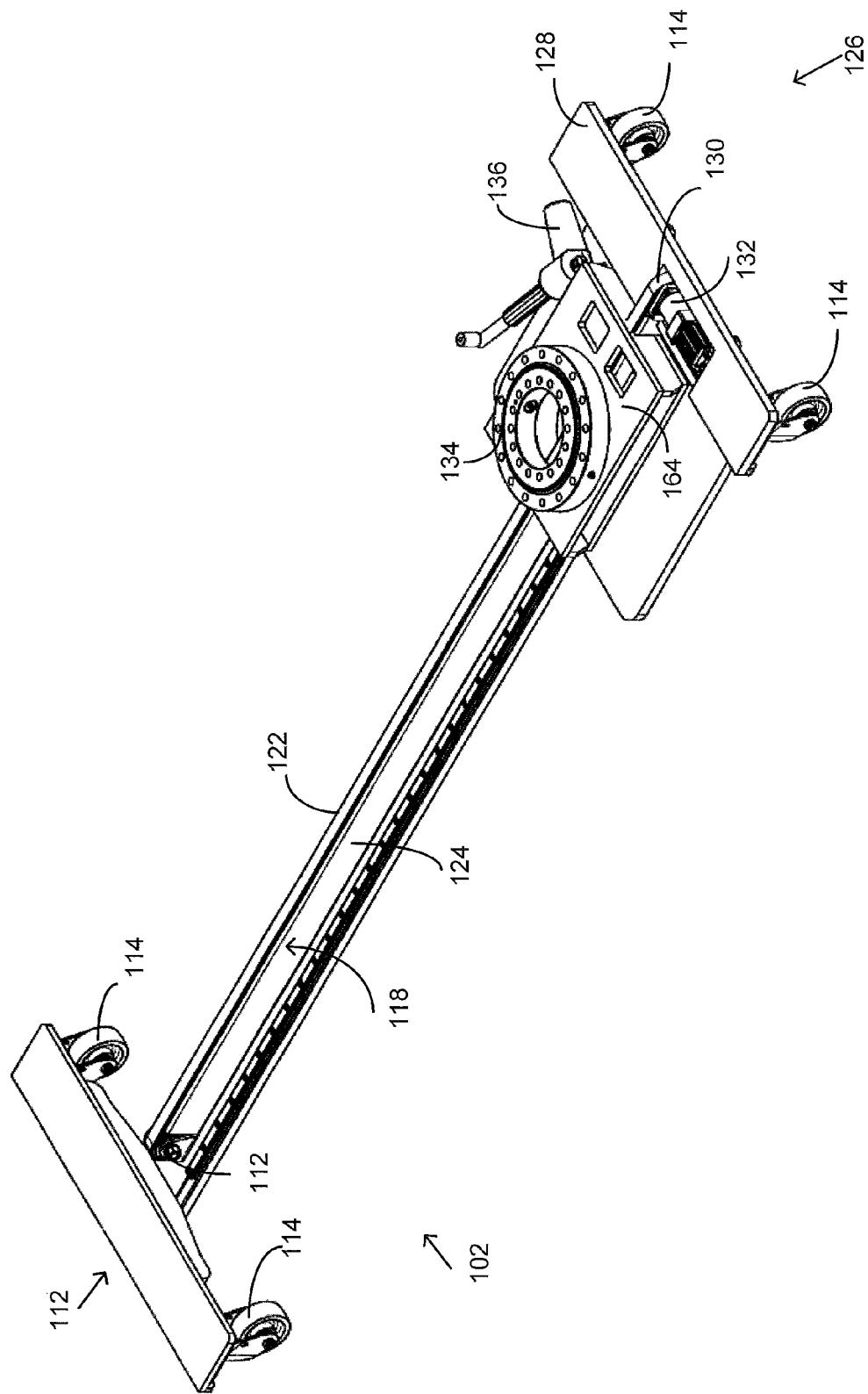
FIG. 7 is an isometric foot end view of the base assembly with the mounting plates hidden from view.
Figure 8:
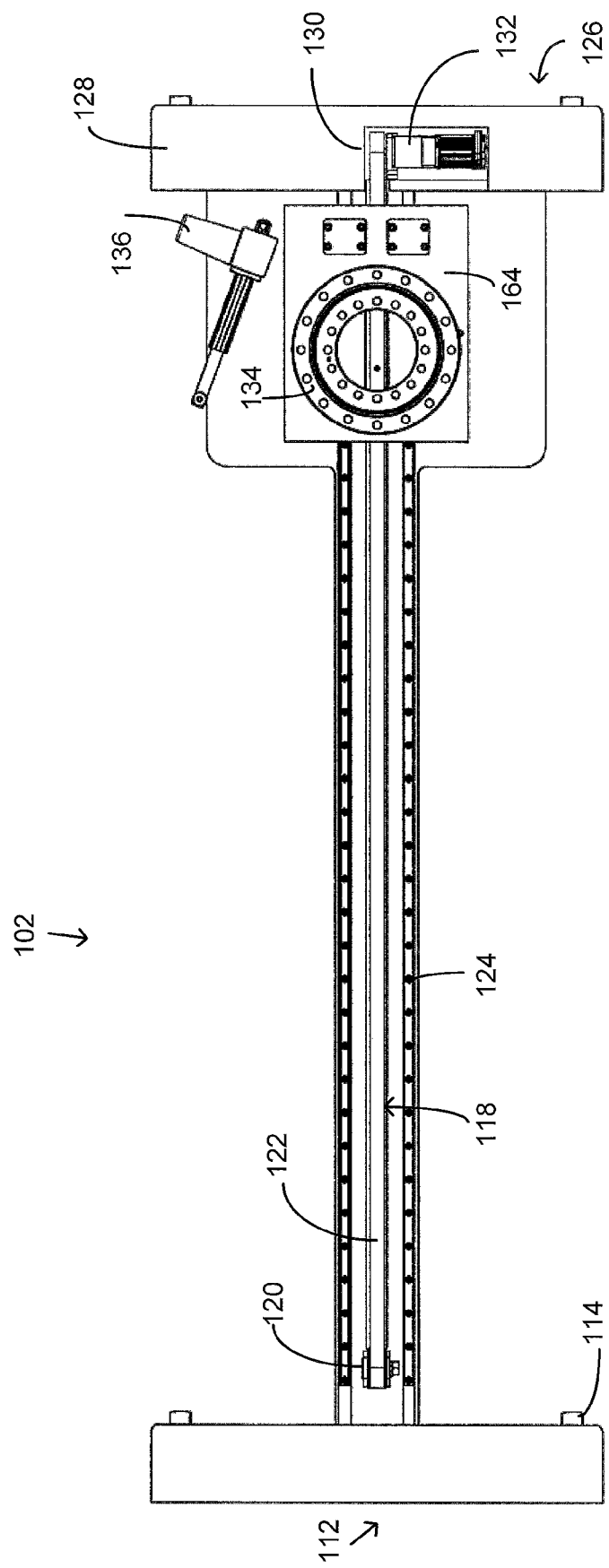
FIG. 8 is a top view of the base assembly of FIG. 7.

Reference is now made to FIGS. 6-10, which depict the base 102 while the remaining portions of the surgical table are hidden from view. As seen in FIG. 6, which is an isometric view of the base 102 as seen from the back end 126, the mounting plate 140 is coupled with a carriage assembly 164 that is rotatably coupled with the slewing ring bearing 134 such that as the linear actuator 136 is actuated, the carriage assembly 164, mounting plate 140 and, thus, all components supported thereon are pivoted about the axis A1 of rotation. As seen in FIG. 7, which is the same view as FIG. 6, except the mounting plate 140 is hidden from view, the linear actuator 136 is shown being coupled to the base plate 128 of the base 102. The carriage assembly 164 is coupled with the belt 122 such that when the rotary motor 132 rotates the back end pulley 130 and the belt is rotated between the pulleys 120, 130 the carriage assembly 164 is translated along the track 124 towards the forward end 112 of the base 102. And, once at the forward end 112 of the base 102, opposite rotation of the rotary motor 132 causes the carriage assembly 164 to translate on the track back towards the back end 126 of the base 102.

Figure 9:
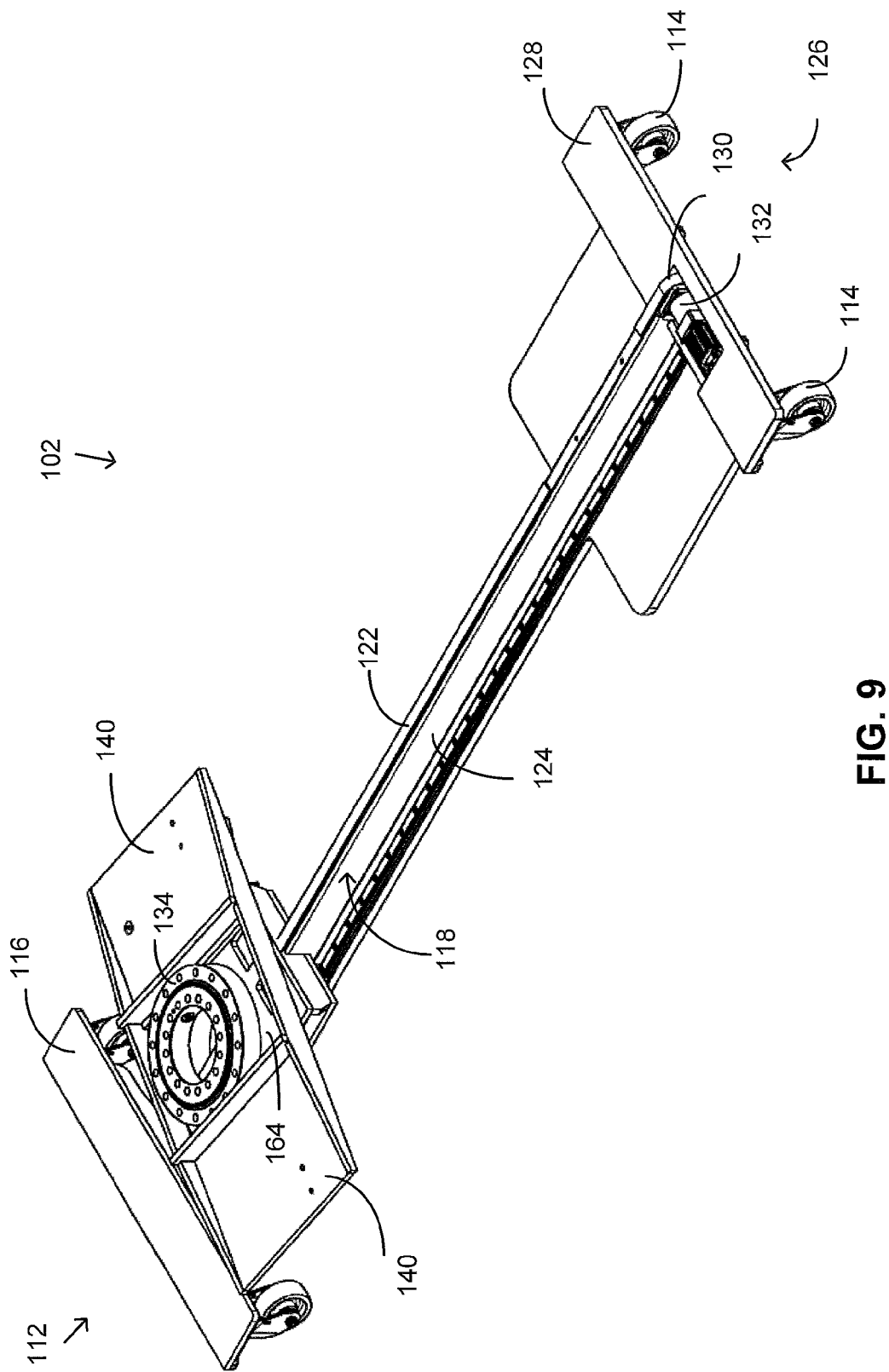
FIG. 9 is an isometric foot end view of the base assembly with the carriage assembly translated towards a head end of the base and pivoted relative to the carriage assembly.
Figure 10:
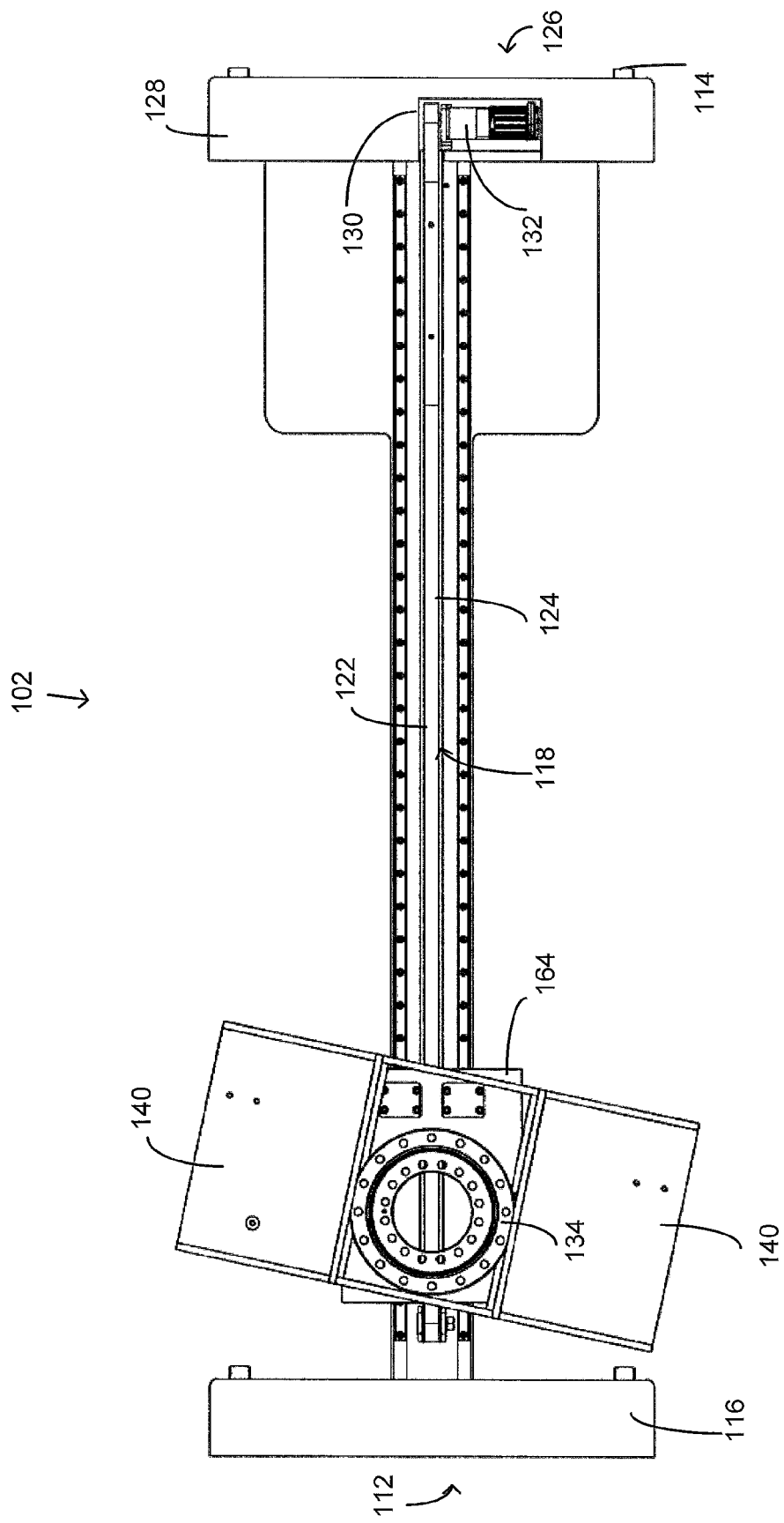
FIG. 10 is a top view of the base assembly as shown in FIG. 9.

FIGS. 9-10 illustrate the carriage assembly 164 at the forward end 112 of the base 102 with the mounting plate 140 pivoted relative to the carriage assembly 164. As seen in the figures, the mounting plate 140 has been translated to the forward end 112 of the base 102 via the track assembly 118 and the slewing ring bearing 134 has been rotated via the linear actuator 136 causing the mounting plate 140 to rotate about axis Al. In this and other embodiments of the surgical table, the mounting plate 140 and, thus, the column assemblies 138, 138' and the patient support are configured to pivot +/− about 12 degrees from a neutral position about the axis A1 of rotation. In certain implementations, the degree of rotation may be within a range of about +/−10 degrees to about +/−20 degrees.

The carriage assembly 164, plate 116, base plate, mounting plate 140, and track 124 may be constructed of standard steel or alloy components, among others. The linear actuator 136 and rotary motor 132 may be commercially available and DC operated.

B. The Support Column

Figure 11:
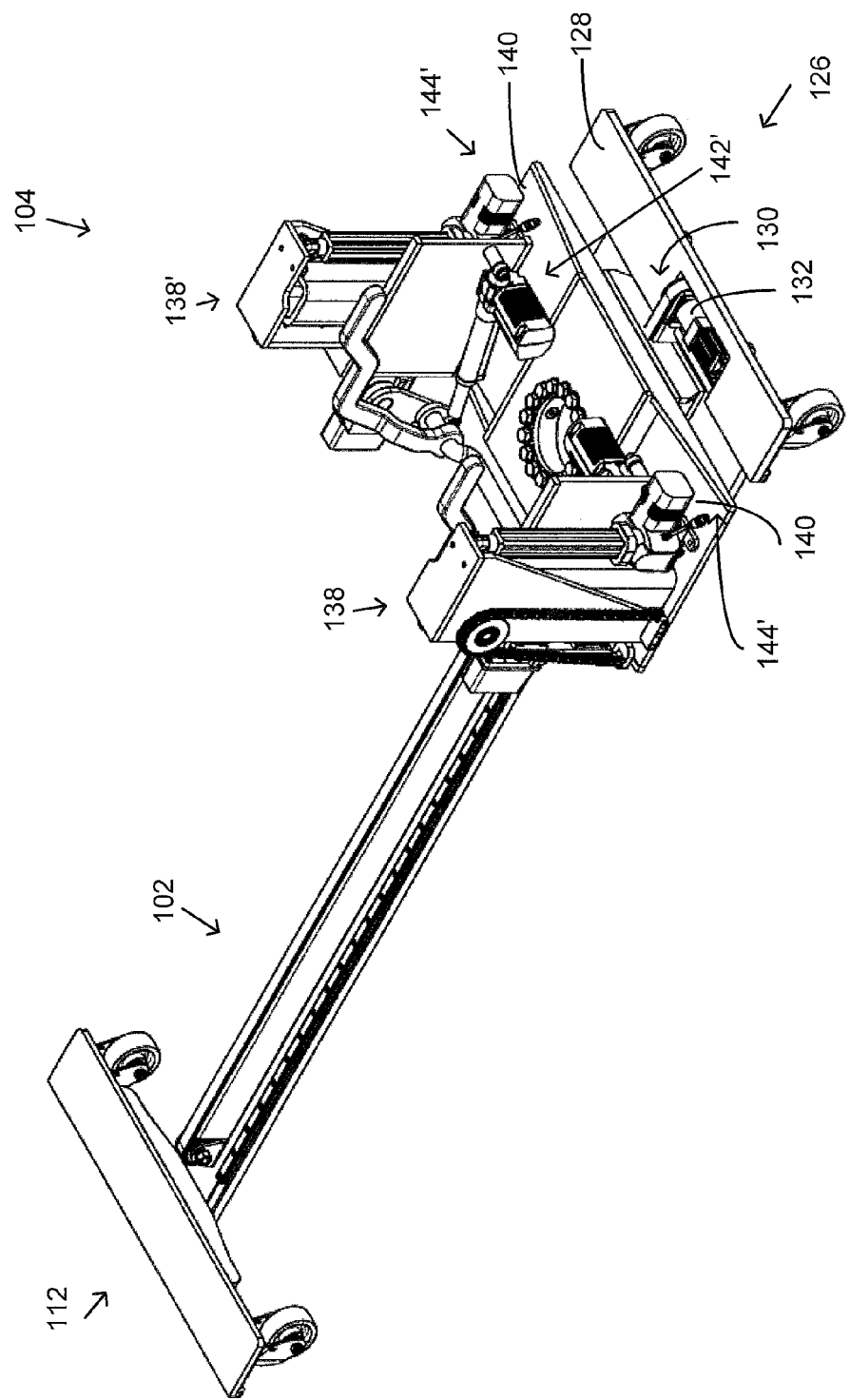
FIG. 11 is an isometric foot end view of the base assembly and support column with the patient support hidden from view.
Figure 12:
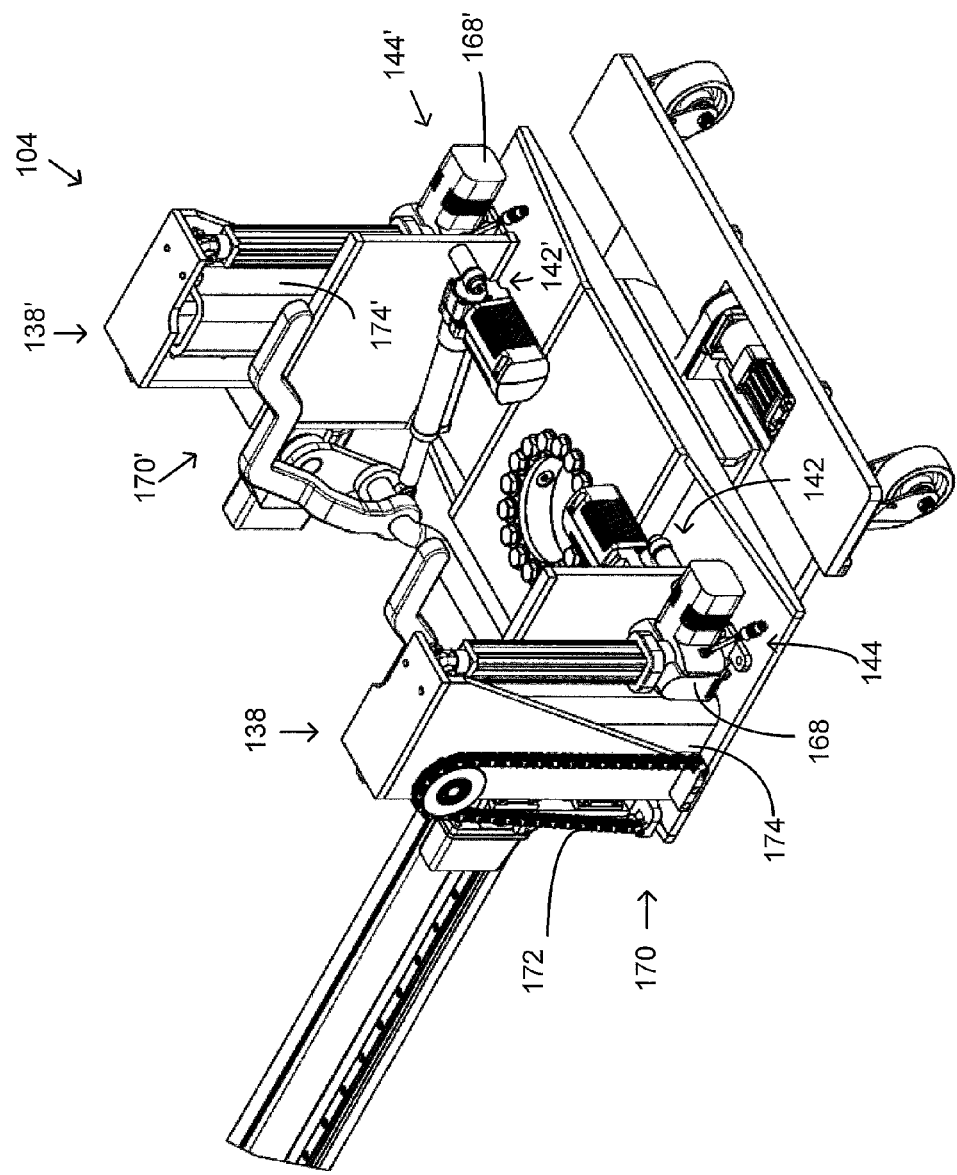
FIG. 12 is a close-up view of the support column as shown in FIG. 11.
Figure 13:
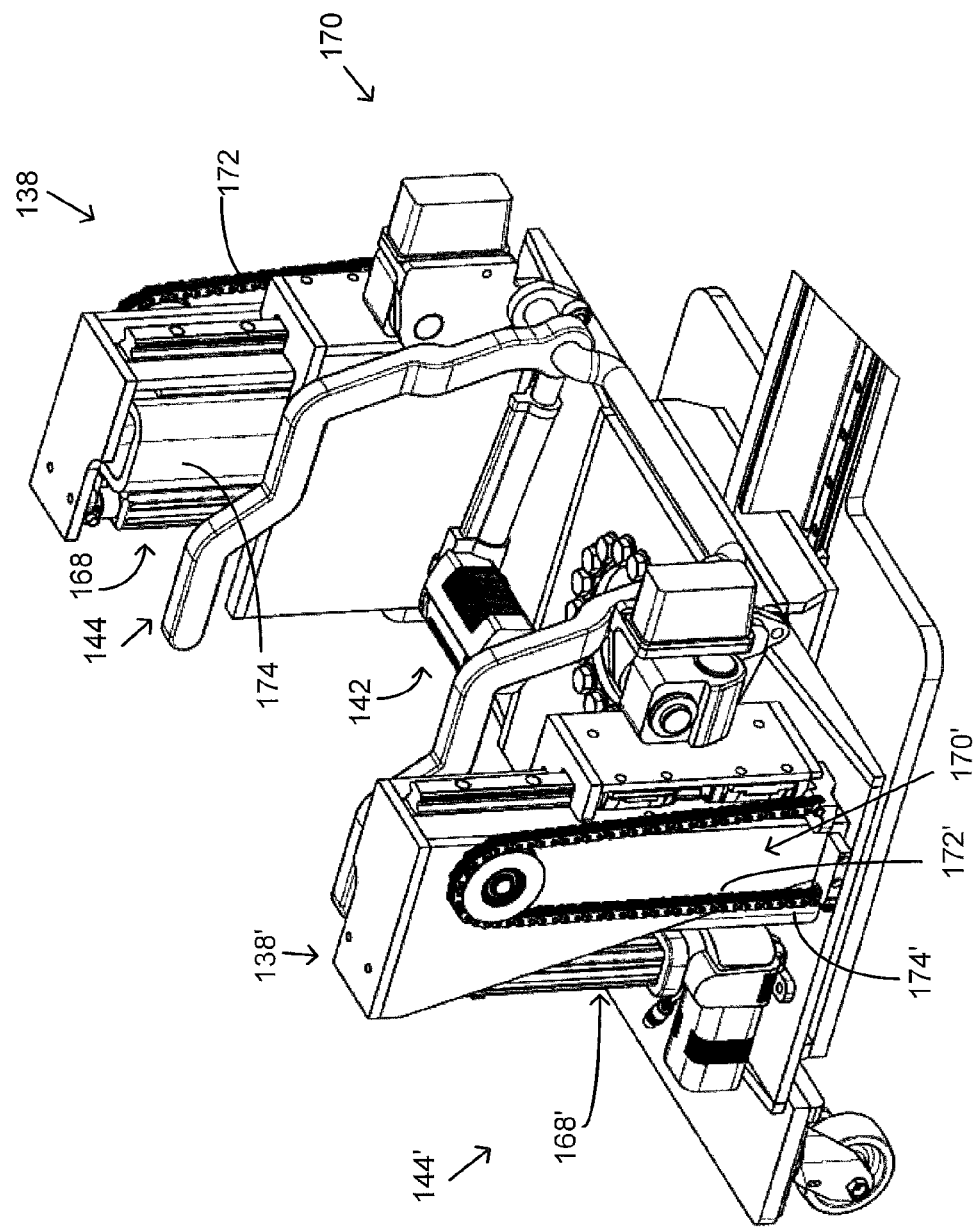
FIG. 13 is another close-up view of the support column as shown in FIG. 11, except

Reference is now made to FIGS. 11-20, which depict various views of the components of the support column 104. As seen in FIG. 11, which is an isometric view of the surgical table 100 with the patient support hidden from view, the column assemblies 138, 138' are coupled with the mounting plates 140 to form the support column 104 for the patient support (not shown). As best seen in FIGS. 12-13, which are close-up views of the column assemblies 138, 138' of FIG. 11, the column assemblies 138, 138' are mirror images of each other and are linked by a cross bar 166 extending between the assemblies.

Figure 14:
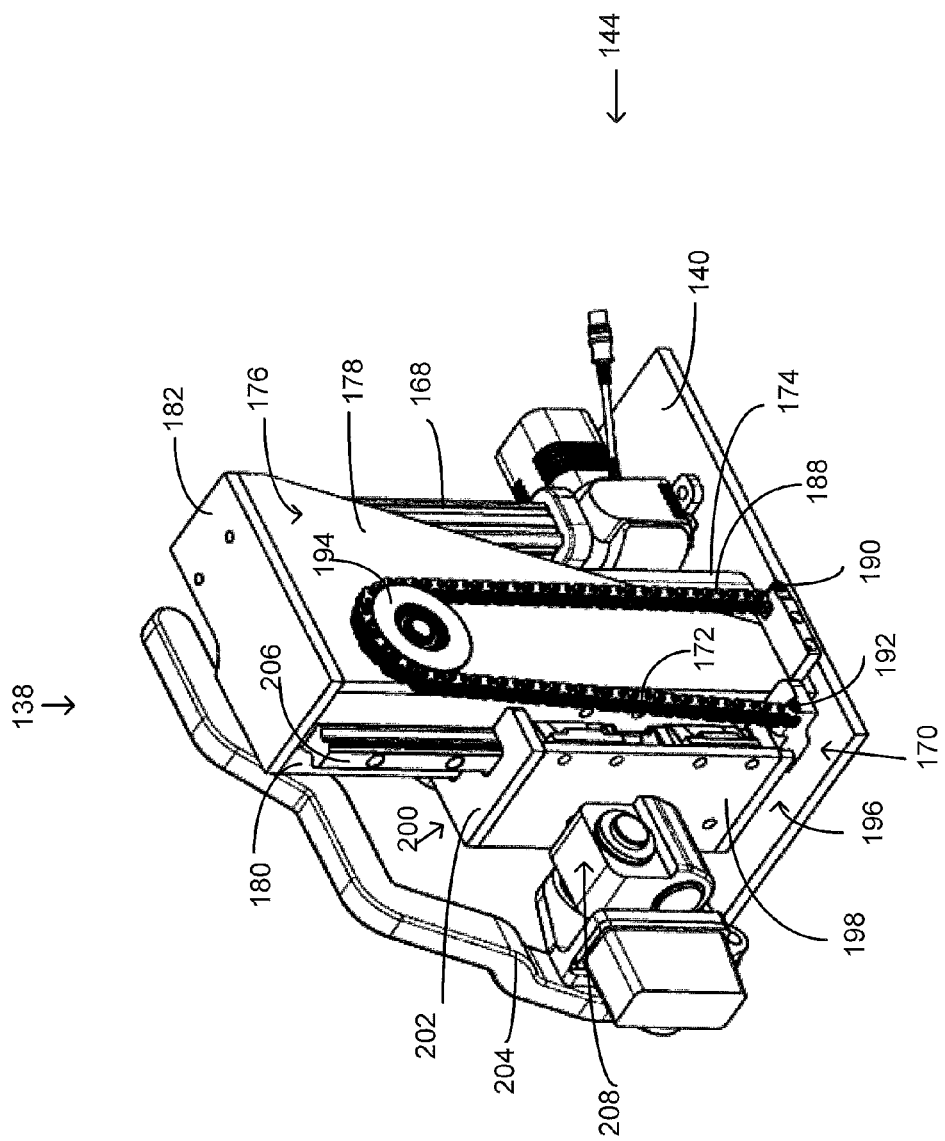
FIG. 14 is an isometric view of a column assembly of the support column.
Figure 15:
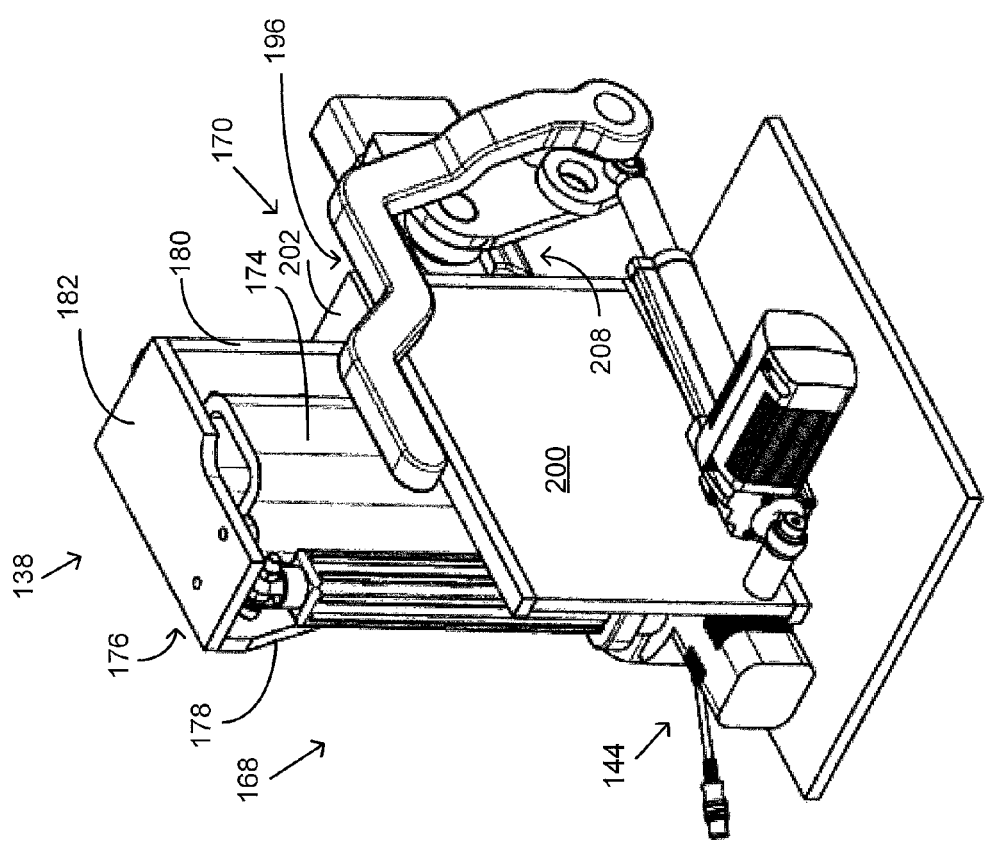
FIG. 15 is another isometric view of the column assembly of the support column as shown in FIG. 14, except
Figure 16:
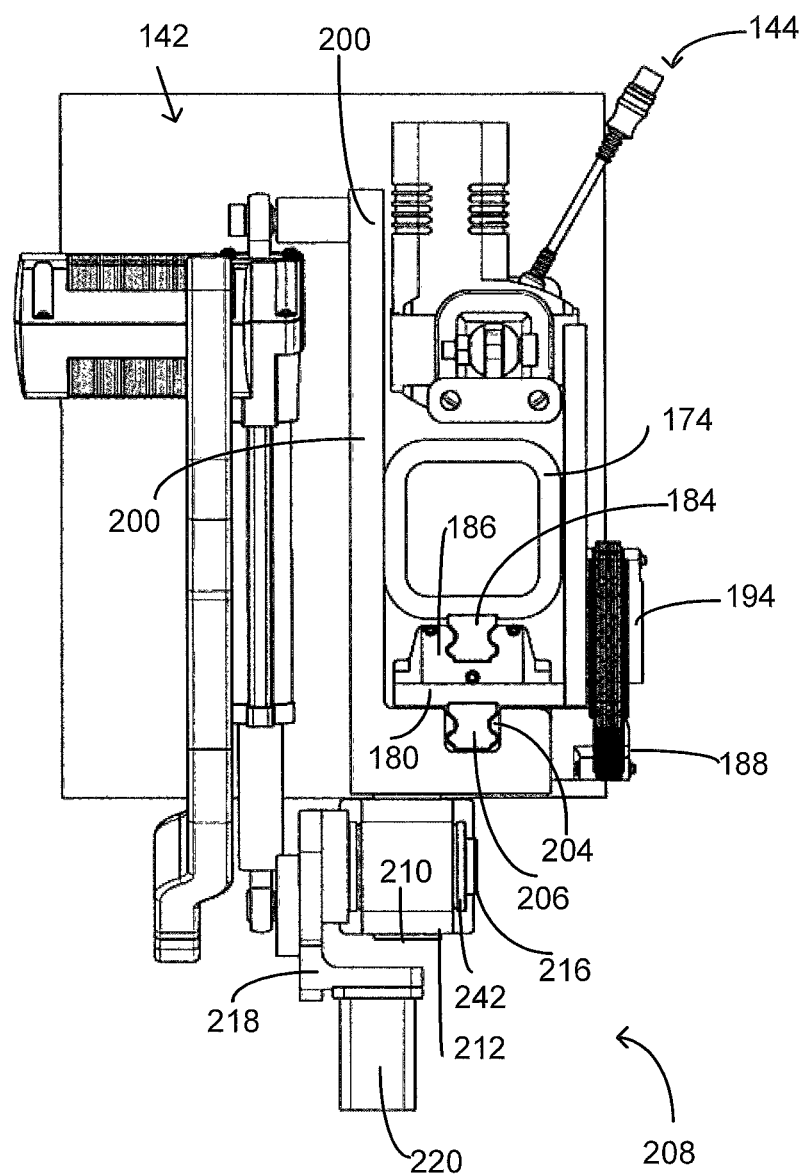
FIG. 16 is a top view of the column assembly of the support column of FIG. 14.

The lift assemblies 144, 144' each include a primary elevator 168, 168' in the form of an electric linear actuator 169, 169' and a secondary elevator 170, 170' in the form of a chain lift 172, 172' that effectively doubles the extension of the primary elevator 168, 168'. As seen in FIGS. 14-15, which are isometric views of the column assembly 138 shown on a portion of the mounting plate 140 with the other components of the support column 104 hidden from view, the column assembly 138 includes a rigidly mounted inner structure 174 that is a rectangular extrusion in the present embodiment. The inner structure 174, which can also be seen in a top down view in FIG. 16, extends generally upward and perpendicular from a surface of the mounting plate 140. Surrounding the inner structure 174 is a primary housing 176 that is configured to be raised and lowered by the extension and retraction of the primary elevator 168. The primary housing 176 includes an outer side member 178, a front side member 180, and a top side member 182. As best seen in FIG. 16, the primary housing 176 is slidably coupled with the inner structure 174 via a linear rail 184 and carriage 186. The linear rail 184 is affixed to a front surface of the inner structure 174 and the carriage 186 is affixed to a back surface of the front side member 180. Thus, when the primary elevator 168 is actuated, the primary housing 176 is raised and is guided by the linear rail 184 and carriage 186 being supported by the inner structure 174.

The secondary elevator 170 functions in conjunction with and does not operate independently from the primary elevator 168. That is, the secondary elevator 170 is a passive elevator 170 that functions to effectively increase the overall lift of the patient support (not shown) with the use of the chain lift 172. The chain lift 172 includes a chain 188 that is affixed to the mounting plate 140 at one end 190 and is affixed to a second housing 196 at a second end 192 that is opposite the first end 190. In between the first end 190 and the second end 192, the chain 188 is guided over a pulley 194 that is coupled with the outer side member 178 of the primary housing 176. The second housing 196 includes a front side member 198, an inner side member 200, and a top side member 202. Within the second housing 196 is a carriage 204 that is slidably coupled with a rail 206 that is affixed to a front surface of the front side member 180 of the primary housing 176.

Figure 17:
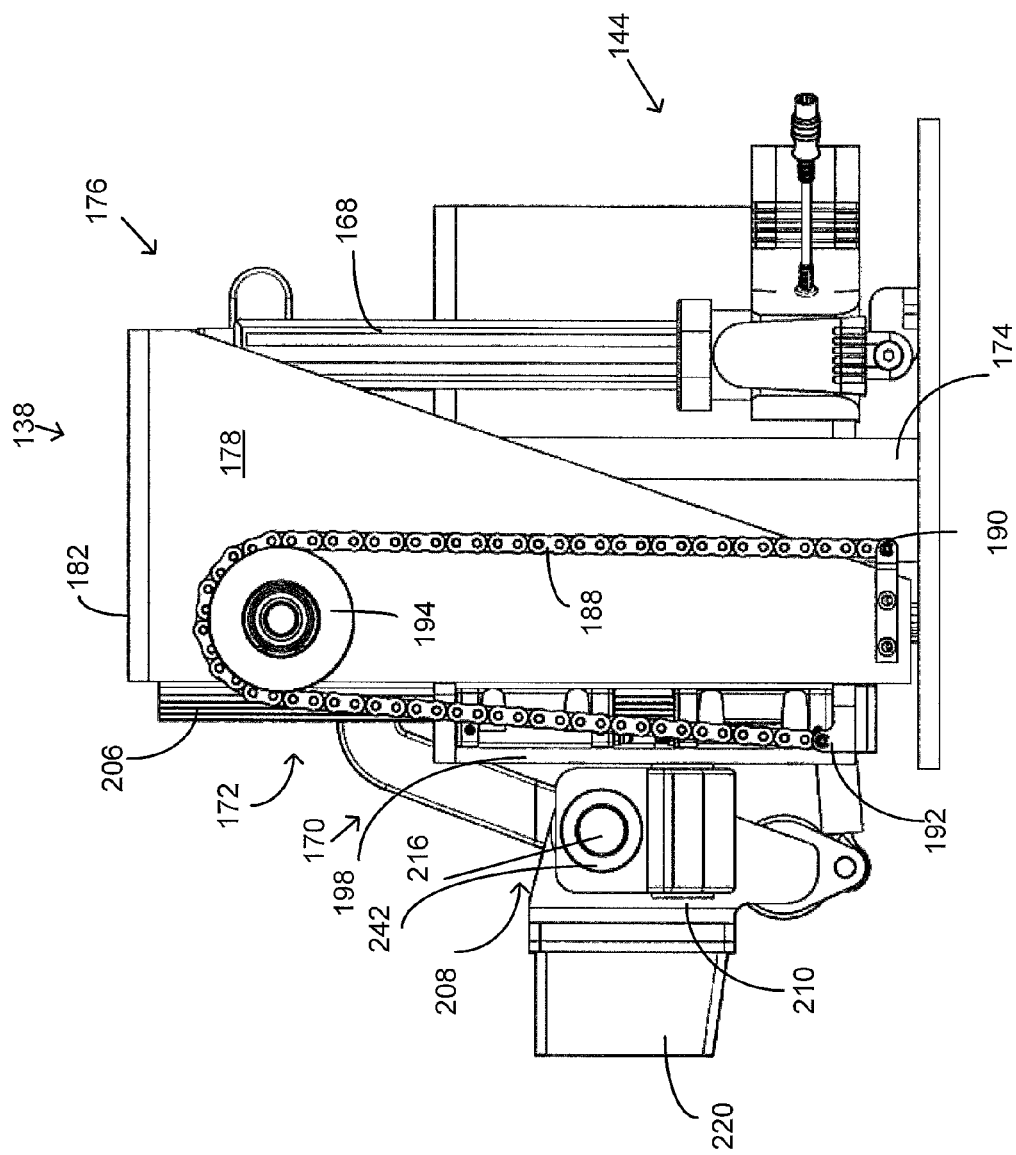
FIG. 17 is a side view of the column assembly of the support column of FIG. 14.
Figure 18:
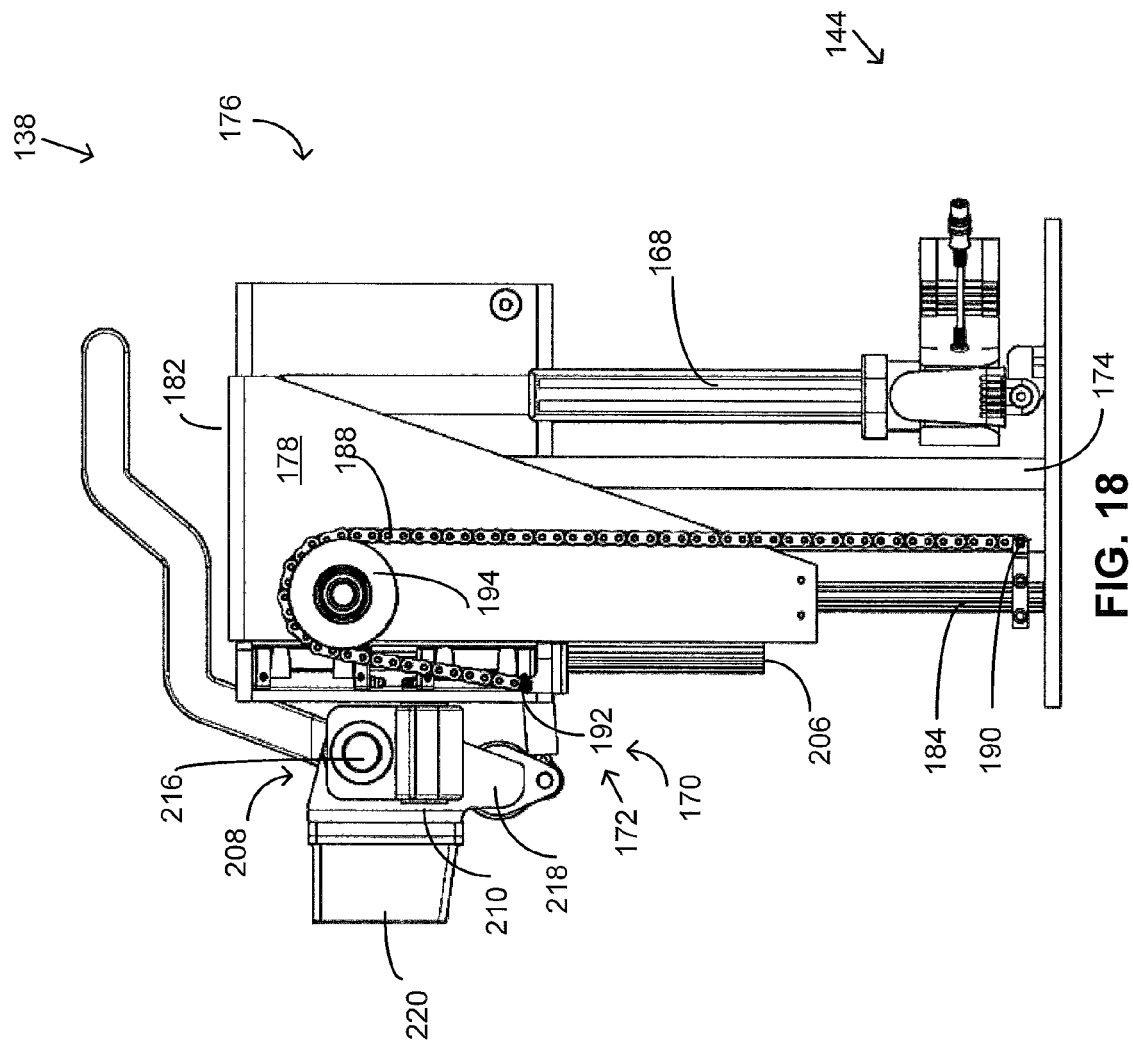
FIG. 18 is a side view of the column assembly of the support column of FIG. 14 in an elevated or lifted state.

The chain 188 is a fixed length such that as the primary housing 176 is elevated by the primary elevator 168, the chain 188 pulls the secondary housing 196 upward along the rail 206 as the chain 188 is routed around the pulley 194. To further illustrate the movements of the elevators 168, 170, reference is made to FIGS. 17-18, where FIG. 17 is a side view of the column assembly 138 with the elevators 168, 170 in a lowered or retracted state and where FIG. 18 is a side view of the column assembly 138 with the elevators 168, 170 in a lifted or extended state. As seen in FIG. 17, the primary elevator 168 is not yet extended. In this state, the secondary housing 196 resides on a bottom portion of the rail 206 that is coupled to the front side member 180 of the primary housing 176. As the linear actuator 169 of the primary elevator 168 is actuated and extends, as seen in FIG. 18, the primary housing 176 is raised, which causes the secondary housing 196 to be raised since the pulley 194 that guides and supports the chain 188 is coupled with the primary housing 176. The chain lift 172 serves to effectively double the extension or lift of the patient support (not shown) that would otherwise not happen without the chain lift 172. That is, while the extension of the primary elevator 168 may be about 200 millimeters (mm), the extension of the patient support with the chain lift 172 as the secondary elevator 170 causes the total lift or extension to be about 400 mm, effectively doubling the overall lift.

As best seen in FIGS. 14 and 16-18, a multi-axle bearing block 208 is pivotally coupled with the front side member 198 of the second housing 196 via a cylindrical shaft 210 extending forward from the front side member 198 and through a bore 212 of the block 208. The multi-axle bearing block 208 is, thus, able to pivot about the cylindrical shaft 210 to facilitate certain orientations of the patient support (not shown), such as, for example, a rolled position caused by offset elevations of the lift assemblies 144, 144'. The bearing block 208 includes another bore 214 that is transverse or approximately perpendicularly oriented from the other bore 212. A cylindrical shaft 216 extends through the transverse bore 214 and transitions to an L-shaped plate member 218 that extends around a head portion of the bearing block 208 and is operably coupled with a patient support plug 220 that couples the support column 104 with the patient support 106. In addition to being operably coupled with the lift assemblies 144, 144' via the bearing block 208, 208', the plate member 218 is also operably coupled with the angulation assemblies 142, 142', as will be described below.

Figure 19:
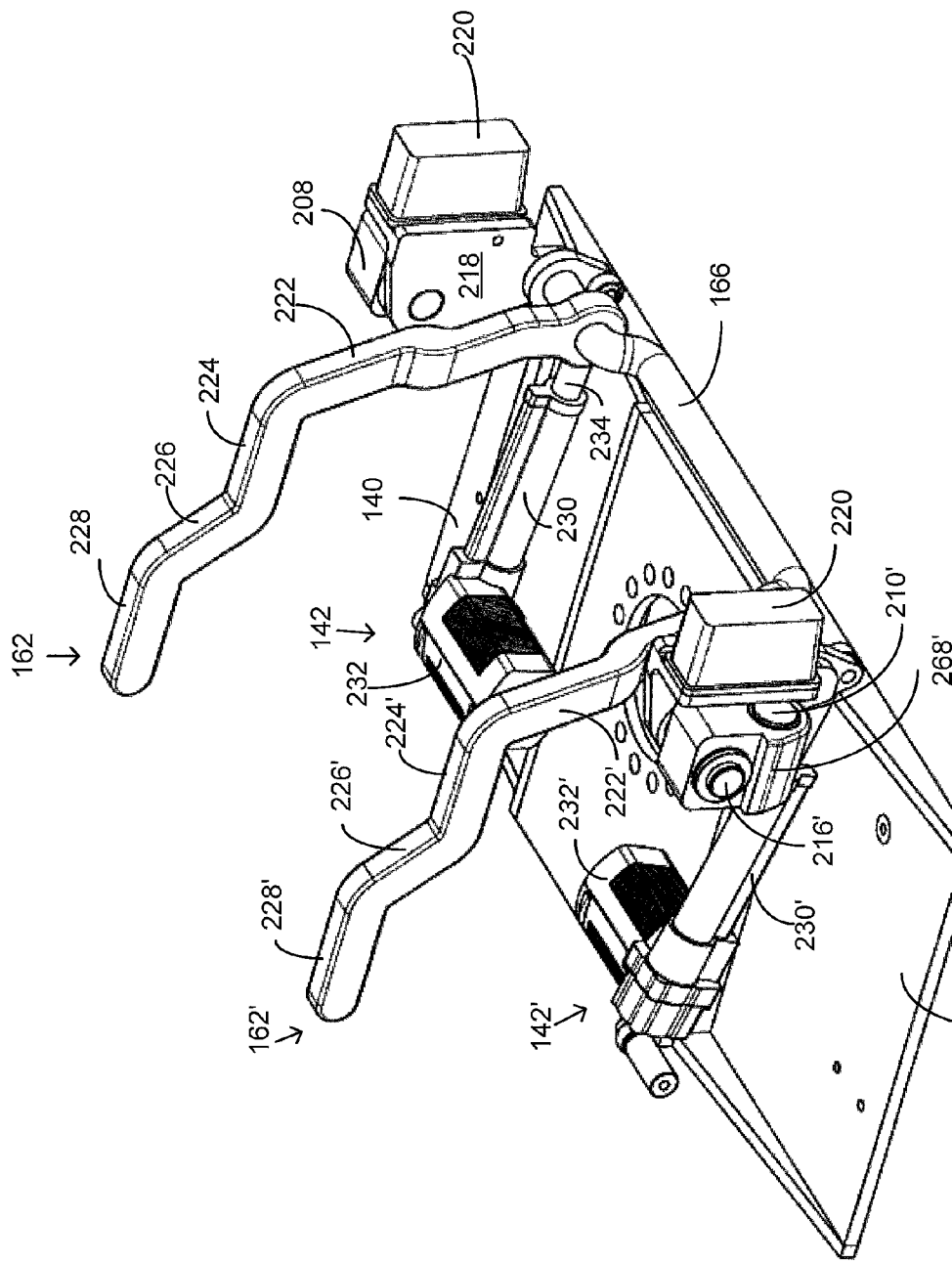
FIG. 19 is an isometric view of the angulation assemblies with the base assembly and patient support, among other components, hidden from view.

The multi-axle bearing blocks 208, 208' are coupled with the lift assemblies 144, 144' and the angulation assemblies 142, 142' such that movement associated with each assembly ultimately affects the patient support 106 extending from the patient support plug 220. Reference is now made to FIGS. 19-23, which depict various views of the angulation assemblies 142, 142' and the bearing blocks 208, 208' with many components of the surgical table hidden from view. As seen in FIG. 19, which is an isometric view of the angulation assemblies 142, 142' positioned above the mounting plates 140 and a top surface of the carriage assembly 164, the angulation assemblies 142, 142' are mirror images of each other and are linked by the cylindrical cross bar 166 extending between the mounting plates 140. Inward of the bearing blocks 208, 208' and coupled with the cross bar 166 are the guide members 162, 162'. The guide members 162, 162' are four sided members extending upward from the cross bar 166 and including a first angled section 222 near the connection with the cross bar 166, a second horizontal section 224 extending rearward of the first angled section 222, a third angled section 226 extending upward and rearward, and a fourth horizontal section 228 extending rearward from the third angled section 226. As will be discussed below in reference to the patient support 106, the guide members 162, 162' are configured to support and guide the rearward end 160 of the lower leg member 152 of the inner frame 148 of the patient support 106 as it articulates about the hinge 154 between the upper and lower leg members 150, 152.

As seen in FIG. 19, each angulation assembly 142, 142' includes an electric linear actuator 230, 230' depicted as right angle linear actuators with a motor 232, 232' and a telescoping rod 234, 234'. Although not shown in FIG. 19, the motors 232, 232' are coupled to the inner side members 200, 200' of the second housing 196, 196'. Thus, the angulation assemblies 142, 142' are raised and lowered by the lift assemblies 144, 144'. Turning to FIG. 20, which is an isometric view of the angulation assembly 142, cross bar 166, and bearing block 208 with the remaining portions of the surgical table hidden from view, the telescoping rod 234 is coupled to an outer end of a plate member 236 having an egg-shaped cross section via a spherical bearing 238. As seen in FIGS. 20-23, the plate member 236 is rigidly coupled to the cross bar 166 and the L-shaped plate member 218 that extends up to the bearing block 208. The plate member 218 includes a bore 240 for the cylindrical shaft 216 to extend therethrough. The plate members 218, 236 are configured to pivot about a central axis A2 of the cylindrical shaft 216 when the telescoping rod 234 of the angulation assembly 142 extends and retracts. That is, the patient support plug 220 and, thus, the patient support 104 can be angled upwards and downwards (e.g., reverse Trendelenberg, Trendelenberg) by the linear actuator 230 extending and retracting the telescoping rod 234, which causes the egg-shaped plate member 236 and the upwardly extending plate member 218 to pivot about the central axis A2 of the cylindrical shaft 216. A radial distance R1 between the central axis A2 of the cylindrical shaft 216 and the universal bearing 238 is about 150 centimeters (cm). In certain embodiments, the radial distance R1 may be within a range of about 100 cm to about 300 cm.

Figure 20A:
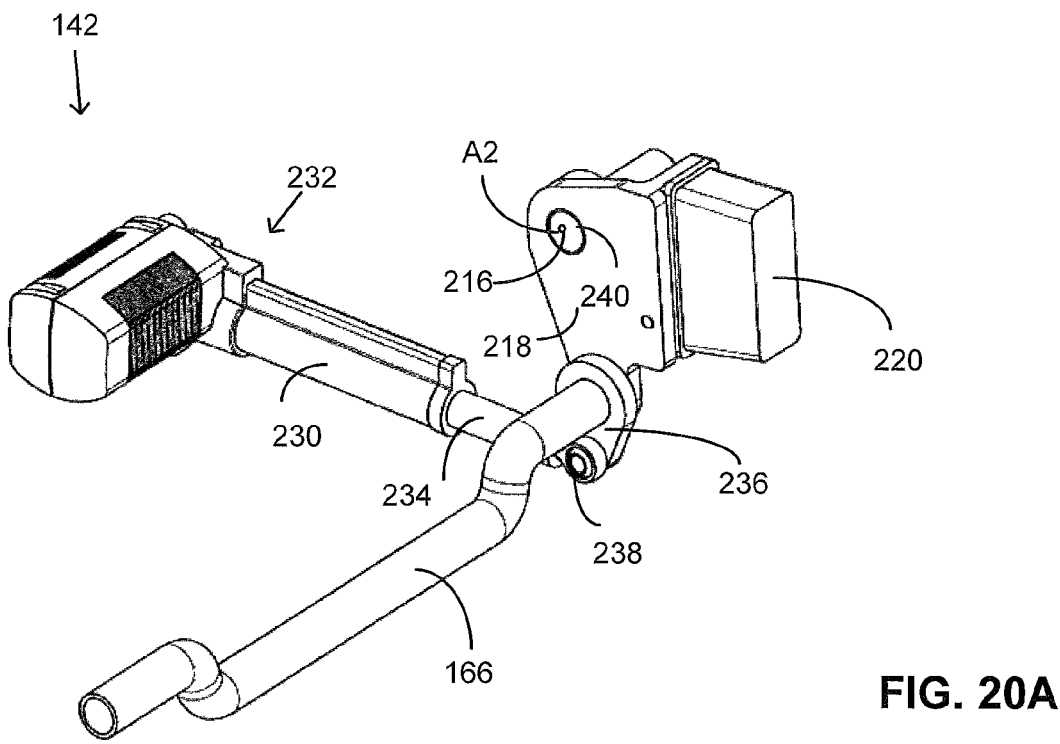
FIG. 20A is an isometric view of one of the angulation assemblies coupled with the cross-bar.
Figure 20B:
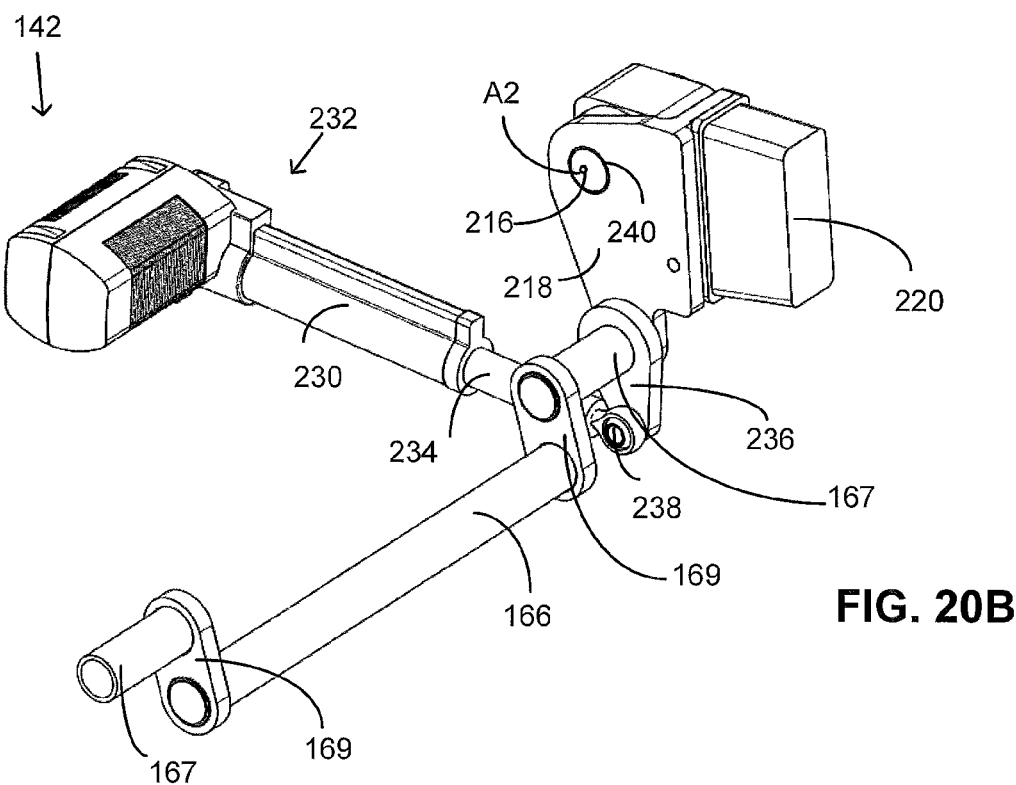
FIG. 20B is an isometric view of the angulation assembly with another embodiment of the cross-bar.
Figure 21:
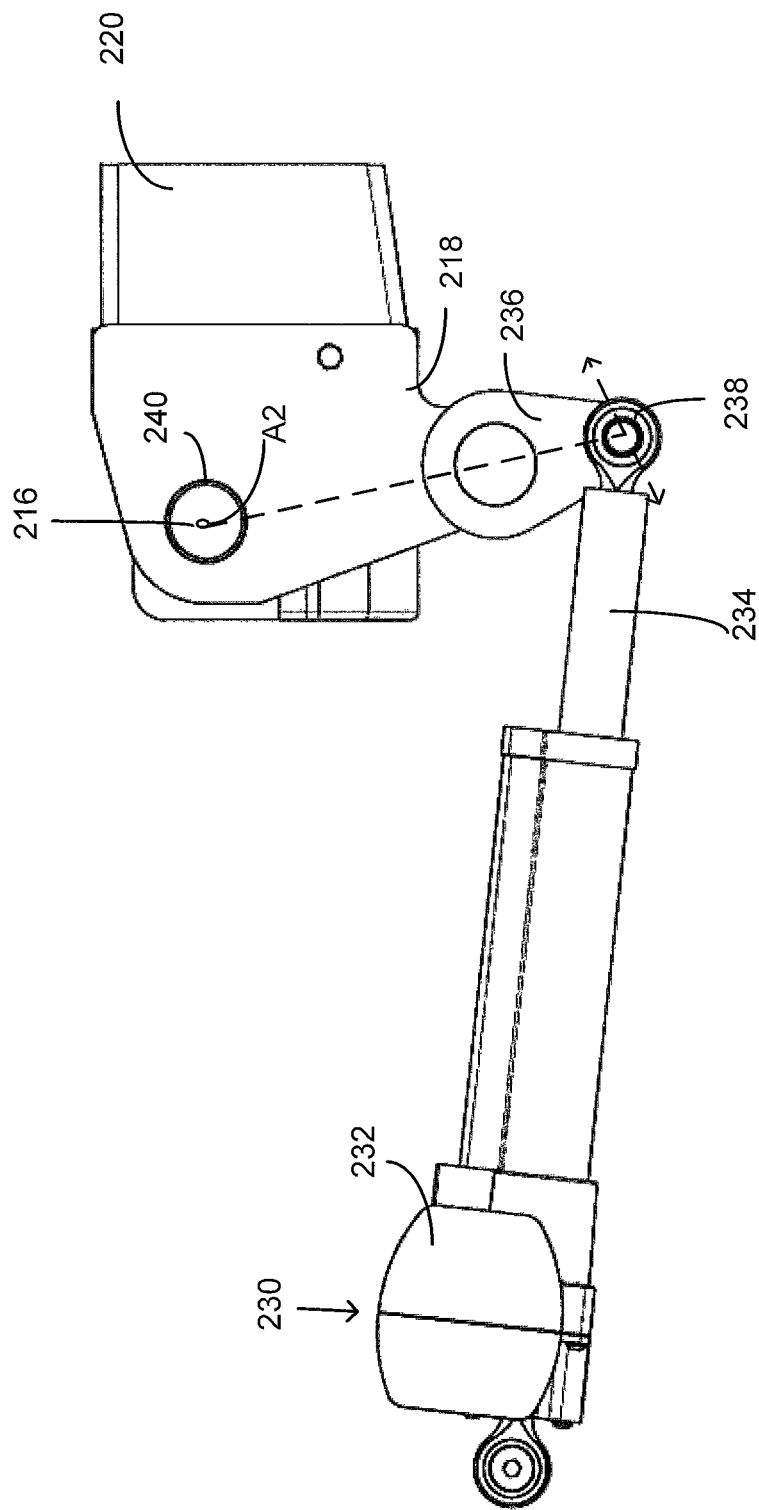
FIG. 21 is a side view of the angulation assembly of FIG. 20.

Referring to FIGS. 20A and 20B, the cross-bar 166 may be a single member, as shown in FIG. 20A, with rounded corners. Or, the cross-bar 166 may include a central member 166 coupled with a pair of shorter members 167 at a coupler 169.

Figure 22:
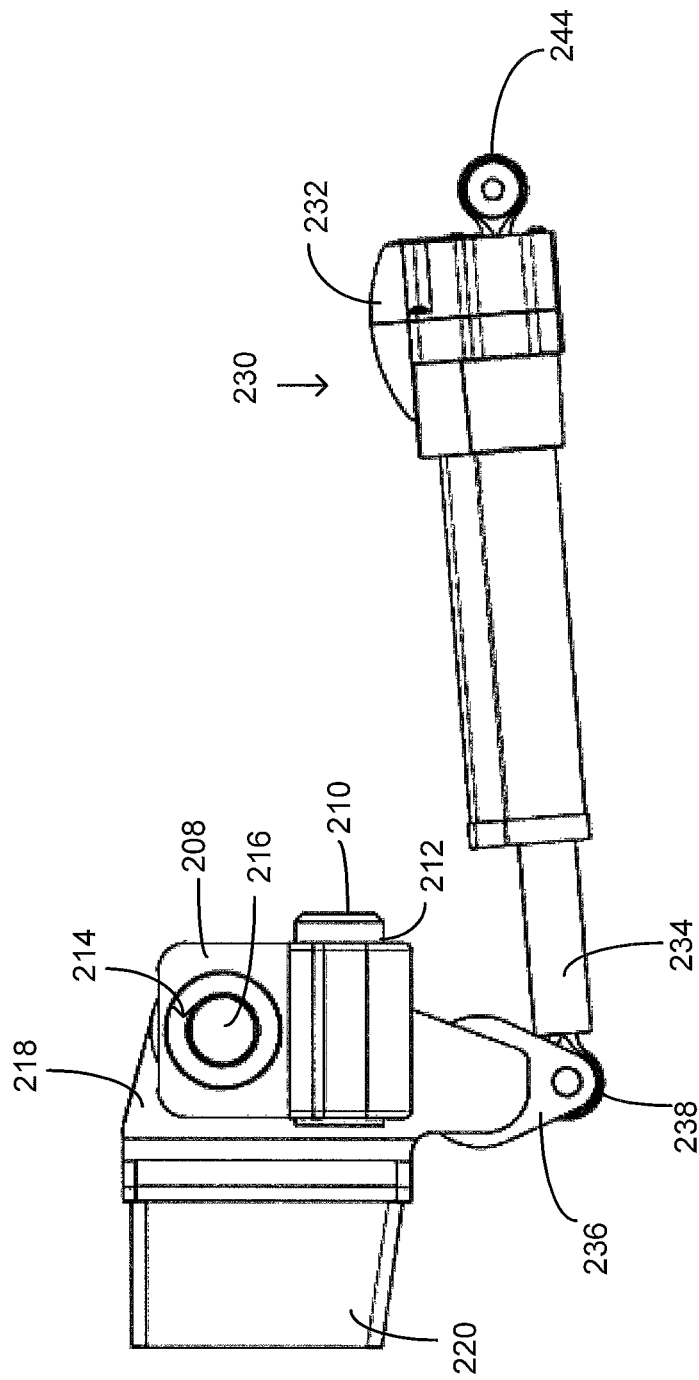
FIG. 22 is an opposite side view of the angulation assembly of FIG. 21.
Figure 23:
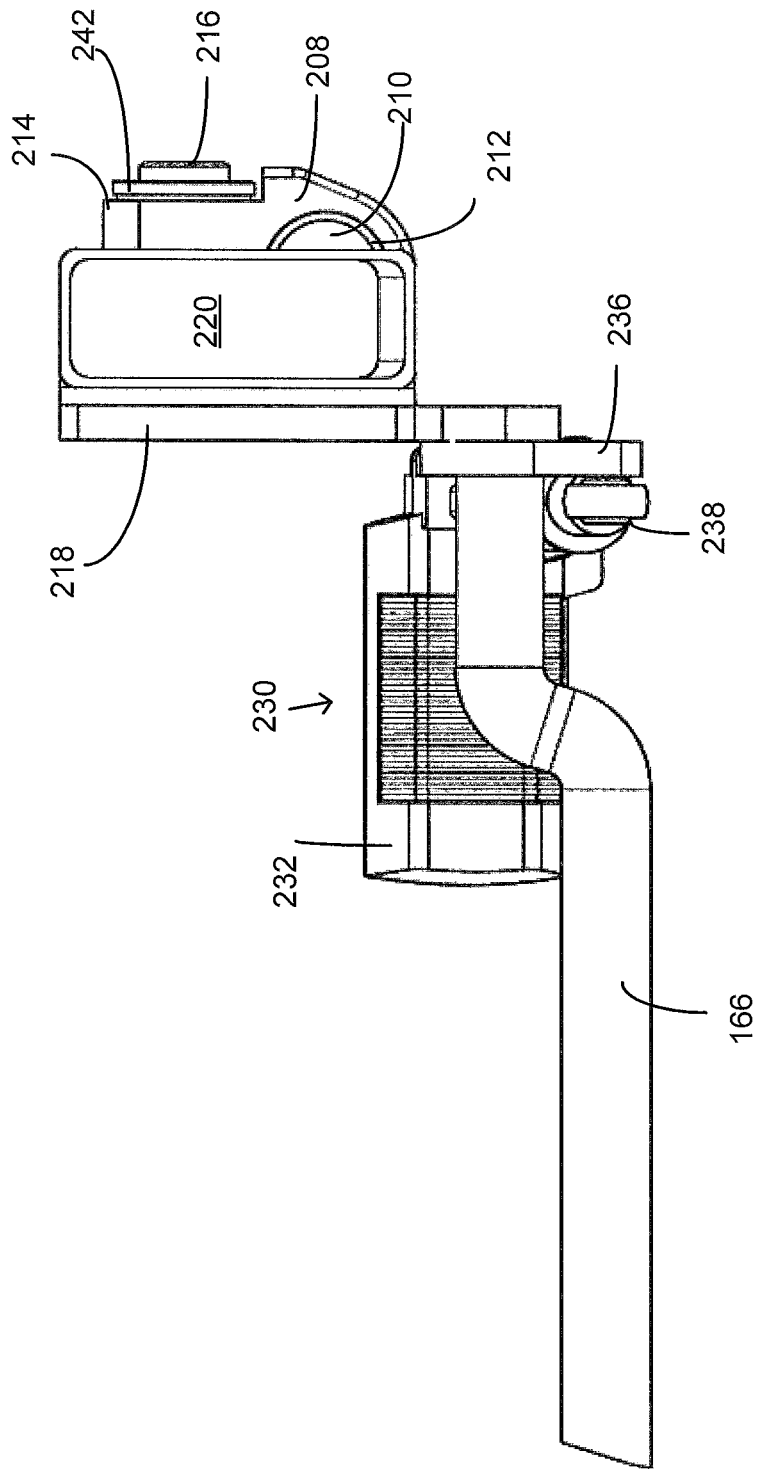
FIG. 23 is a front view of the angulation assembly of FIG. 20.

As seen in FIGS. 19 and 22-23, the cylindrical shaft 216 pivots within a bushing 242 that is fitted within the bore 214 through the multi-axle bearing block 208. In this way, the angulation assemblies 142, 142' are configured to angulate the patient support 104, which causes the cylindrical shaft 216 to rotate within the bushing 242, while maintaining an orientation of the bearing block 208 and not causing the bearing block 208 or the column assemblies 138, 138' to rotate in turn.

It is noted that while the individual assemblies (e.g., lift assemblies 144, 144', angulation assemblies 142, 142') are discussed discretely and often with reference to a single assembly (e.g., lift assembly 144, angulation assembly 142), the assemblies may function together or separately. Additionally, when a single assembly is discussed, it is assumed that the other, opposite assembly functions similarly.

Figure 24:
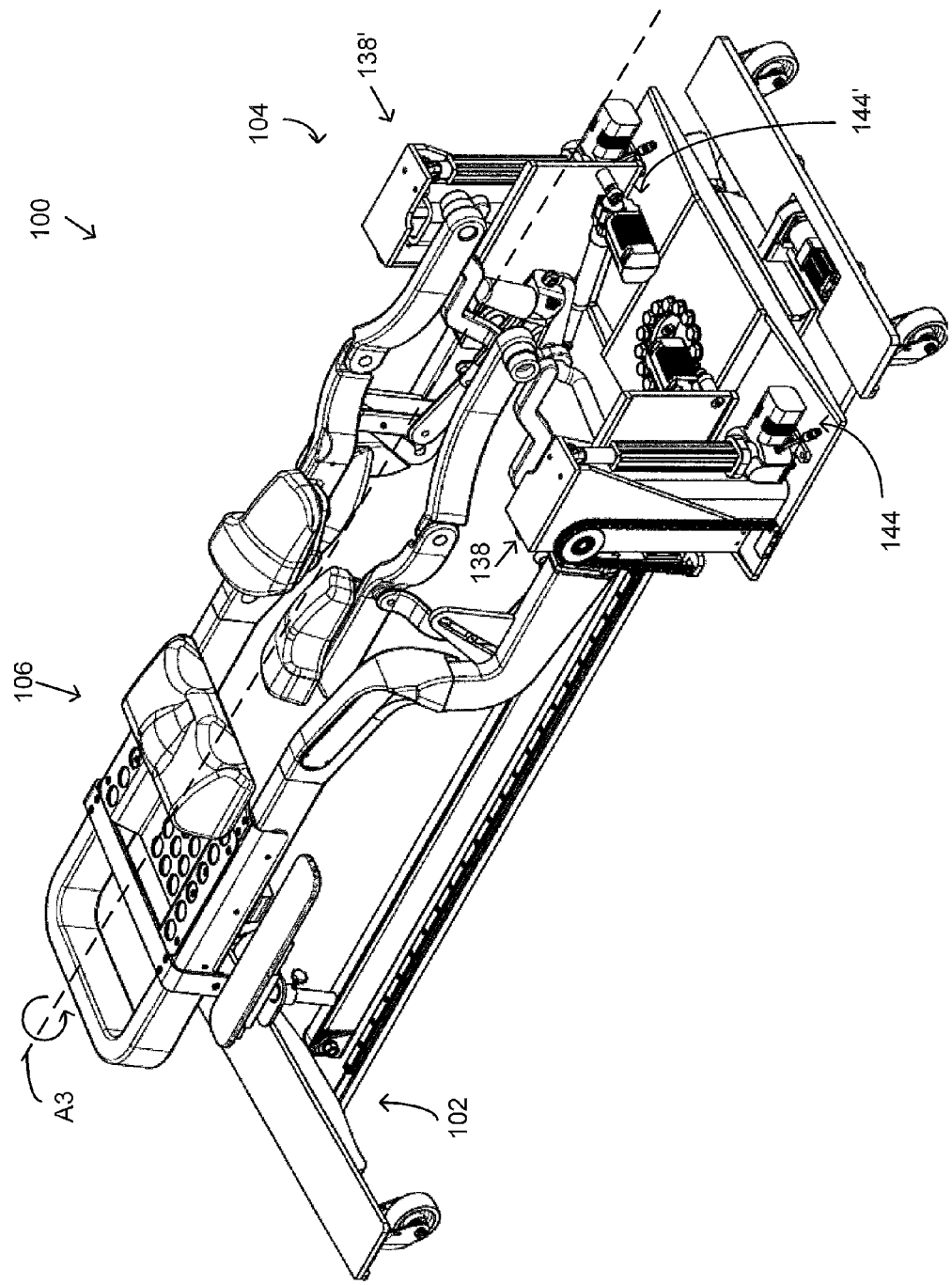
FIG. 24 is an isometric foot end view of the surgical table of FIG. 1 in a rolled position.

Reference is made to FIGS. 24-29, which depict the surgical table 100 and the patient support 106, among other components, in a rolled position. As seen in FIG. 24, the surgical table 100 is configured to position a patient lying in a prone position, for example, in a rolled position relative to a longitudinal axis A3 of the patient support 106. The following figures show the support column 104 with the base 102 and the patient support 106 hidden from view so as to show how the assemblies in the support column 104 facilitate the patient support 106 rolling about the longitudinal axis A3.

Figure 25:
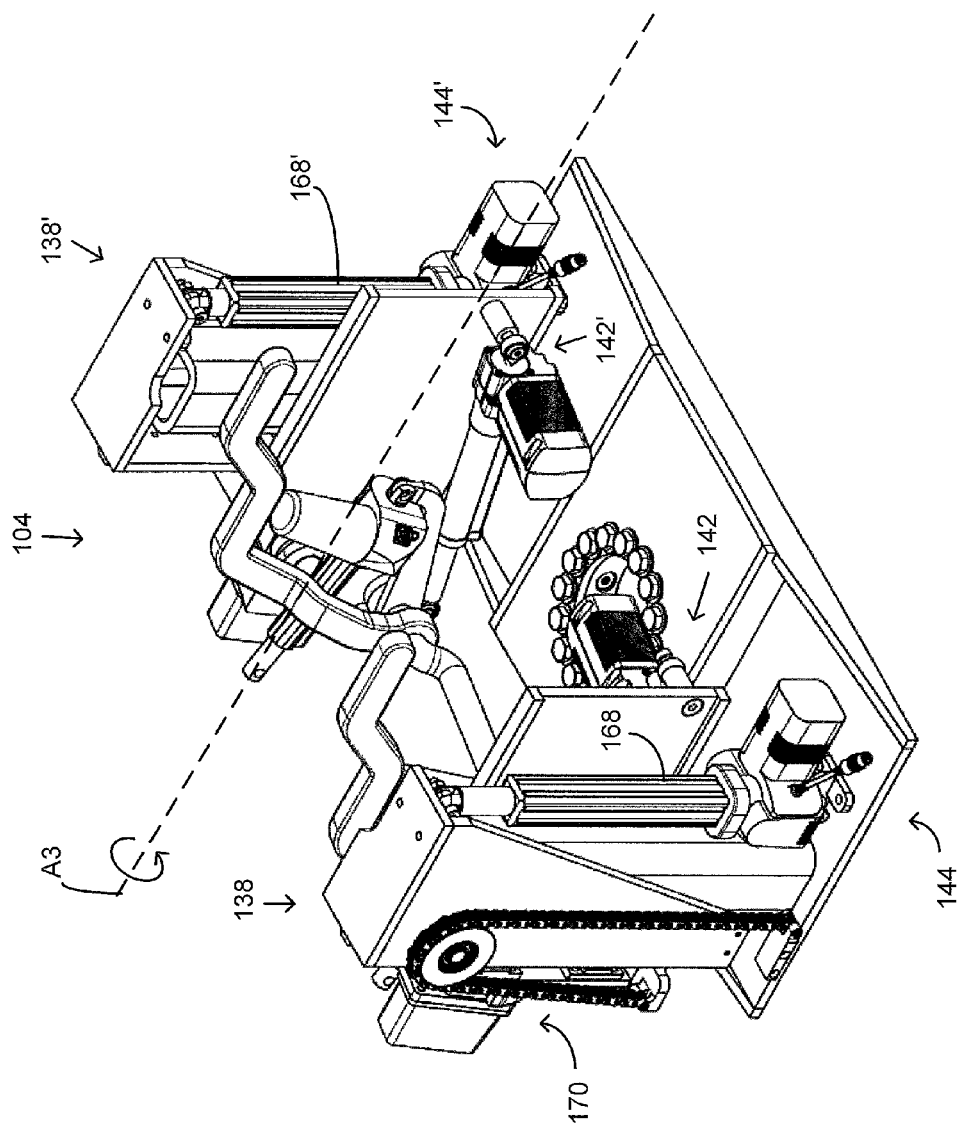
FIG. 25 is an isometric foot end view of the support column of FIG. 1 in a rolled position, with the base assembly and patient support hidden from view.
Figure 26:
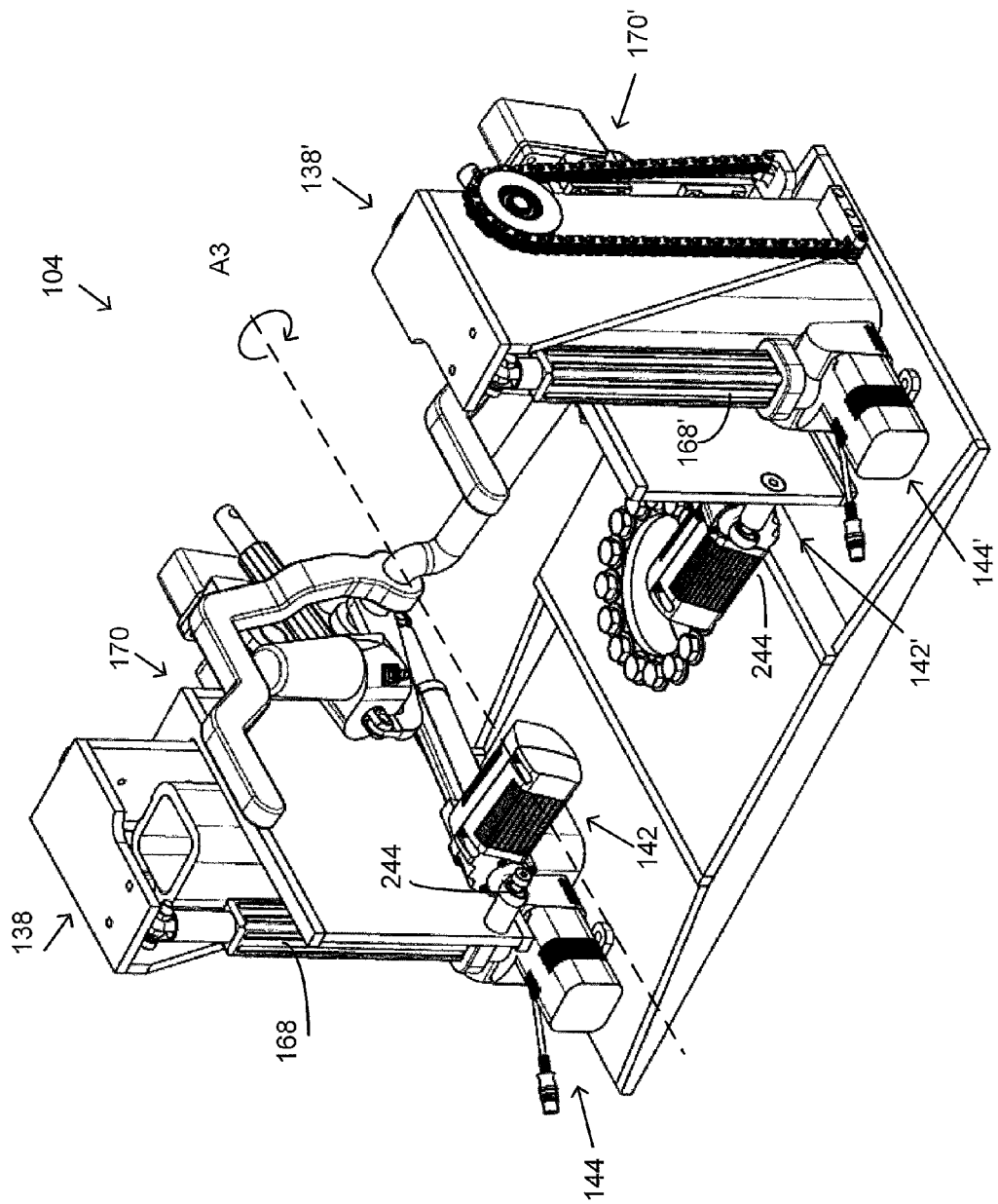
FIG. 26 is another isometric view of the support column in a rolled position.

As illustrated in FIG. 25, which is an isometric view of the support column 104 as viewed from the back of the surgical table, to facilitate the patient support 106 pivoting or rolling about the longitudinal axis A3, one lift assembly 144 is lifted or extended higher than the other lift assembly 144'. In this arrangement, the primary elevator 168 is extended, which causes the secondary elevator 170 to also extend upwards. As seen in FIG. 26, which is another isometric view of the support column 104, the angulation assembly 142, which is coupled to the inner side member 200 of the second housing 196, is also raised upward. The telescoping rod 234 of the linear actuator 230 extends and is coupled to the plate member 236 having the egg-shape via the spherical bearing 238. Since the opposite lift assembly 144' is in a retracted or non-extended state, the cross bar 166 linking the column assemblies 138, 138' is angled relative to the mounting plates 140 and the top surface of the carriage assembly 164.

Figure 27:
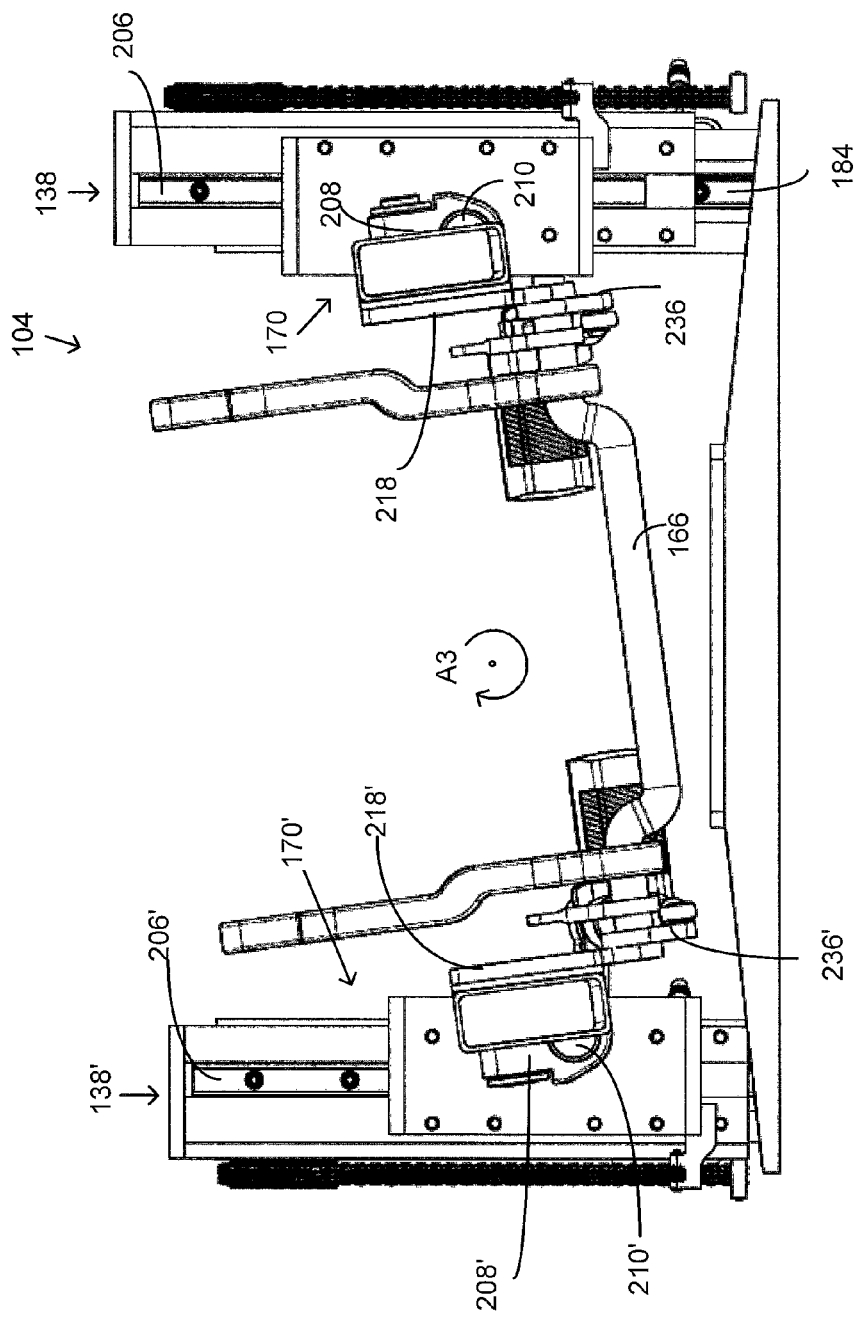
FIG. 27 is a front view of the support column in a rolled position.

As seen in FIG. 27, which is a front view of the support column 104, since the multi-axle bearing blocks 208, 208' are pivotally coupled with the cylindrical shafts 210, 210' and because the cross bar 166 is rigidly coupled between the bearing blocks 208, 208' via the plate members 236, 236', 218, 218', the bearing blocks 208, 208' pivot about their respective cylindrical shafts 210, 210' when the lift assemblies 144, 144' are at different respective heights relative to the mounting plates 140. As seen in the figure, the lift assembly 144 on the right is elevated causing the multi-axle bearing block 208 and, thus, the right side of the patient support 106 to be elevated relative to the opposite, left side of the patient support 106. It is noted that the linear actuators 230, 230' of the angulation assemblies 142, 142' pivot or rotate along with the angling of the cross bar 188. That is, the linear actuators 230, 230' do not maintain a constant orientation relative to the mounting plates 140; rather, the linear actuators 230, 230' are raised and lowed with movement of the primary and secondary elevators 168, 170, and the linear actuators 230, 230' pivot along with the bearing block 208 in response to rolling of the patient support 106. The linear actuators 230, 230' are able to pivot along with the bearing blocks 208, 208' because they are coupled with the inner side members, 200, 200' of the second housing 196, 196' via a spherical bearing 244, as shown in FIGS. 25-26, which allows for such multi-axle pivoting.

Figure 28:
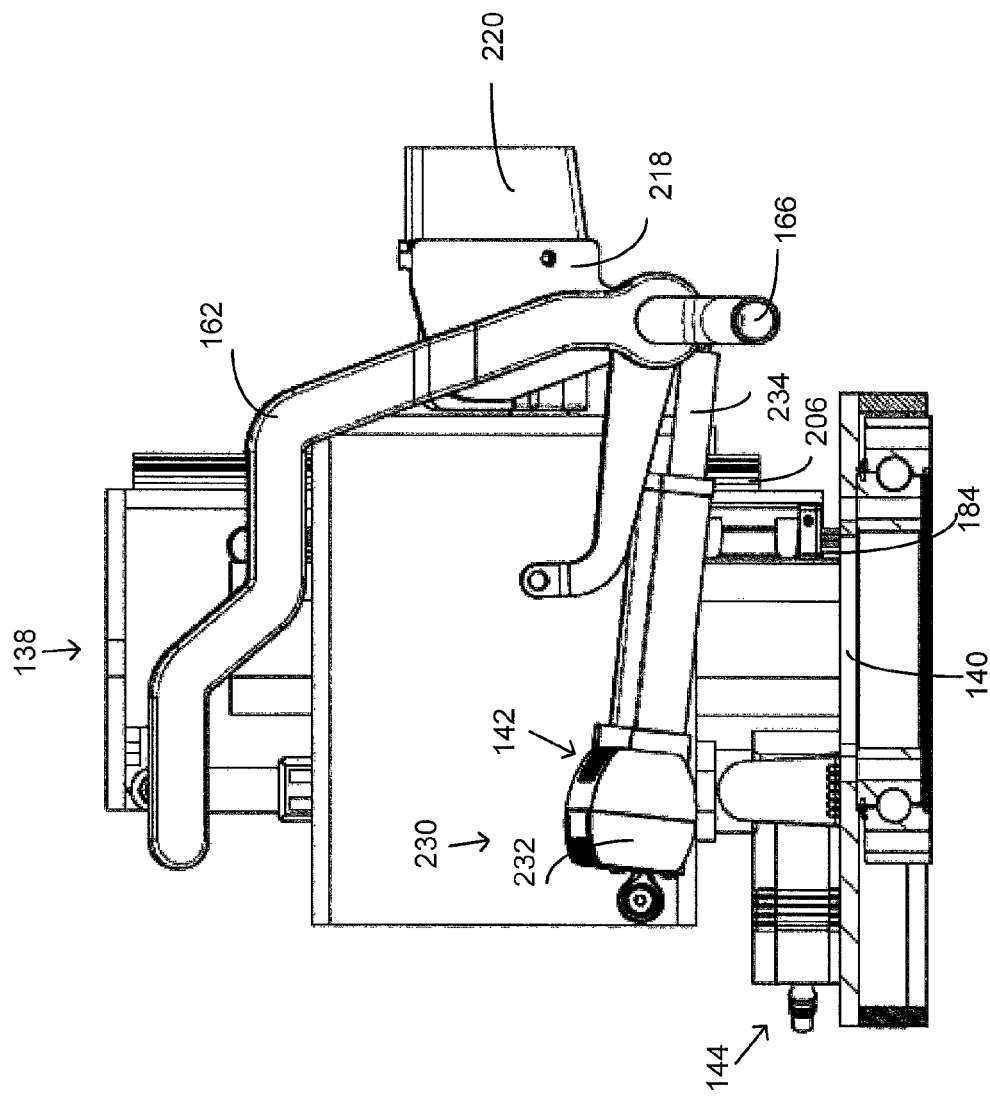
FIG. 28 is a cross sectional side view of one of the column assemblies in a rolled position.
Figure 29:
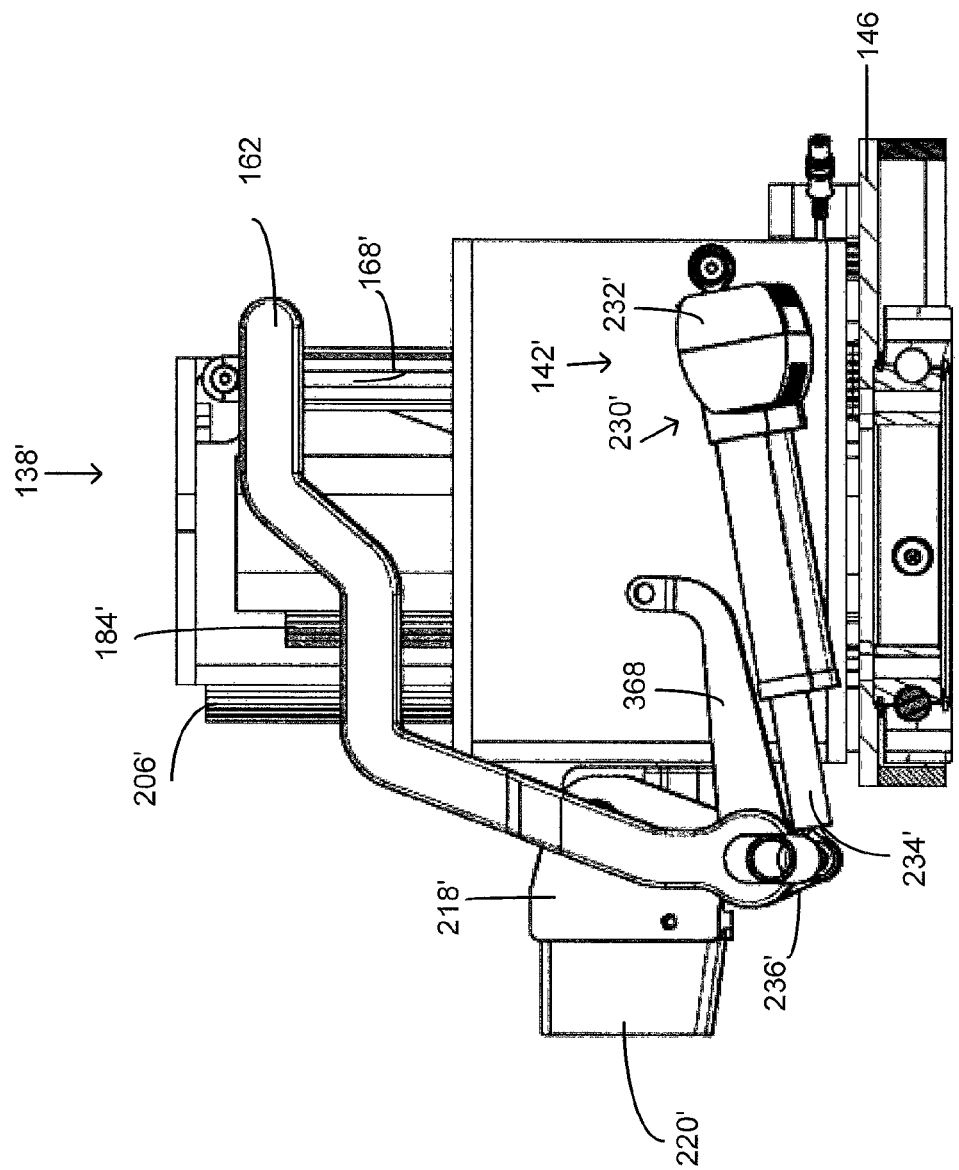
FIG. 29 is a cross sectional side view of the other column assembly in a rolled position.

Turning to FIGS. 28-29, which are side cross-sectional views of the column assemblies 138, 138', while the lift assemblies 144, 144' are at different elevations relative to the mounting plates 140, the angulation assemblies 142, 142' are in a neutral position. That is, the angulation assemblies 142, 142', which are responsible for angulating the patient support 106 (not shown) upwards and downwards (i.e., reverse Trendelenburg, Trendelenburg), are positioned to angle the longitudinal axis A3 of the patient support 106 generally parallel with the floor, as seen in FIG. 24. The angulation assemblies 142, 142', however, could angle the patient support 106 upwards or downwards while still maintaining the patient support 106 in the rolled position. To do this, the linear actuators 230, 230' would extend the telescoping rod 234, 234' to position the patient support upward (i.e., reverse Trendelenburg), which would pivot the plate members 218, 218', 236, 236' about the cylindrical shaft 216, 216' within the bearing block 208, 208' and cause the patient support plug 220 and, thus, the patient support 106 to be raised or angled upward. To angle the patient support downward (i.e., Trendelenburg), the linear actuators 230, 230' would retract the telescoping rod 234, 234', which would pivot the plate members 218, 218', 236, 236' about the cylindrical shaft 216, 216' within the bearing block 208, 208' and cause the patient support plug 220 and, thus, the patient support 106 to be lowered or angled downward.

Figure 31:
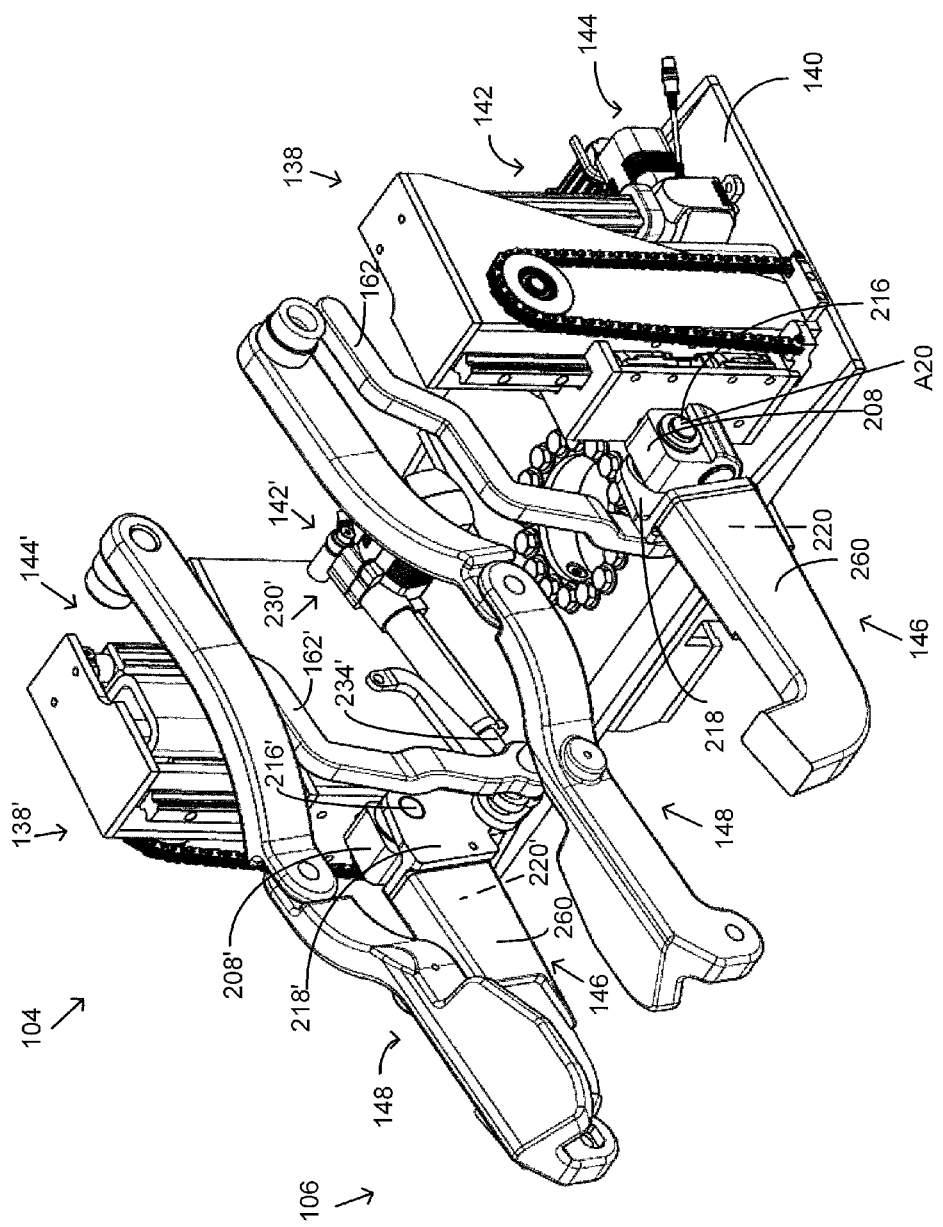
FIG. 31 is an isometric view of the support column and a portion of the patient support angling the patient support towards the floor.
Figure 32:
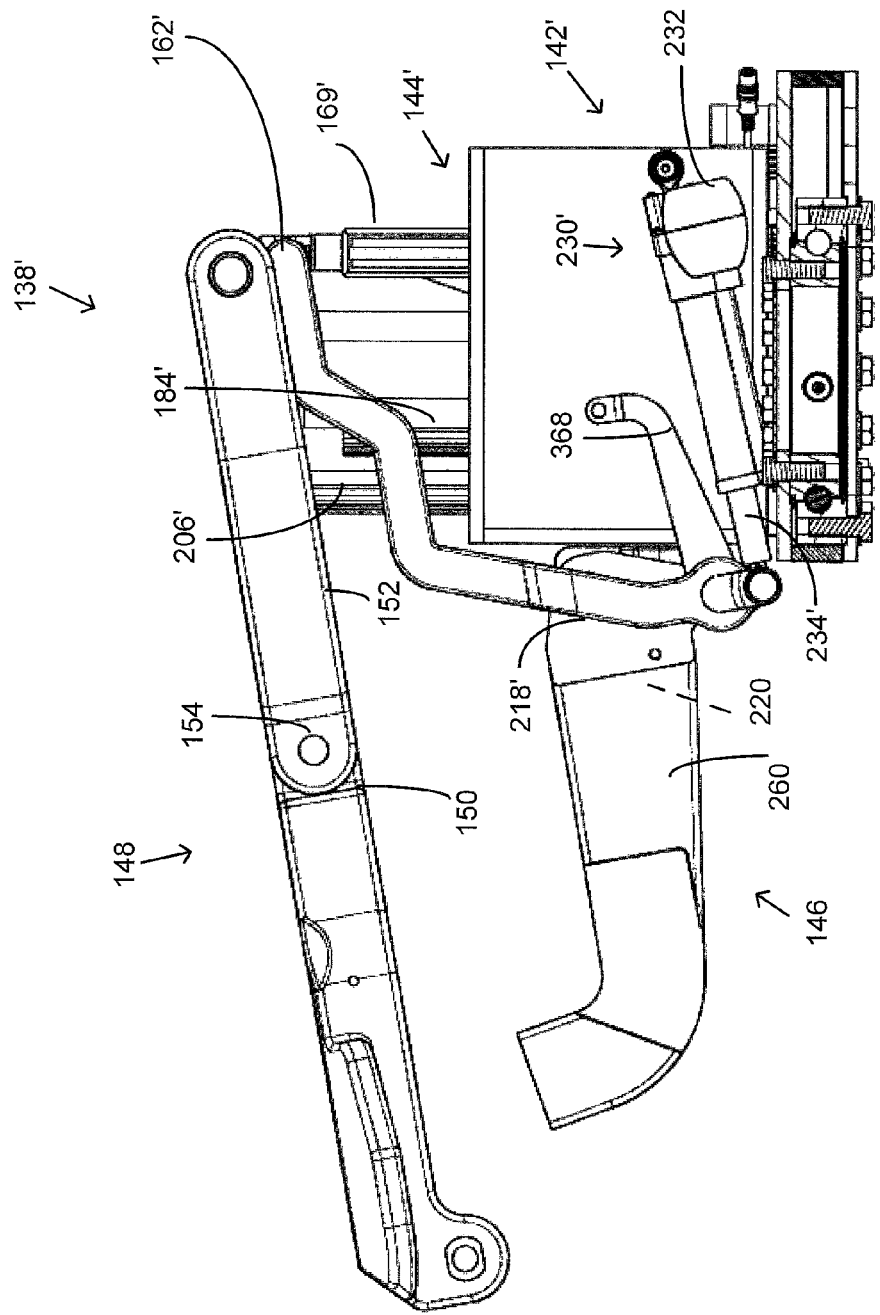
FIG. 32 is a side view of the support column angling the patient support towards the floor.
Figure 33:
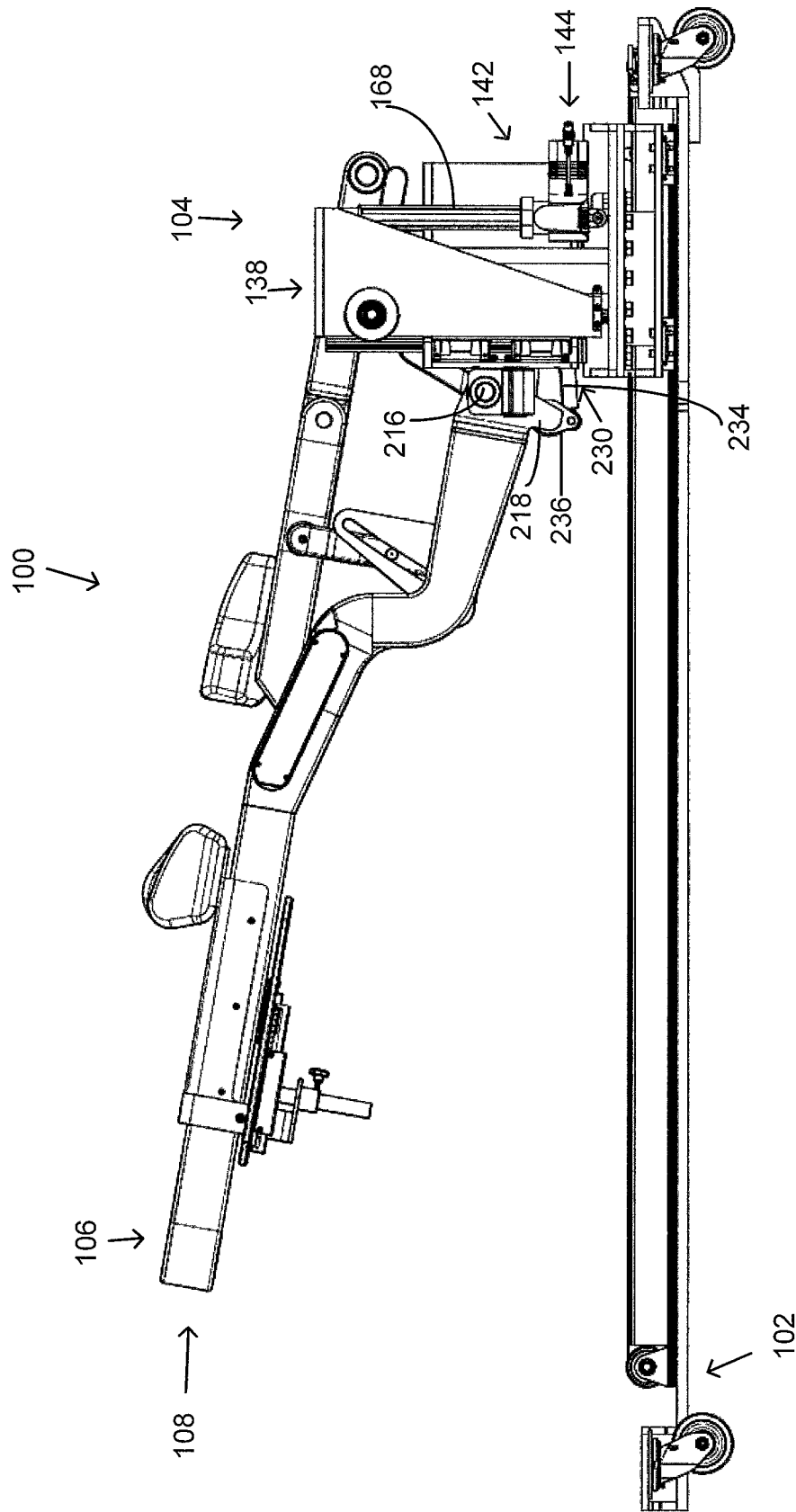
FIG. 33 is a side view of the surgical table of FIG. 1 with the head end of the patient support angled upwards away from the floor.
Figure 34:
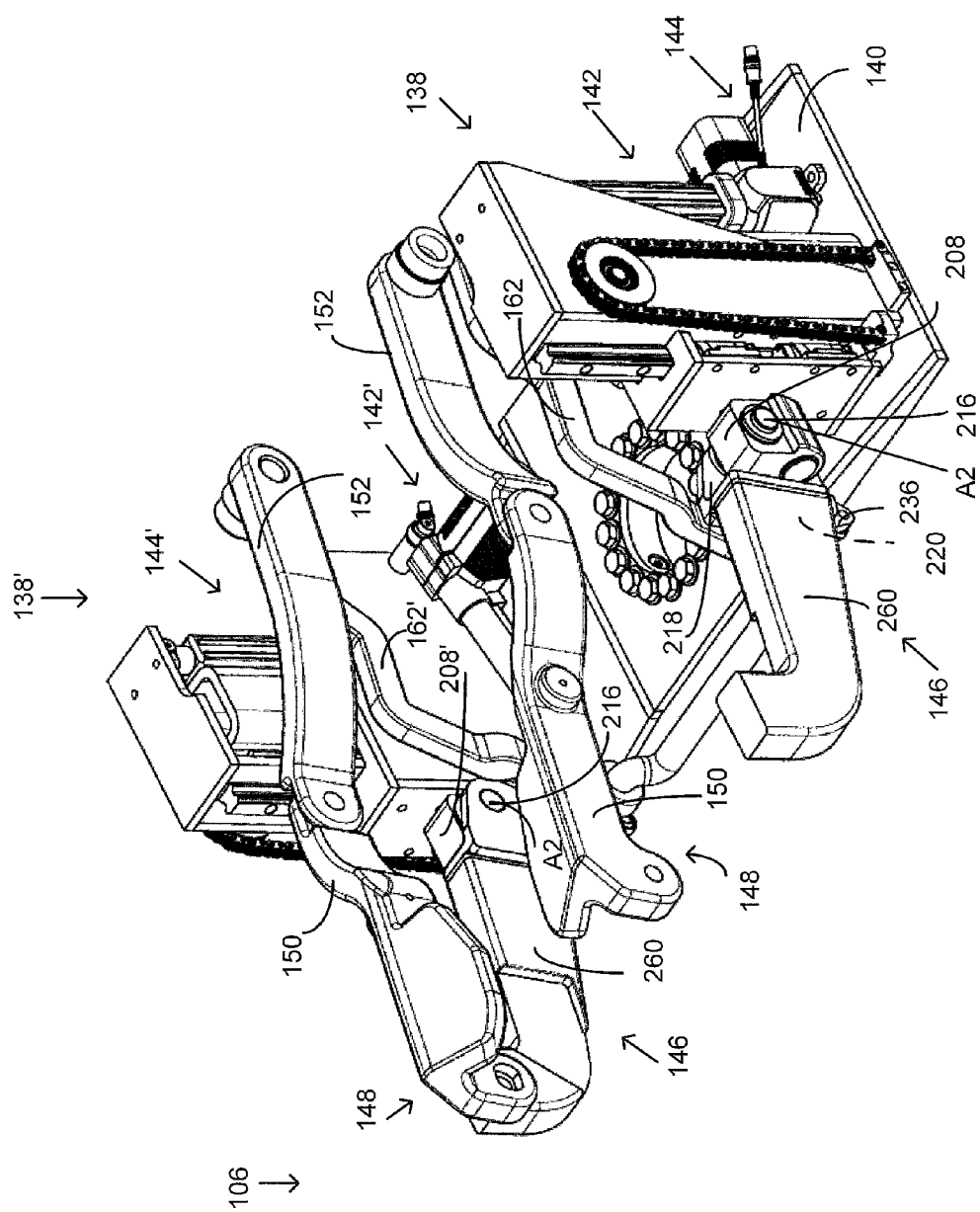
FIG. 34 is an isometric view of the support column and a portion of the patient support angling the patient support upwards away from the floor.
Figure 35:
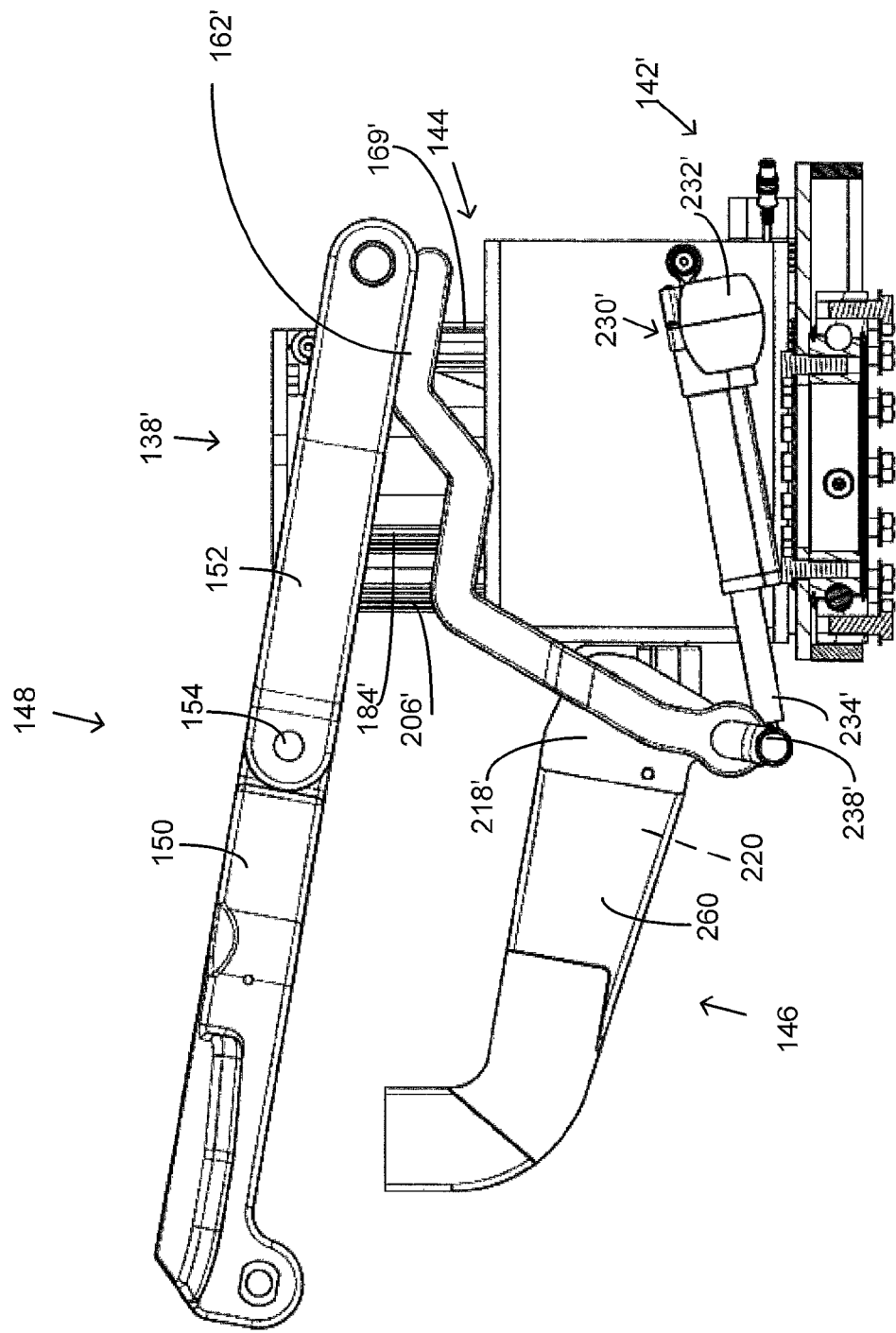
FIG. 35 is a side view of the support column angling the patient support upwards away from the floor.

Reference is now made to FIGS. 30-35, which depict the surgical table 100 in various angled orientations so as to position a patient positioned on the patient support 106 in a prone position in Trendelenburg (FIGS. 30-32) and in reverse Trendelenburg (FIGS. 33-35).

Figure 30:
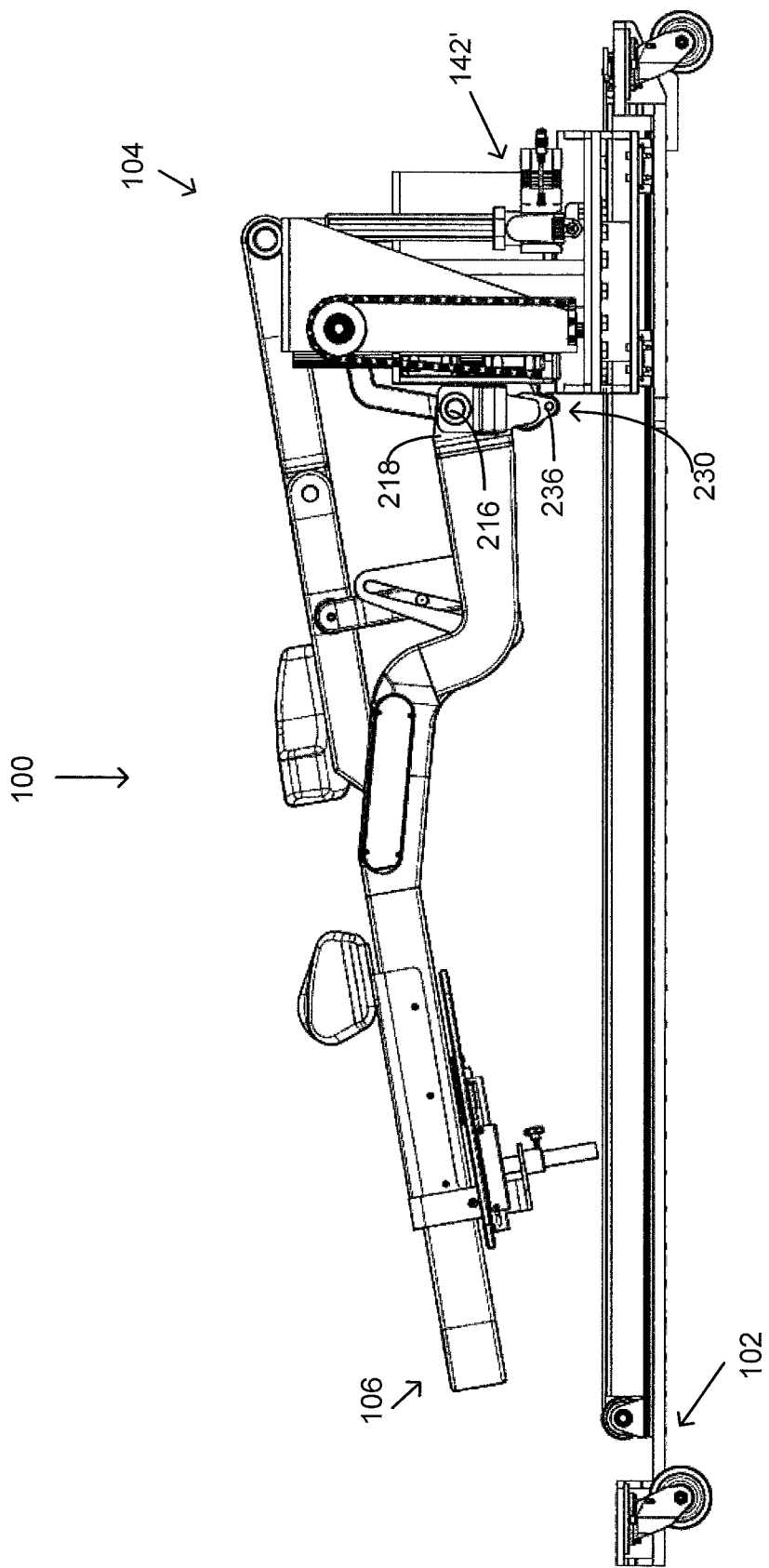
FIG. 30 is a side view of the surgical table of FIG. 1 with the head end of the patient support angled towards the floor.

As seen in FIG. 30, the surgical table 100 is angled downward at a head end 108 of the patient support 106 to position a patient lying in a prone position in Trendelenburg. To facilitate this positioning, as seen in FIGS. 30-32, the linear actuators 230, 230' of the angulation assemblies 142, 142' retract the telescoping rod 234, 234'. As seen in FIG. 32, as the telescoping rod 234' is retracted, the plate members 218', 236' rotate counterclockwise about the central axis A2 of the cylindrical shaft 216. This rotation, in turn, causes the patient support plug 220, which is coupled with the foot end section 260 of the rigid frame 146, to angle head end 108 of the patient support 106 downward towards the floor (i.e., Trendelenburg).

As seen in FIG. 33, the surgical table 100 is angled upward at the head end 108 of the patient support 106 to position a patient lying in a prone position in reverse Trendelenburg. To facilitate this positioning, as seen in FIGS. 33-35, the linear actuators 230, 230' of the angulation assemblies 142, 142' extend the telescoping rod 234, 234'. As seen in FIG. 35, as the telescoping rod 234' is extended, the plate members 218', 236' rotate clockwise about the central axis A2 of the cylindrical shaft 216. This rotation, in turn, causes the patient support plug 220 to angle the head end 108 of the patient support 106 upwards and away from the floor (i.e., reverse Trendelenburg). As seen in FIGS. 31 and 34, the foot end 110 of the patient support 106 remains supported on the guide member 162' during angling of the patient support 106 in Trendelenburg and reverse Trendelenburg.

C. The Patient Platform

Figure 36:
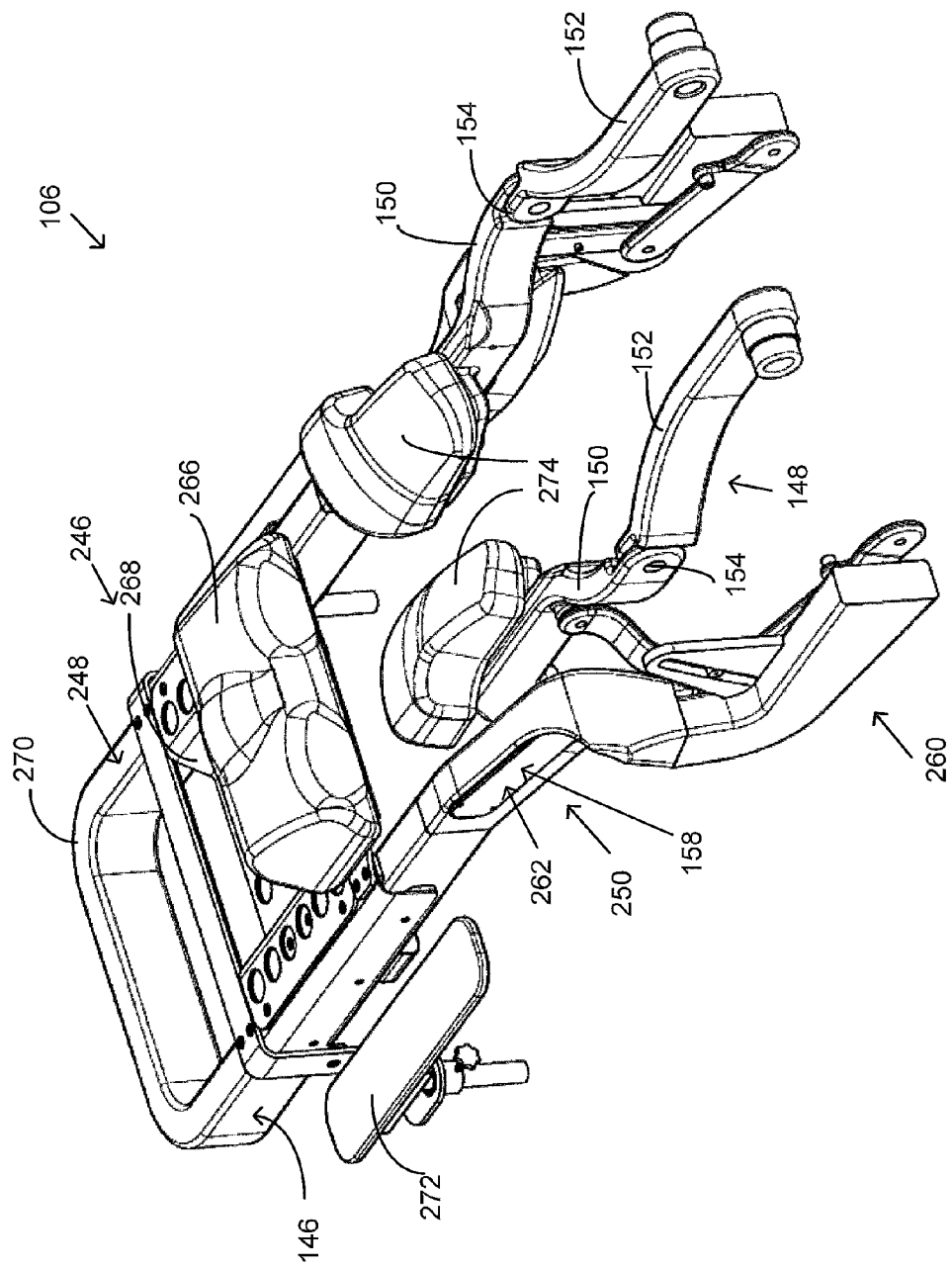
FIG. 36 is an isometric foot end view of the patient support in a neutral position.
Figure 50:
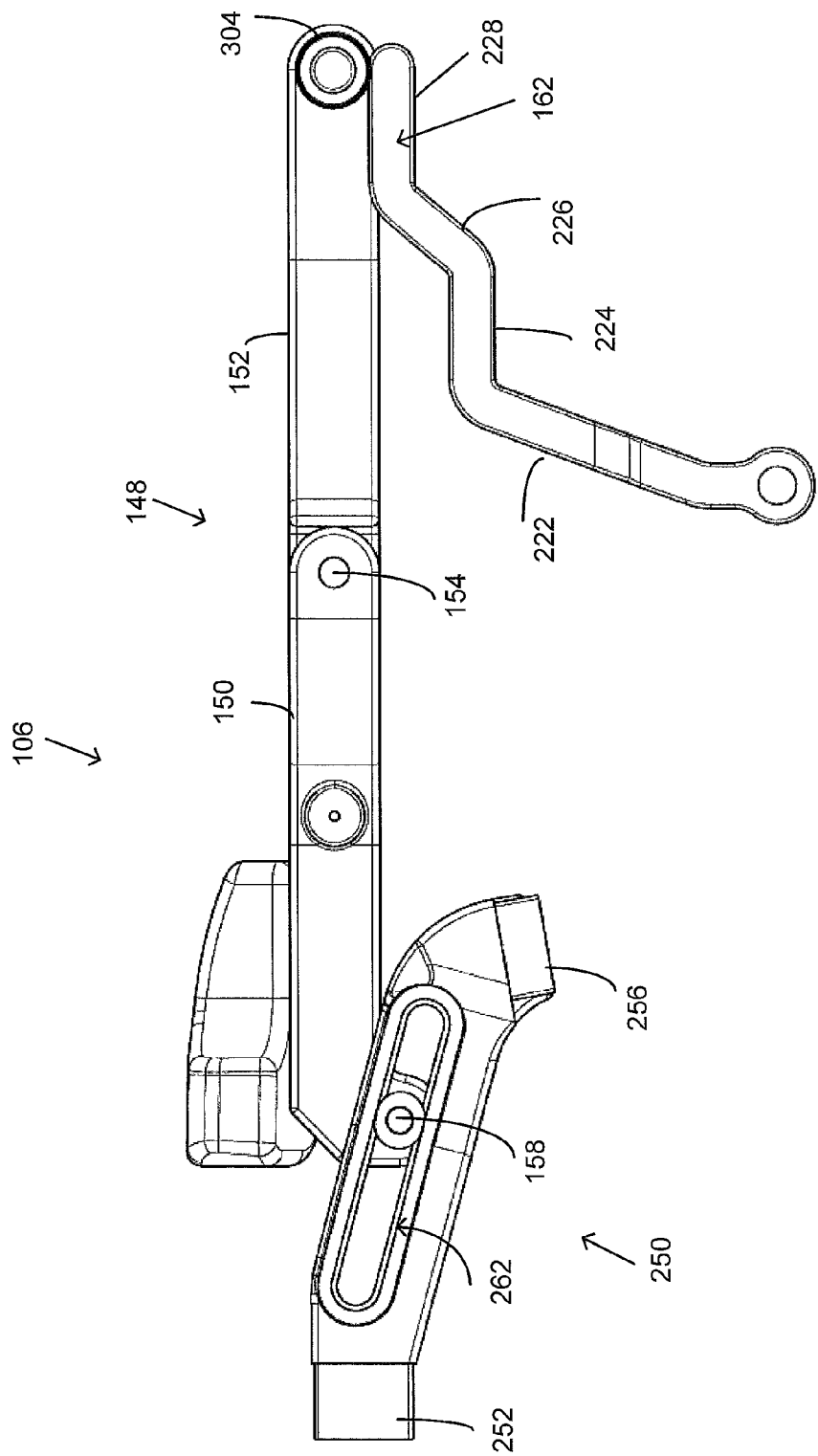
FIG. 50 is a side view of the inner frame in an unarticulated state, the middle section of the rigid frame, and the guide member.
Figure 51:
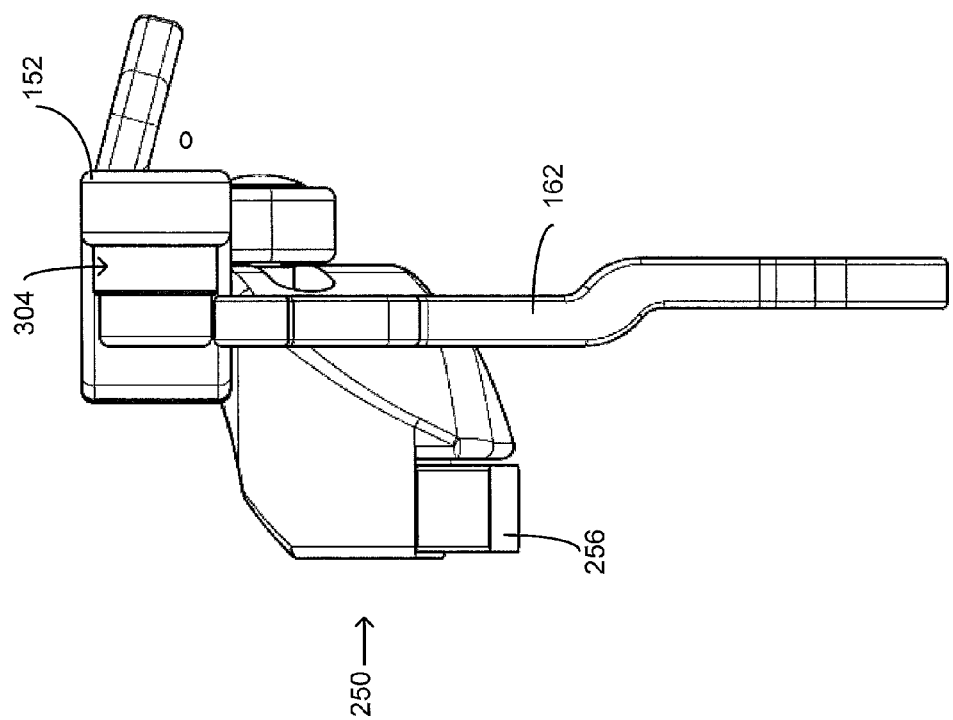
FIG. 51 is a back view of the components of FIG. 50.
Figure 52:
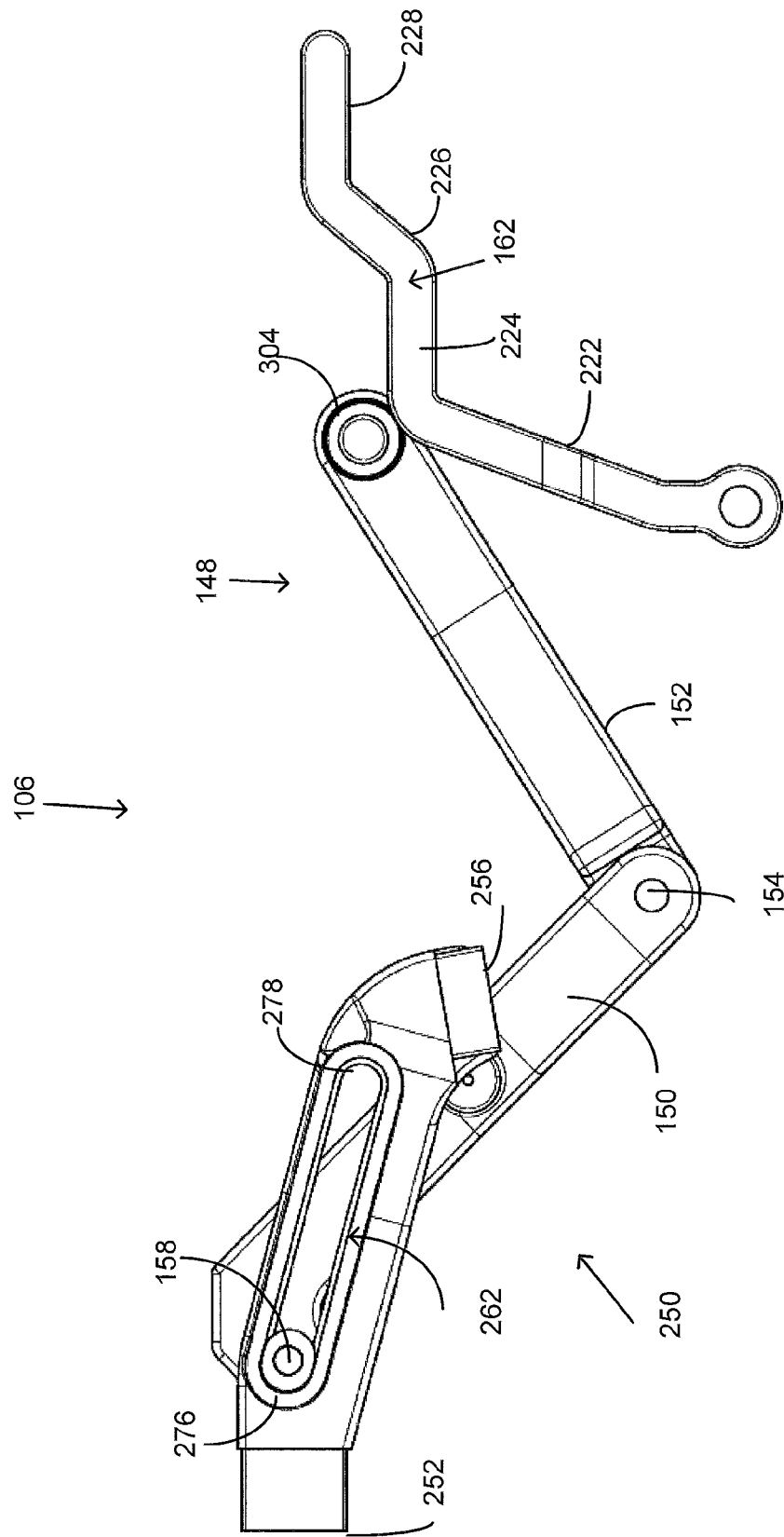
FIG. 52 is a side view of the inner frame articulated in flexion, the middle section of the rigid frame, and the guide member.

Reference is now made to FIGS. 36-63, which depict various views of the patient support 106 and its respective componentry. As seen in FIG. 36, the patient support is in a neutral position (i.e., not in flexion or extension). In this orientation, the rigid outer frame 146 and the articulating inner frame 148 are generally parallel to each other and configured to position a patient in a prone position with the illustrated configuration of supporting pads. A different configuration of the pads may facilitate a supine position, among others. As seen in the figure, a torso assembly 246 is slidingly positioned on a head end section 248 of the patient support 106. The head end section 248 is a U-shaped member 270 of the patient support 106 that is may be constructed of a hollow, four-sided radiolucent material (i.e., transparent to x-ray) (e.g., carbon fiber, PEEK, polymer, composite). The head end section 248 extends forward from and slidingly couples with a middle section 250 of the rigid outer frame 146. As seen in FIGS. 50-52, the middle section 250 includes male end plugs 252 at a head end of the middle section 250 that friction fit into corresponding female ends 254 of the head end section 248 of the U-shaped member 270. On the foot end, the middle section 250 includes male end plugs 256 that friction fit into corresponding female ends 258 of a foot end section 260 of the rigid outer frame 146. The foot end section 260 includes a four-sided angled member with a female end 264 that friction fits with a male end of the patient support plug 220.

Referring back to FIG. 36, the middle section 250 includes a slot 262 to guide the translating and pivoting hinge 158 as the inner frame 148 moves from neutral to flexion and extension, etc. The middle section 250 may also be made of a radiolucent material, such as, for example, carbon fiber, PEEK, composite, or the like. The foot end section 260 extends rearwardly from the middle section 250 and may be constructed of a radiolucent material.

Figure 37:
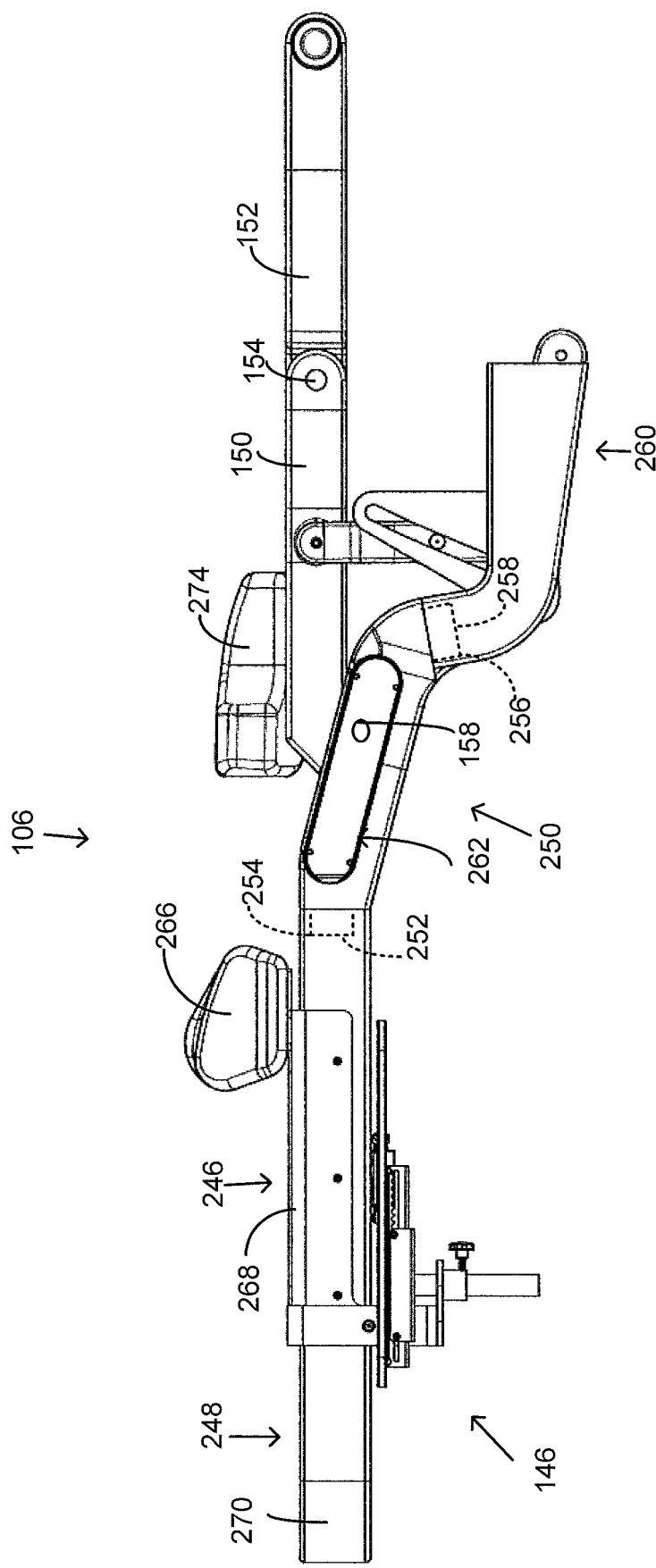
FIG. 37 is a side view of the patient support in a neutral position.
Figure 38:
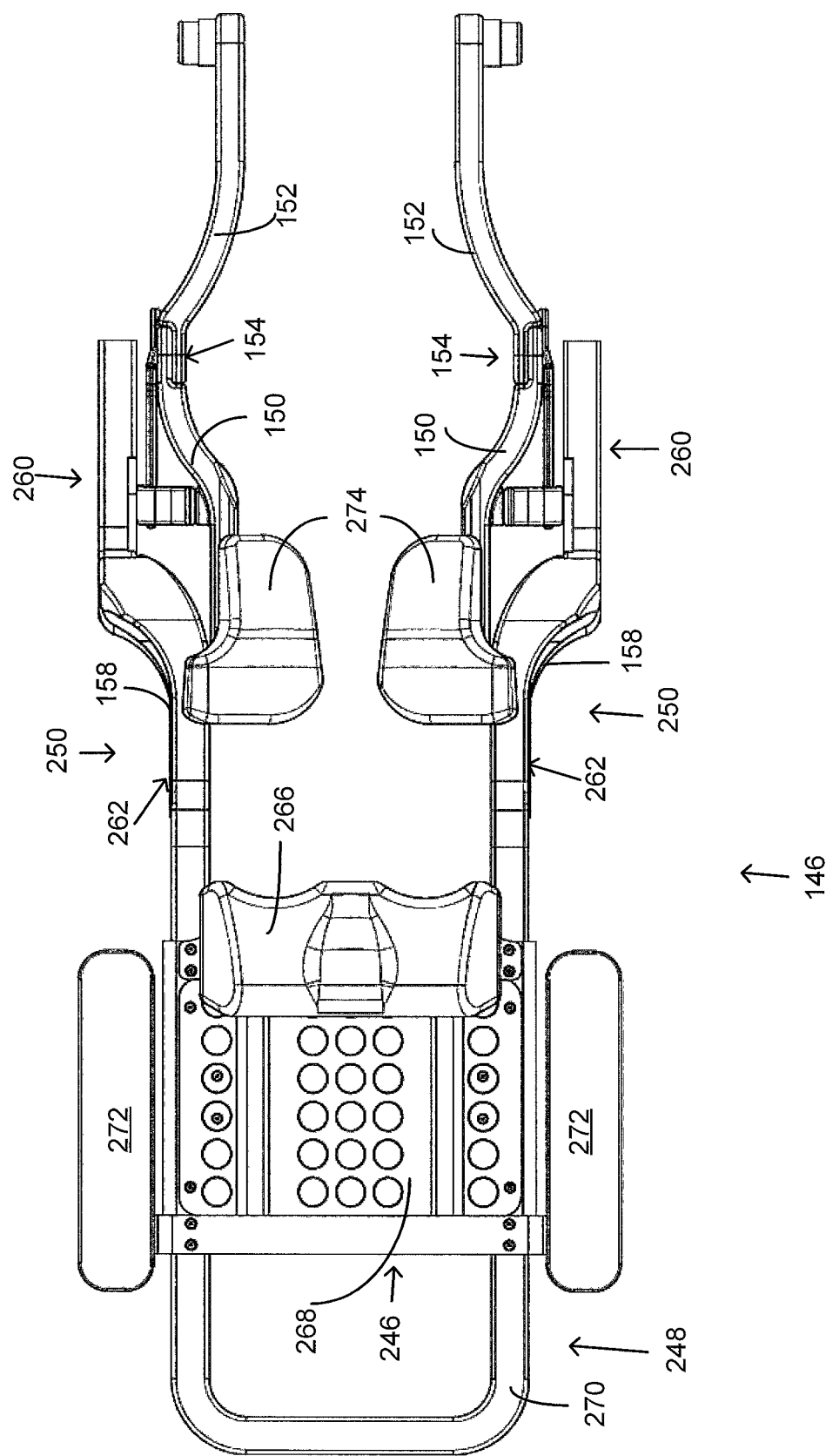
FIG. 38 is a top view of the patient support in a neutral position.

Referring still to FIGS. 36-38, the torso assembly 246 includes a chest pad 266 positionable on a platform 268 that spans across the open frame of the head end section 248. The platform 268 is positionable on opposite portions of the U-shaped member 270 and is securable in a particular position by a clamp or lock. As mentioned previously, the torso assembly 246 remains in a fixed position during articulating of the inner frame 148 and does not translate along the U-shaped member 270 once it is locked in place. The torso assembly 246 further includes a pair of arm supports 272, which are also adjustable and lockable. To support the patient's lower body, the inner frame 148 includes a pair of hip pads 274 positioned generally above the hinge 158. The torso assembly 246 and the hip pads are removeable and may be substituted for other pads and supports known in the art.

Figure 39:
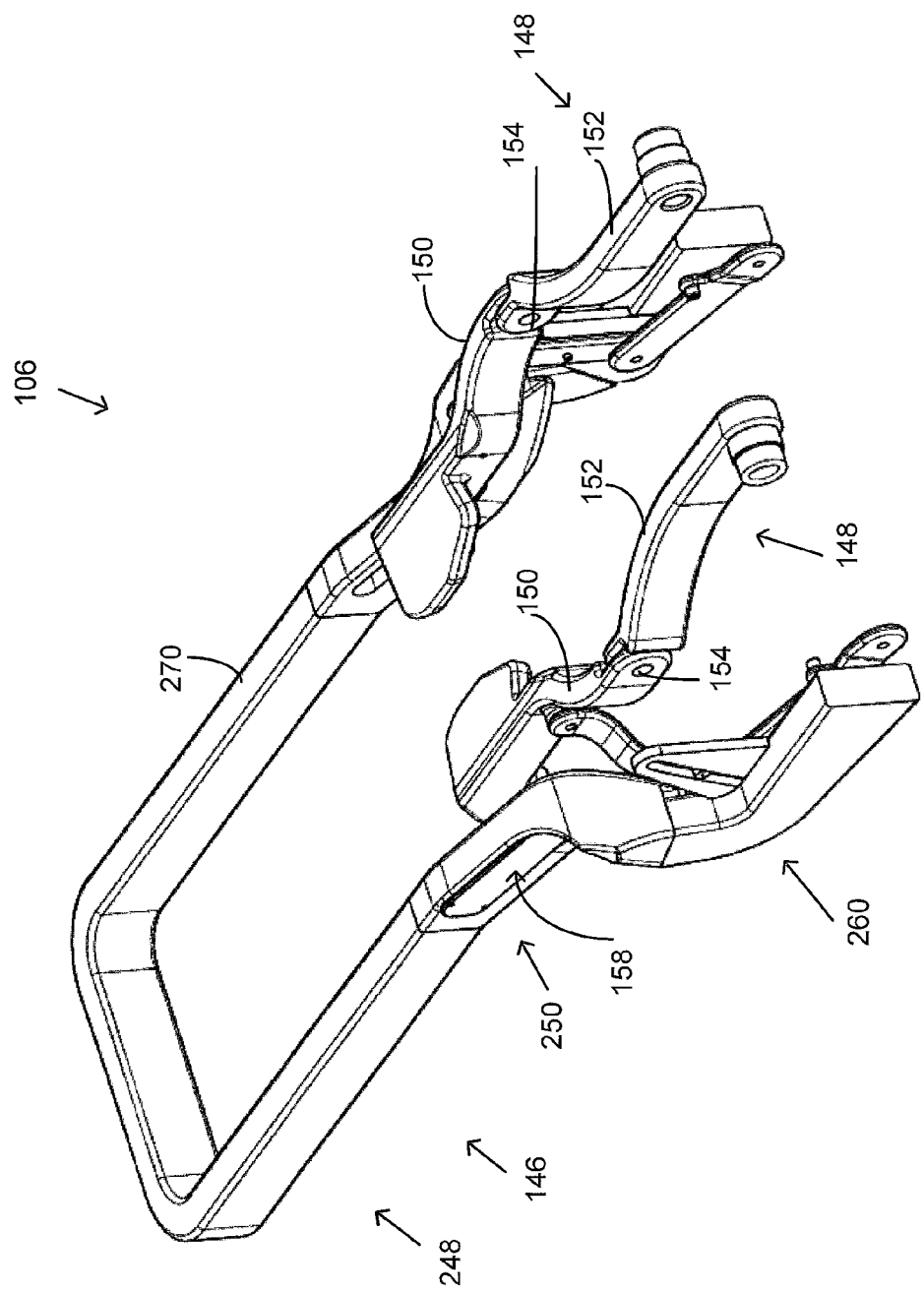
FIG. 39 is an isometric foot end view of the patient support in a neutral position with the pads and torso assembly removed.
Figure 40:
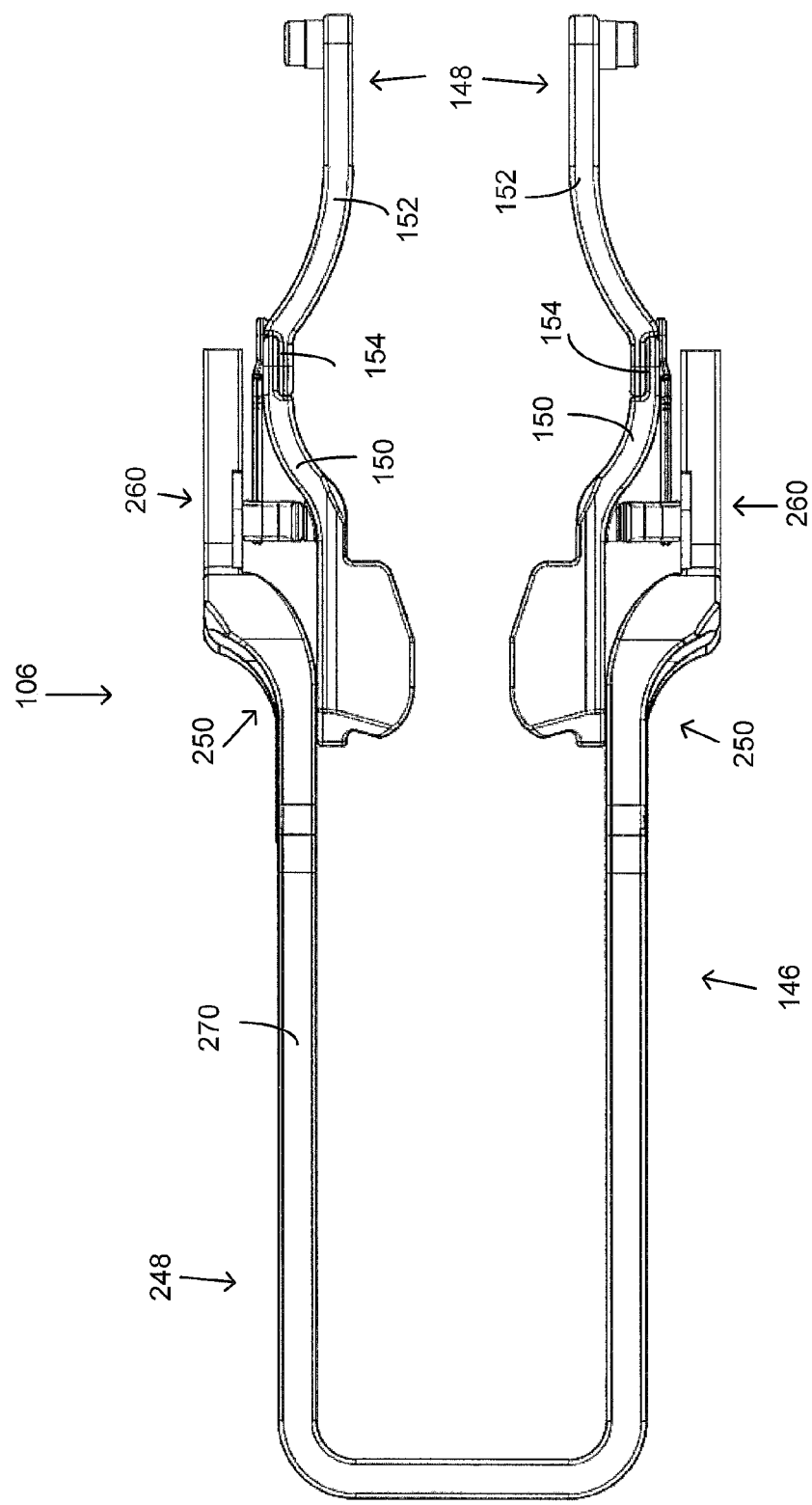
FIG. 40 is a top view of the patient support in a neutral position with the pads and torso assembly removed.
Figure 41:
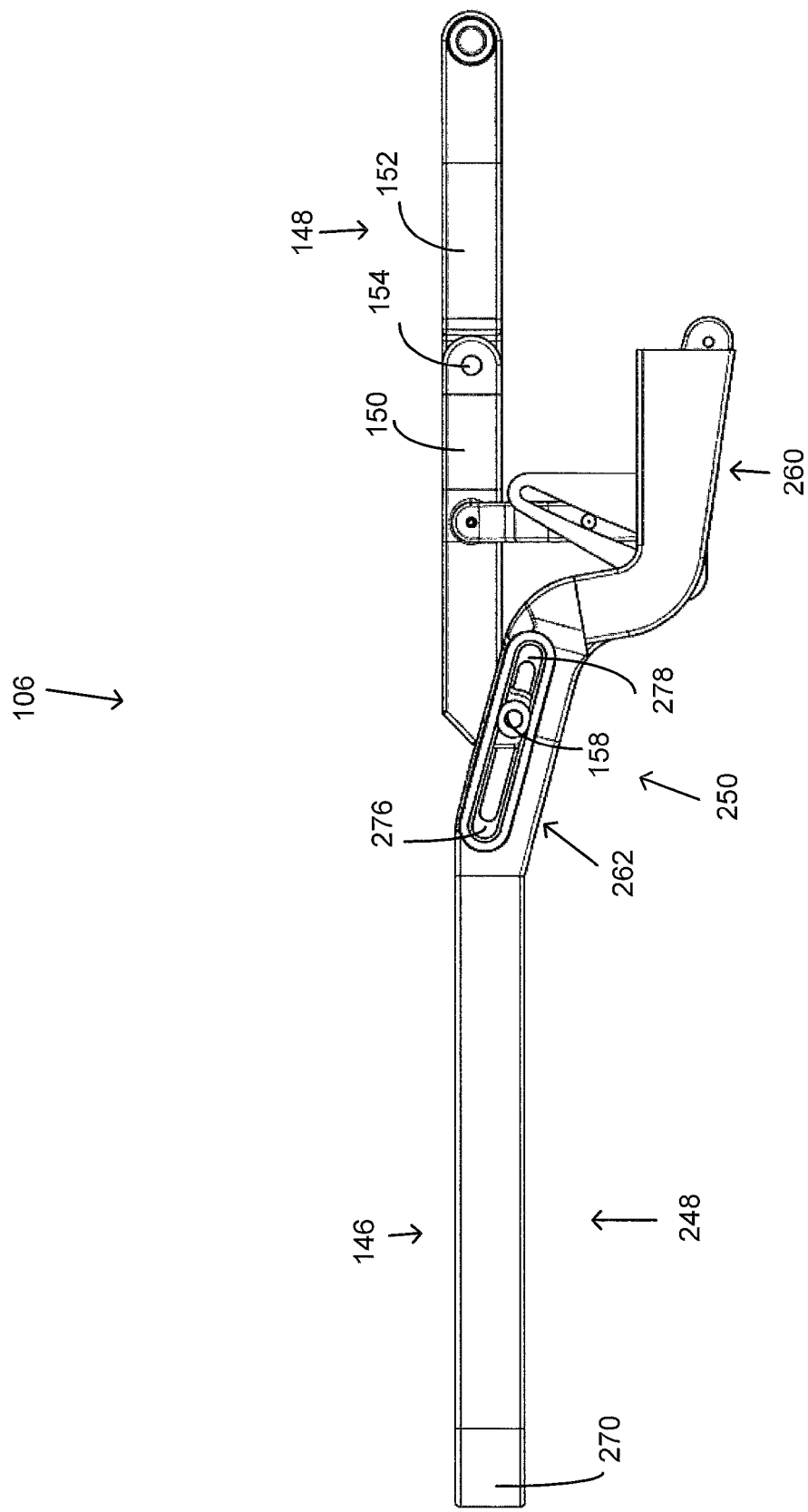
FIG. 41 is a side view of the patient support in a neutral position with the pads and torso assembly removed.
Figure 42:
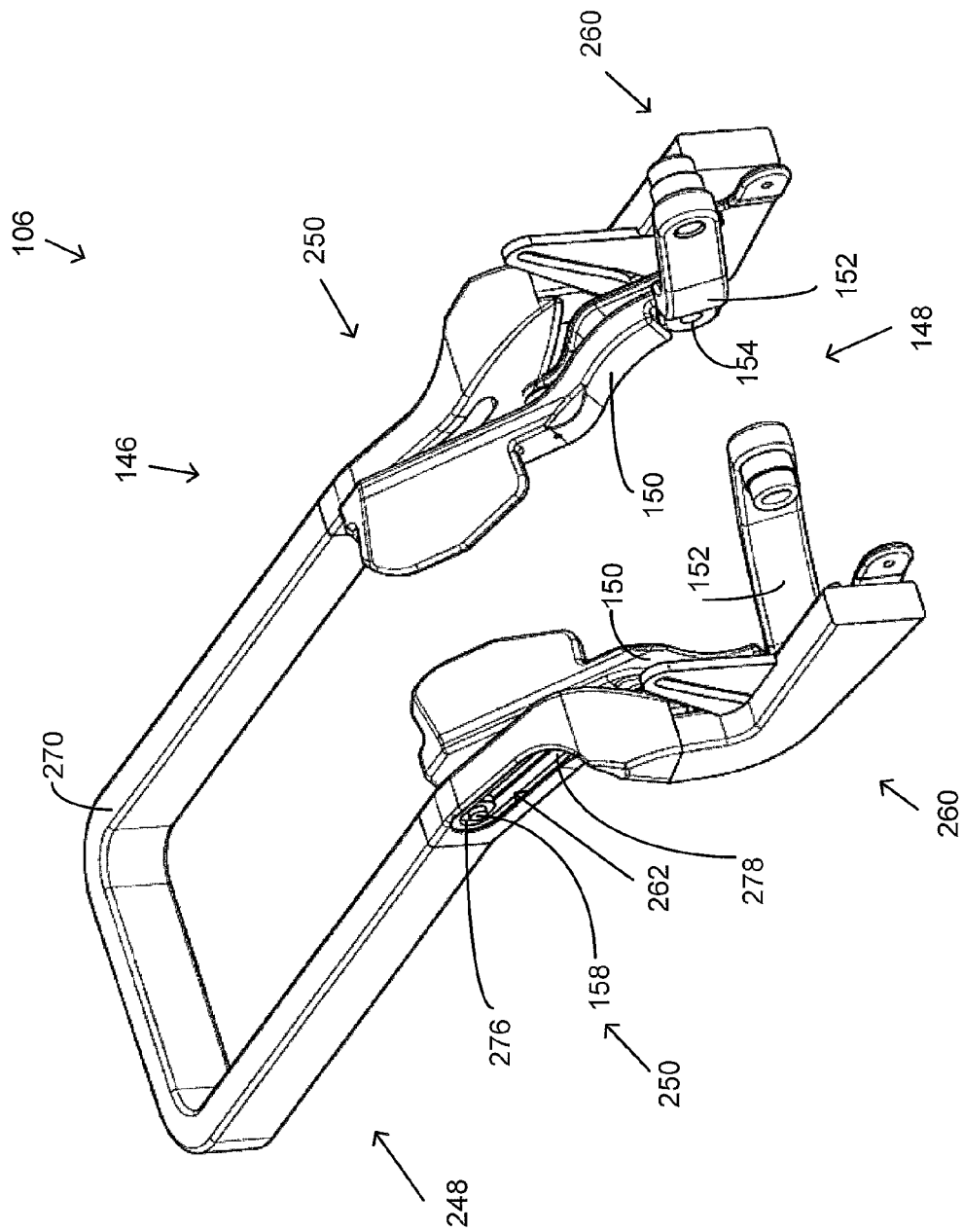
FIG. 42 is an isometric foot end view of the patient support in a flexed position with the pads and torso assembly removed.
Figure 43:
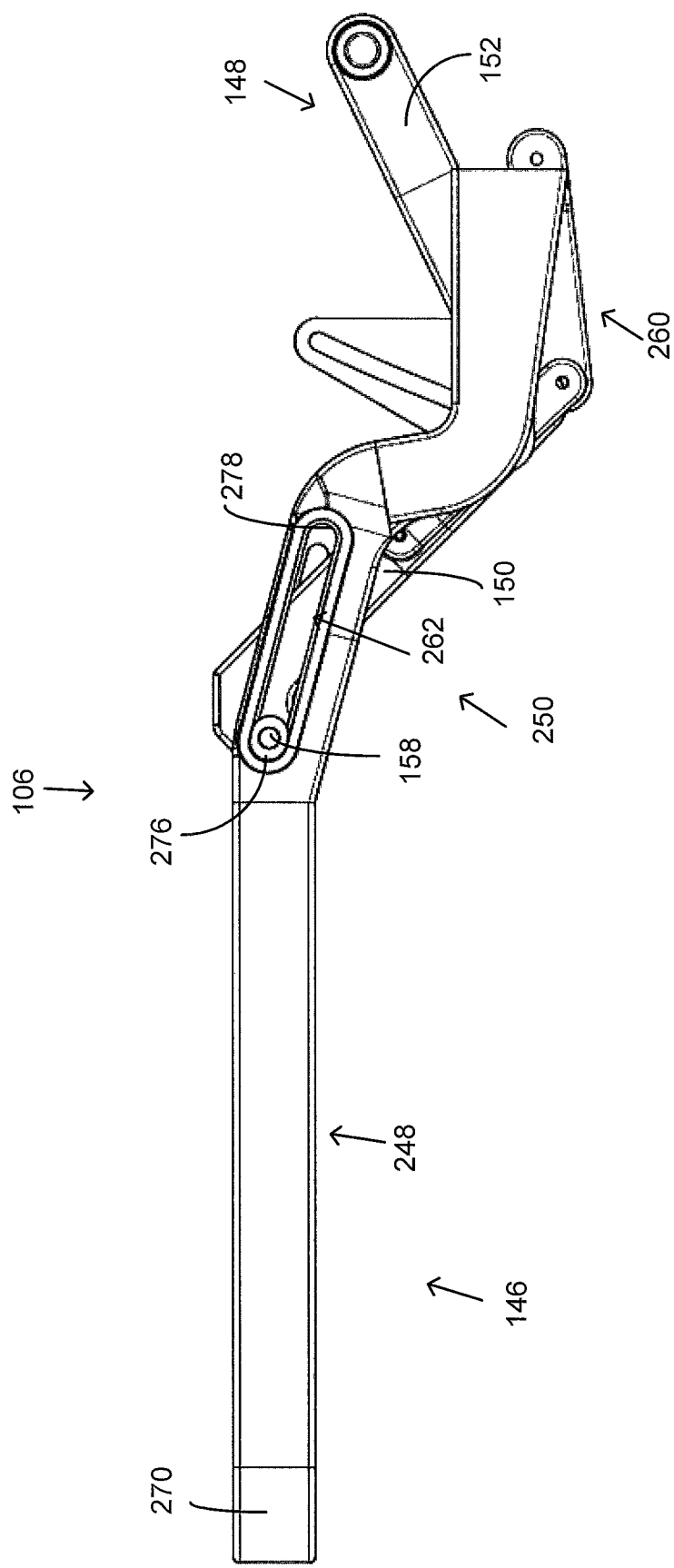
FIG. 43 is a side view of the patient support in a flexed position with the pads and torso assembly removed.
Figure 44:
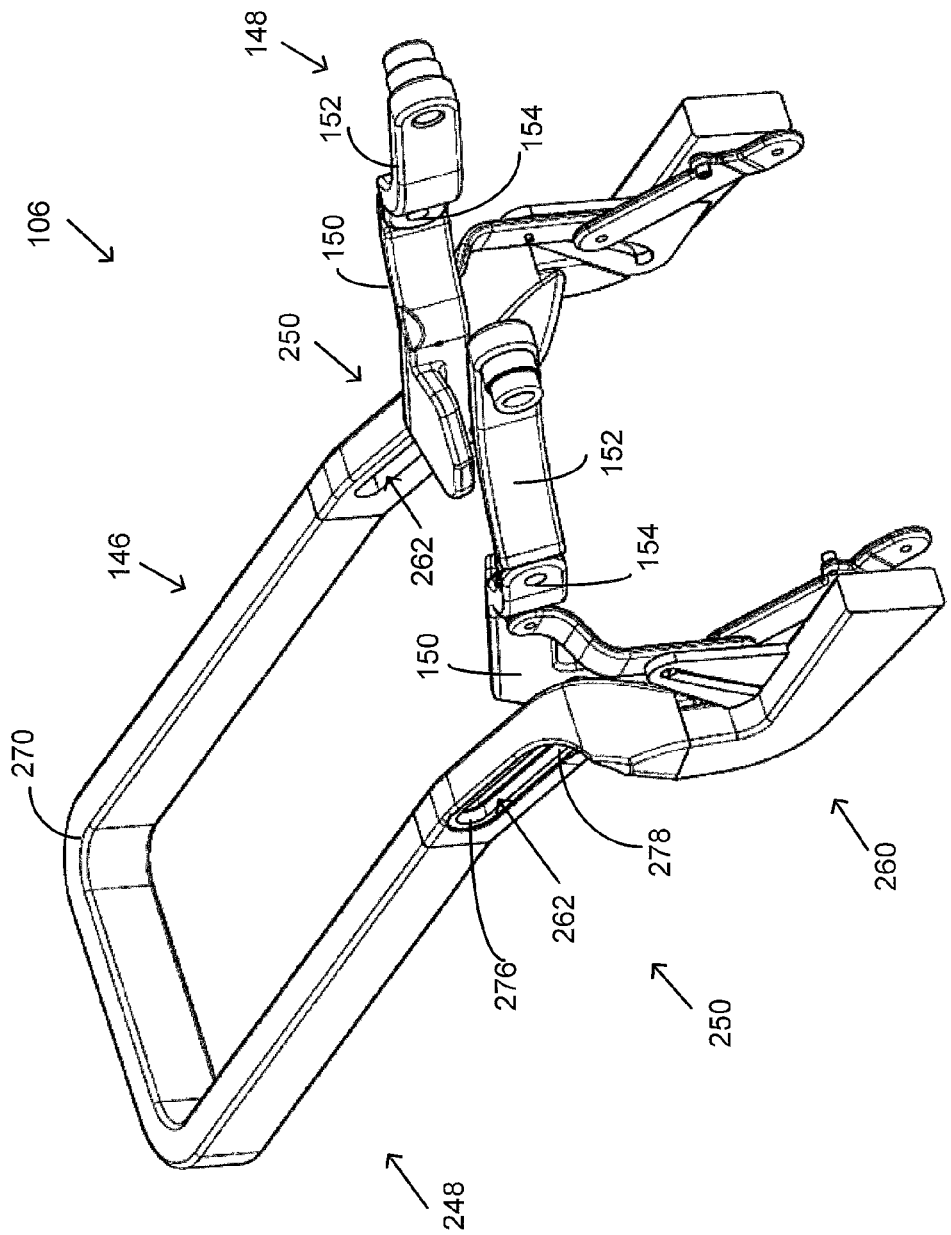
FIG. 44 is an isometric foot end view of the patient support in an extended position with the pads and torso assembly removed.
Figure 45:
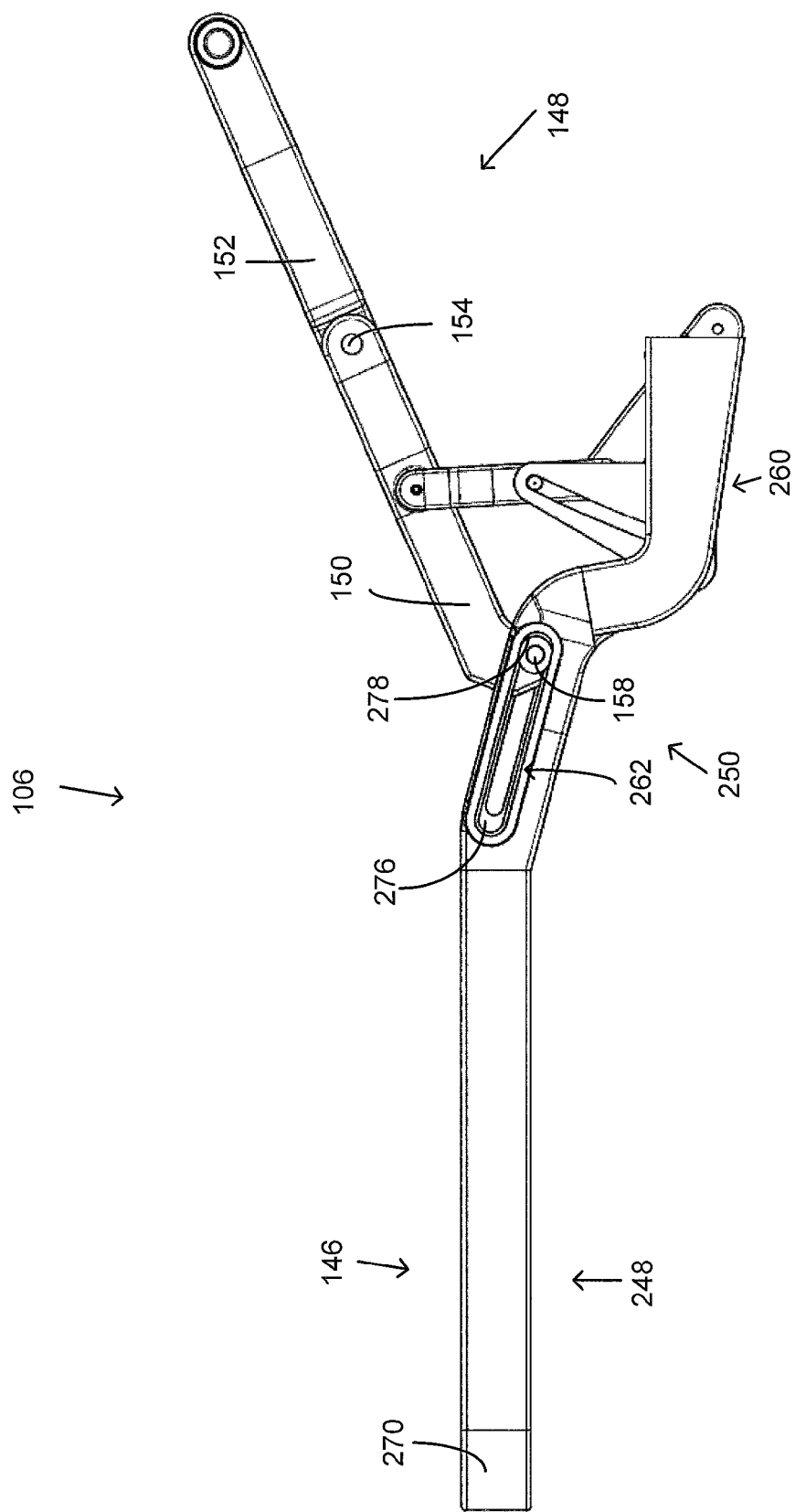
FIG. 45 is a side view of the patient support in an extended position with the pads and torso assembly removed.

FIGS. 39-41 show the patient support 106 without the torso assembly 246 and hip pads 274. As seen in these figures, in the neutral position (i.e., the inner frame 148 and outer frame 146 generally parallel to each other), the pivoting and translating hinge 158 is generally positioned in a central portion of the slot 262. As the inner frame 148 flexes or articulates about its hinge 154, as seen in FIGS. 42-43, the pivoting and translating hinge 158 generally translates towards a head end 276 of the slot 262 and rotates clockwise, using the view in FIG. 43 as a reference. On the other hand, as the inner frame 148 extends so as to position a patient in extension, as seen in FIGS. 44-45, the pivoting and translating hinge 158 generally translates towards a foot end 278 of the slot 262 and rotates counterclockwise, using the view in FIG. 45 as a reference. The pivoting and translating hinge 158 is similarly described in U.S. Provisional Patent Application Nos. 62/021,595, filed on Jukl. 7, 2014, titled "PATIENT SUPPORT STRUCTURE WITH PIVOTING AND TRANSLATING HINGE"; and 62/021,630, filed on Jul. 7, 2014, titled "SURGICAL TABLE WITH PATIENT SUPPORT HAVING FLEXIBLE INNER FRAME SUPPORTED ON RIGID OUTER FRAME". As stated previously, each of these applications is hereby incorporated by reference in its entirety into the present application. As such, the description of the hinge, among other components, in the incorporated applications is applicable to the present discussion and elements from the incorporated applications may be used as substitutes or in conjunction with the elements explicitly described herein.

Figure 46:
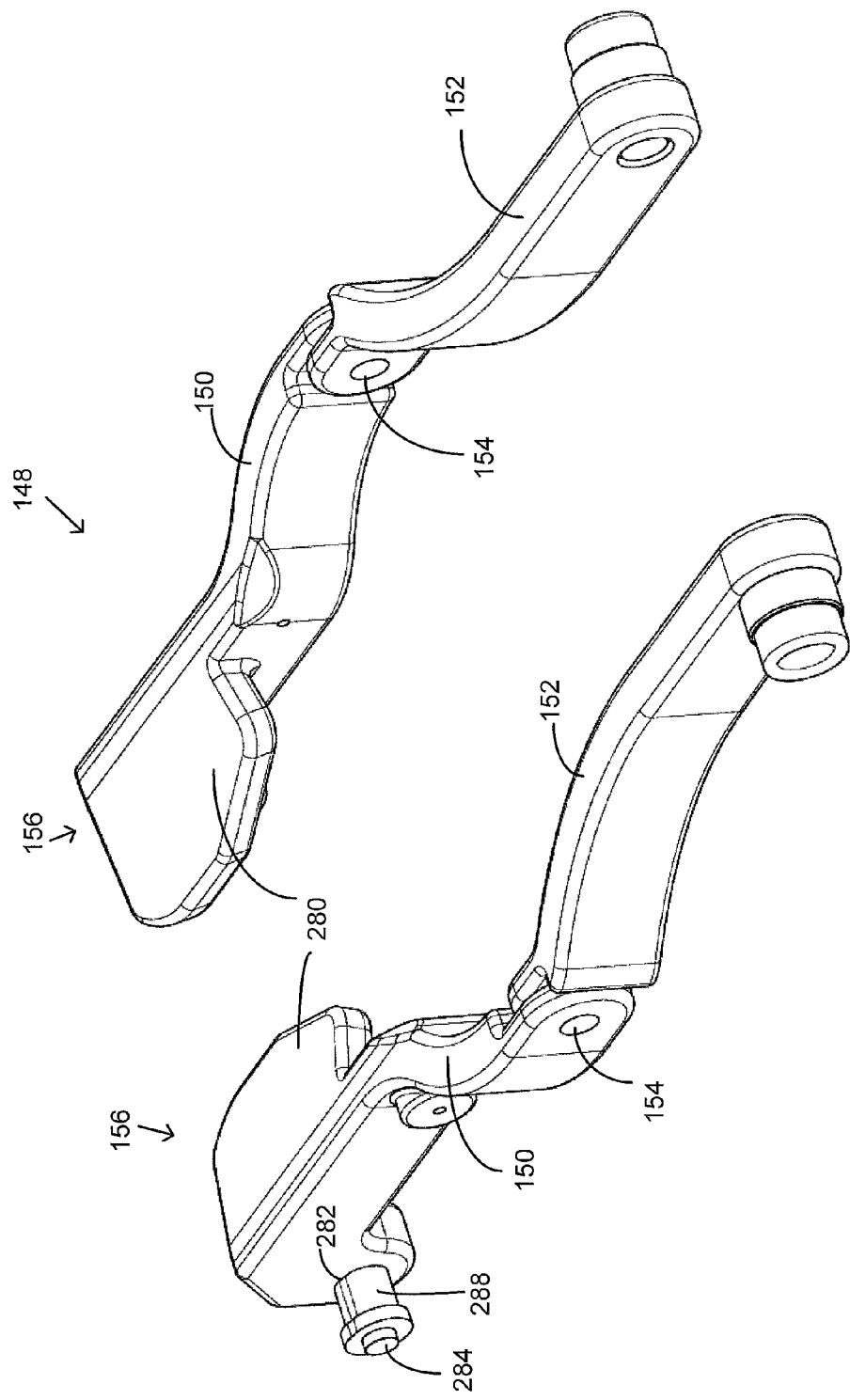
FIG. 46 is an isometric foot end view of the articulating inner frame.
Figure 47:
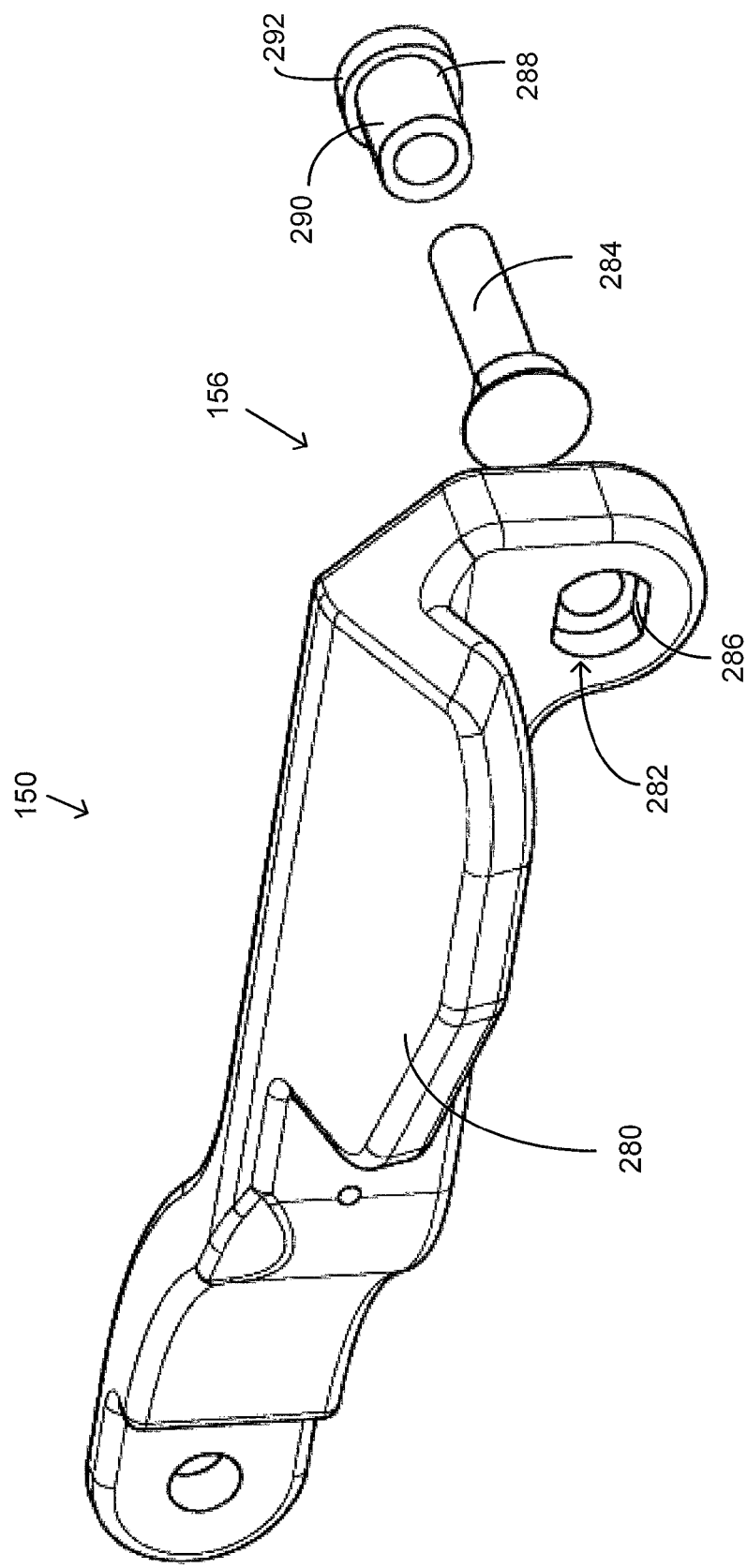
FIG. 47 is an isometric side view of an upper leg member of the inner frame.
Figure 48:
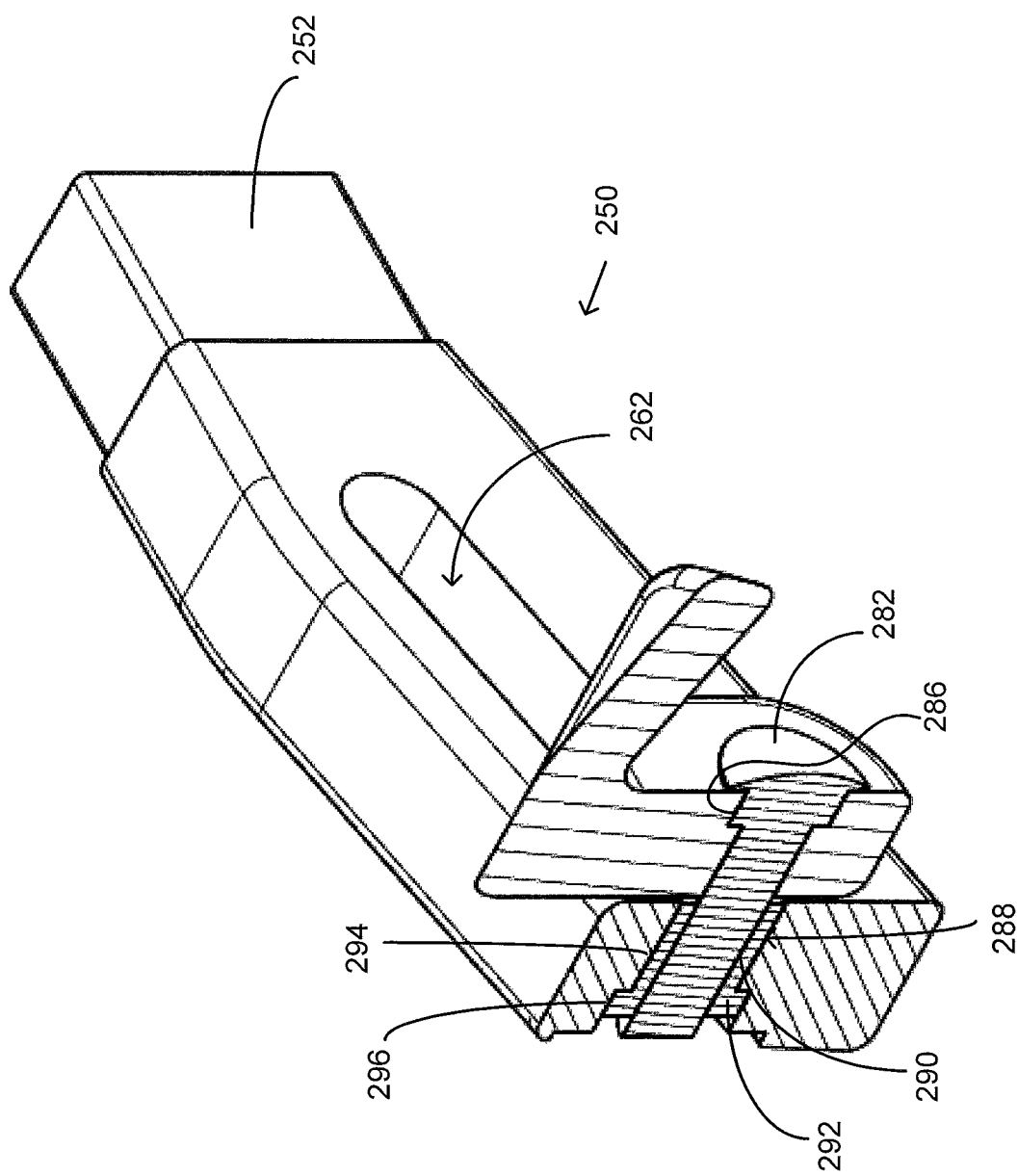
FIG. 48 is a transverse cross sectional view of the pivoting and translating hinge and bushing fitted within the slot of the middle section of the rigid outer frame.
Figure 49:
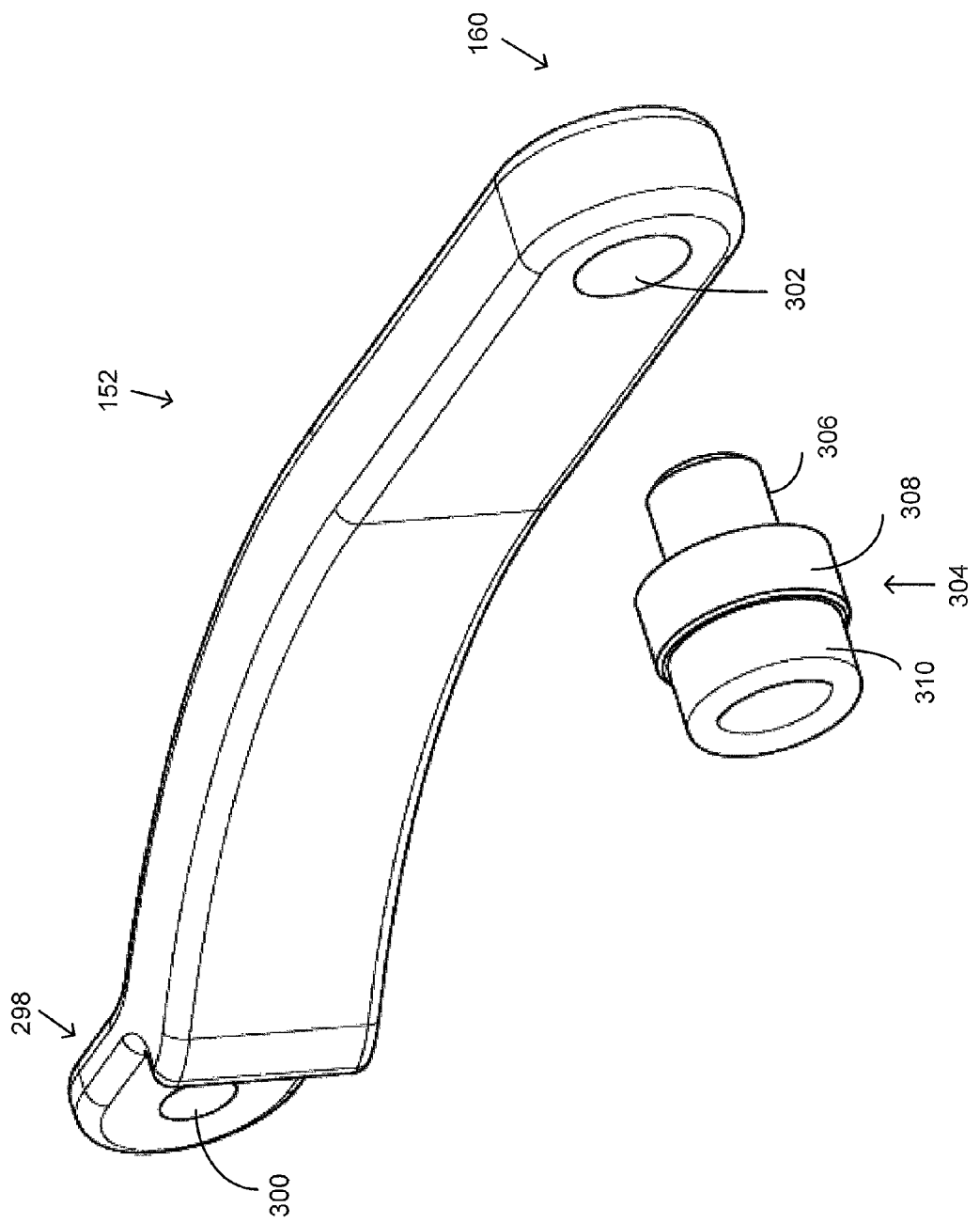
FIG. 49 is an isometric side view of a lower leg member of the inner frame.

Turning now to the inner frame 148, reference is made to FIGS. 46-49. As seen in the figures, the inner frame 148 includes the upper leg member 150 rotatably coupled with the lower leg member 152 via the hinge 154. As seen in FIGS. 46-47, the upper leg members 150 include an inwardly extending wing member 280 at the forward end 156 of the member 150 that is configured to support the hip pads 274 and the patient's hips. The forward end 156 of the upper leg members 150 also include a bore 282 extending transversely across the members 150. The bore 282 is configured to allow a bearing shaft 284 to extend therethrough and, as seen in FIGS. 47-48, the bore 282 may include a keyed recess 286 formed in the surface of the member 150 such that the bearing shaft 284 does not rotate therein once it is installed in the bore 282. The bearing shaft 284 is configured to extend through the bore 282 a sufficient distance such that a bushing 288 may be fitted over the shaft of the bearing shaft 284. The bushing 288 may be secured to the bearing shaft 284 in any number of ways and may be secured to the bearing shaft 284 after the shaft 284 is positioned within the slot 262 of the middle section 250 of the rigid frame 146. The bushing 288 includes a small diameter section 290 and a large diameter section 292 that match a respective small slot section 294 and large slot section 296 of the slot 262. Together, the components of the bearing shaft 282, bushing 288, and the slot 262 form the sliding and translating hinge 158. In this way, the inner frame 148 is pivotally and slidably coupled with the rigid outer frame 146 by the bearing shaft 282 and bushing 288 fitted within the slot 286 such that the small slot section 294 abuts the small diameter section 290 and the large slot section 296 abuts the large diameter section 292 during the pivoting and translating of the hinge 158 within the slot 262.

Referring to FIGS. 49-52, a forward end 298 of the lower leg member 152 includes a bore 300 that is generally coextensive with a bore at the rearward end of the upper leg member 150 when a bearing shaft extends through the bores 300 to hingedly couple the upper and lower leg members 150, 152. At the rearward end 160 of the lower leg member 152 is another bore 302 extending transversely through the member 152. Fitting within the bore 302 is a guide bushing 304 that is configured to slide on the guide member 162, shown in FIGS. 50-52, when the upper and lower leg members 150, 152 articulate relative to each other. The guide bushing 304 includes a small diameter section 306 that is configured to friction fit within the bore 304, a spacer section 308, and a guide surface section 310 opposite the small diameter section 306 that is configured to frictionally slide on the guide member 162.

FIGS. 50-52 depict the guide bushing 304 abutting the guide member 162 during various positions of the inner frame 148. In particular, as seen in FIGS. 50-51, the guide bushing 304 is positioned on the fourth horizontal section 228 of the guide member 162 when the patient support 106 is in a neutral position (i.e., when the inner frame 148 is generally parallel with the rigid frame 146). As seen in FIG. 51, the guide surface section 310 of the guide bushing 304 is in contact with the guide member 162 at the fourth horizontal section 228. It is noted, that in the neutral position, the pivoting and translating hinge 158 is generally positioned in between the head and foot ends 276, 278 of the slot 262. Turning to FIG. 52, the inner frame 148 is articulated at the hinge 154 so as to position a patient lying in a prone position in flexion. In this orientation, the pivoting and translating hinge 158 is at the head end 276 of the slot 262 and the guide bushing 304 is positioned at the junction between the first angled section 222 and the second horizontal section 224 of the guide member 162. The exact position of the guide bushing 304 on the guide member 162 may change based on the particular geometry of the upper and lower leg members 150, 152. Additionally, the trajectory and angling of the upper and lower leg members 150, 152 may be altered based on a different configuration of the guide member 162. For example, the guide member 162 may be altered to include a single horizontal section or three horizontal sections. Such modification may depend upon the desired movements of the patient's lower body for a particular surgical procedure. Thus, the shape of the guide member 162 is not intended to be limiting to the particular shape shown in the figures. Similarly, the position of the pivoting and translating hinge 158 may be different than shown in the figures without departing from the scope of the present disclosure.

As seen by comparing FIGS. 50 and 52, in the neutral position, shown in FIG. 50, the pivoting and translating hinge 158 is centrally positioned within the slot 262. And, in a flexed position, shown in FIG. 52, the pivoting and translating hinge 158 is pivoted clockwise and translated towards the head end 276 of the slot 262. This pivoting and translating movement of the hinge 158 allows for a patient positioned on the patient support 106 in a prone position to be flexed at the hips without the patient's torso being dragged or moved from its position on the chest pads of the torso assembly (not shown). Thus, the pivoting and translating hinge 158 eliminates the need for a torso assembly that slides during articulation of the patient support 106, which, as discussed previously, poses numerous problems to the patient.

Figure 53:
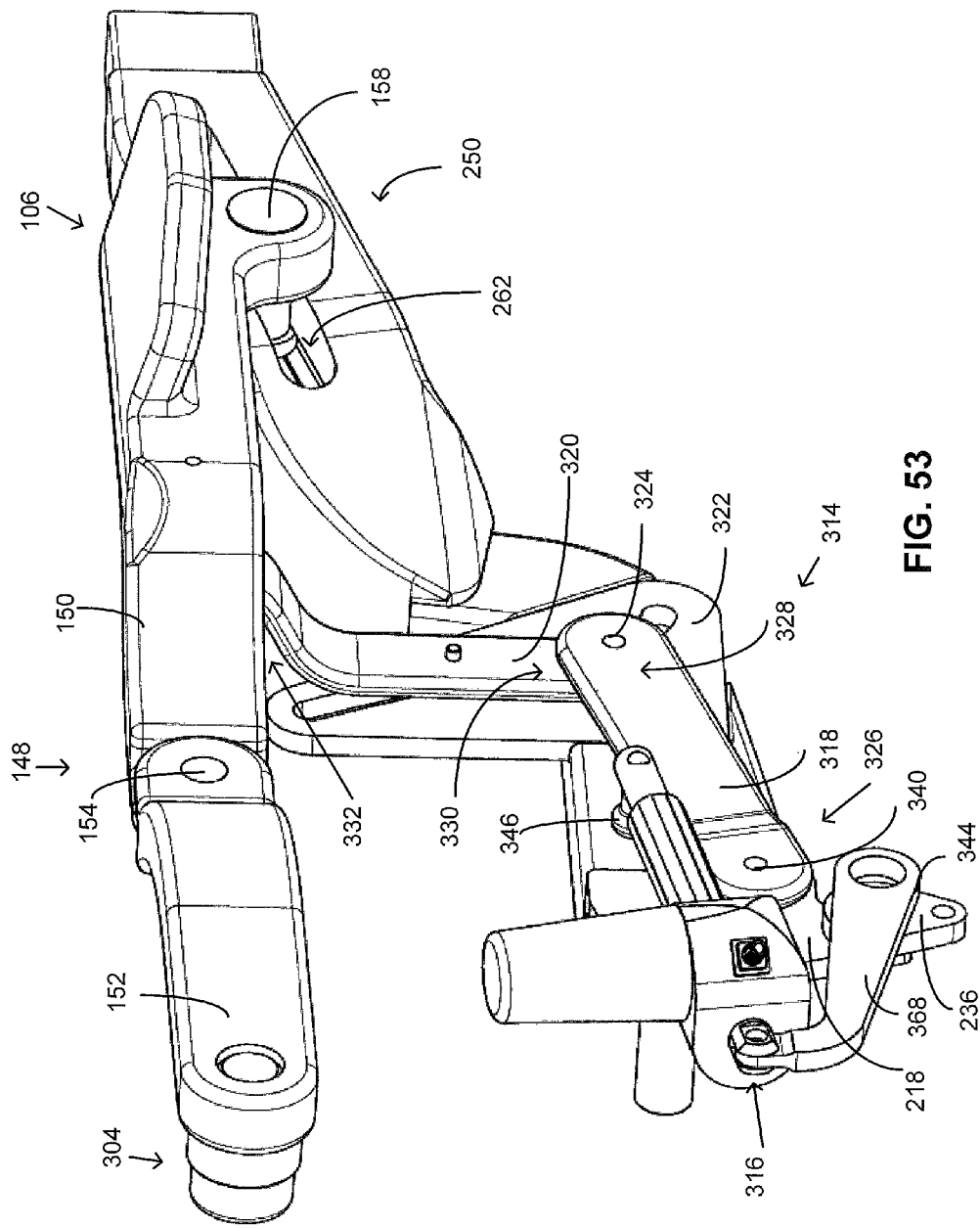
FIG. 53 is an isometric foot end view of the linkage and drive assembly coupled with the inner and outer frame.
Figure 54:
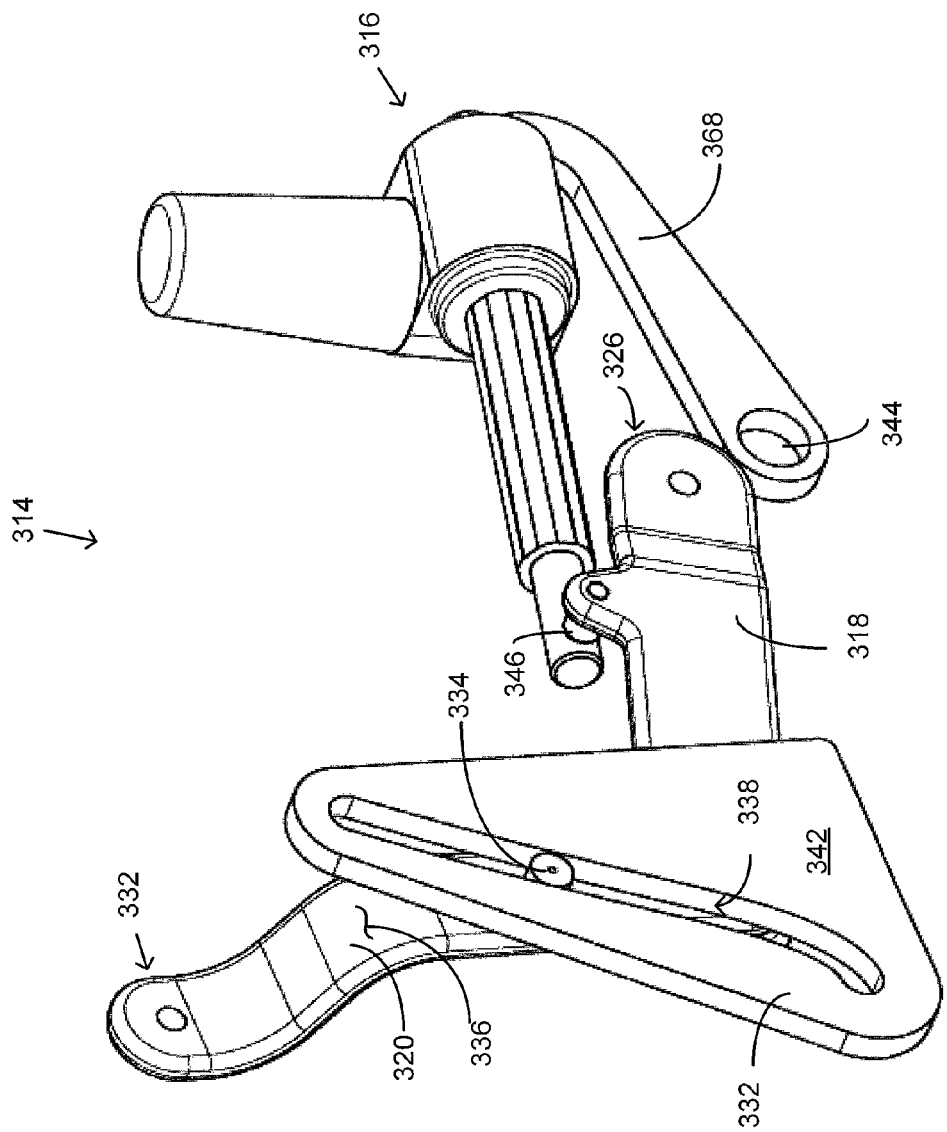
FIG. 54 is an opposite side isometric view of the linkage and drive assembly of FIG. 53.
Figure 55:
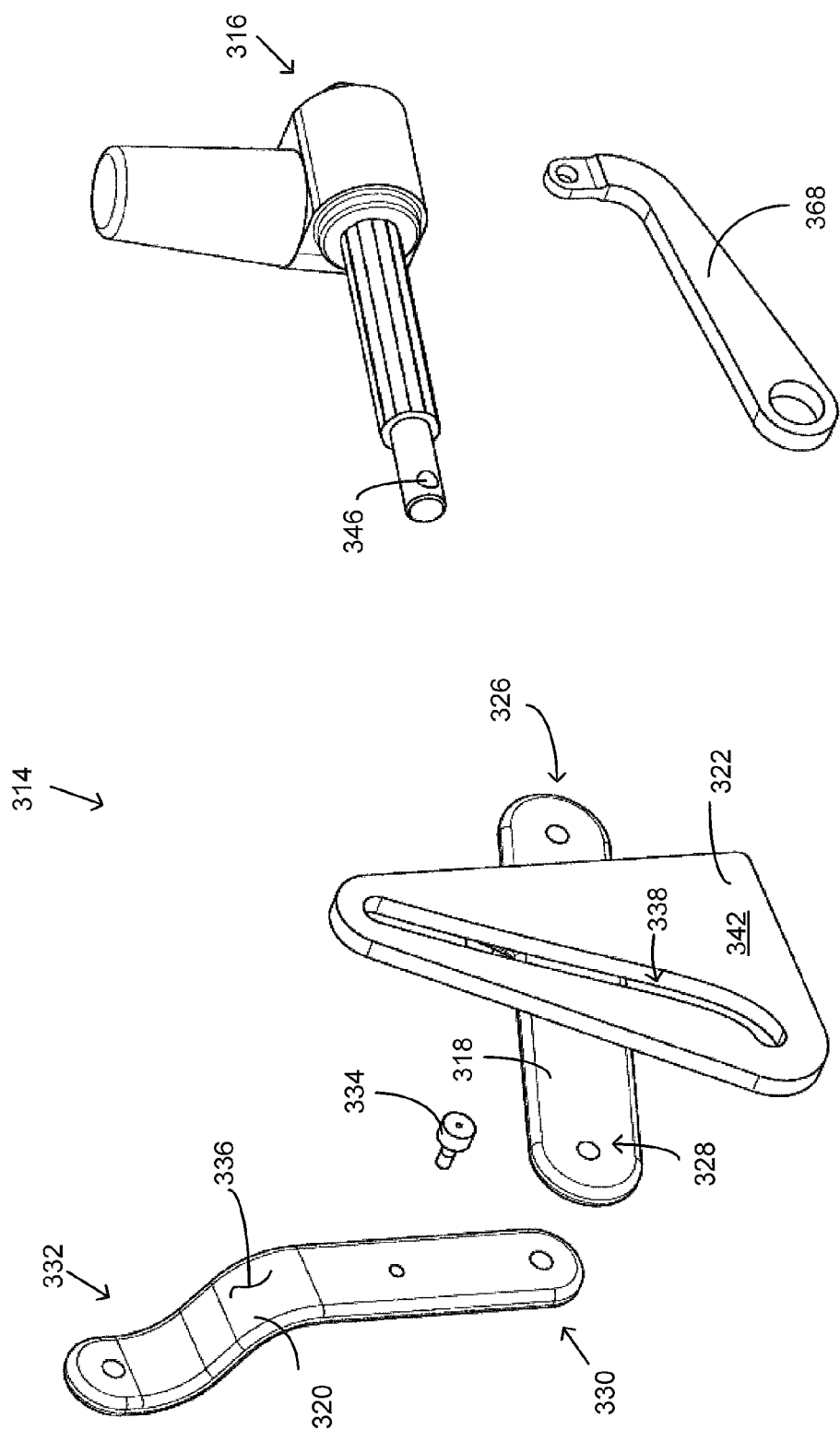
FIG. 55 is an exploded view of the linkage and drive assembly of FIG. 53.

Reference is now made to FIGS. 53-55, which depict various views of the inner frame articulation linkage and drive assembly 314 (hereinafter "linkage and drive assembly"). As seen in FIG. 53, which is an isometric view of the linkage assembly 314 and a portion of the patient support 106, the linkage assembly 314 includes an electric linear actuator 316, a lower articulation link member 318, an upper articulation link member 320, and cam path plate 322. The electric linear actuator 316 is coupled to the plate member 218 at one end 344 via a curved link member 368 that couples to a back side of the linear actuator 316. Opposite this, the linear actuator 316 is coupled to the lower articulation link member 318 at the other end 346. The lower articulation link member 318 is pivotally coupled with the plate member 218 at a foot end 326 of the link member 318 via a bearing shaft 340. Opposite the foot end 326, the lower articulation member 318 is pivotally coupled at a head end 328 with a foot end 330 of the upper articulation link member 320 via another bearing shaft 324. Opposite the foot end 330, a head end 332 of the upper articulation link member 320 is pivotally coupled with the upper leg member 150 of the inner frame 148.

Turning to FIG. 54, the upper articulation link member 320 is slidingly and pivotally coupled with the cam path plate 322 via a cam follower 334 that is rigidly coupled with a midsection of the upper articulation link member 320. The cam follower 334 is a bearing that extends outward from a side surface 336 of the upper articulation link member 320 and is fitted within a guide slot 338 formed in the cam path plate 322. The guide slot 338 is configured to guide the cam follower 334 during articulation of the upper and lower articulation link members 320, 318. As seen in FIGS. 54-55, the cam path plate 322 is a plate like member and the guide slot 338 is an opening extending between opposite side surfaces 342 of the plate 322. The guide slot 338 may be a milled path or the plate may be formed with the path of the guide slot 338. The particular path of the guide slot is determined based on a kinematic study of the desired movement of the linkage and drive assembly 314, which is informed by the desired movement of the patient during articulation of the table. The particular path of the guide slot 338 shown in the figures may change and be altered based on considerations of the desired patient movements during articulation of the table.

Referring still to FIGS. 54-55, the cam path plate 322 is rigidly coupled with the foot end section 260 of the rigid frame 146 such that as the linear actuator 316 is actuated to pivot the lower articulation link member 318 about the bearing shaft 340, the upper articulation link member 320 is guided in its articulation by the cam follower 334 being positioned within the guide slot 338 of the cam path plate 322. Movement of the cam follower 334 within the guide slot 338 causes the upper articulation link member 320 to translate and pivot about the cam follower 334. And, since the upper articulation link member 320 is pivotally coupled with the upper leg member 150 of the inner frame 148, articulation of the link members 318, 320 causes the upper leg member 150 to translate and pivot about the pivoting and translating hinge 158. In this way, the linkage and drive assembly 314 is effectively a three-bar linkage consisting of the lower articulation link member 318, the upper articulation link member 320, and the upper leg member 150 with a translating end at the hinge 158 and with restricted movement of the overall assembly caused by the cam follower 334 being guided by the guide slot 338 in the cam path plate.

Figure 56:
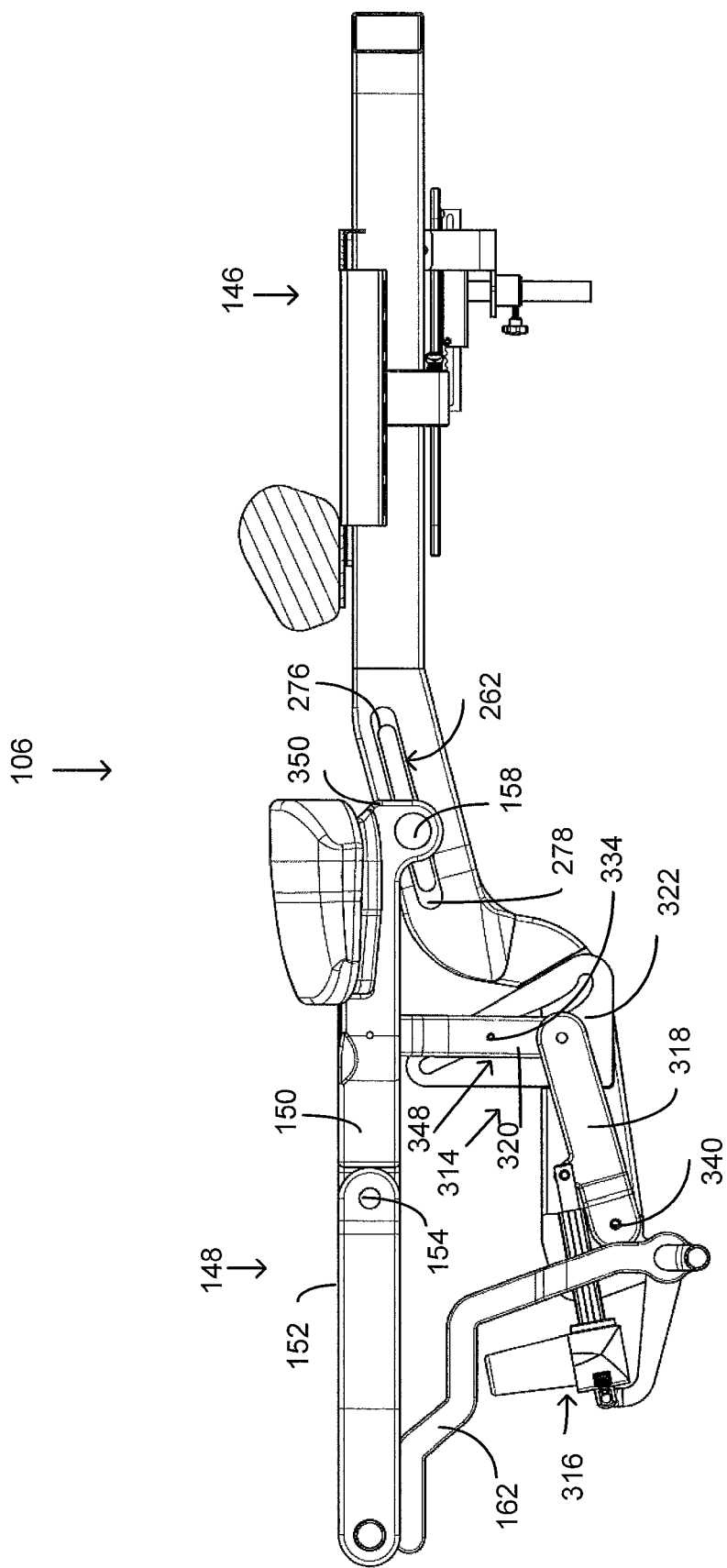
FIG. 56 is a side view of the patient support in a neutral position.
Figure 57:
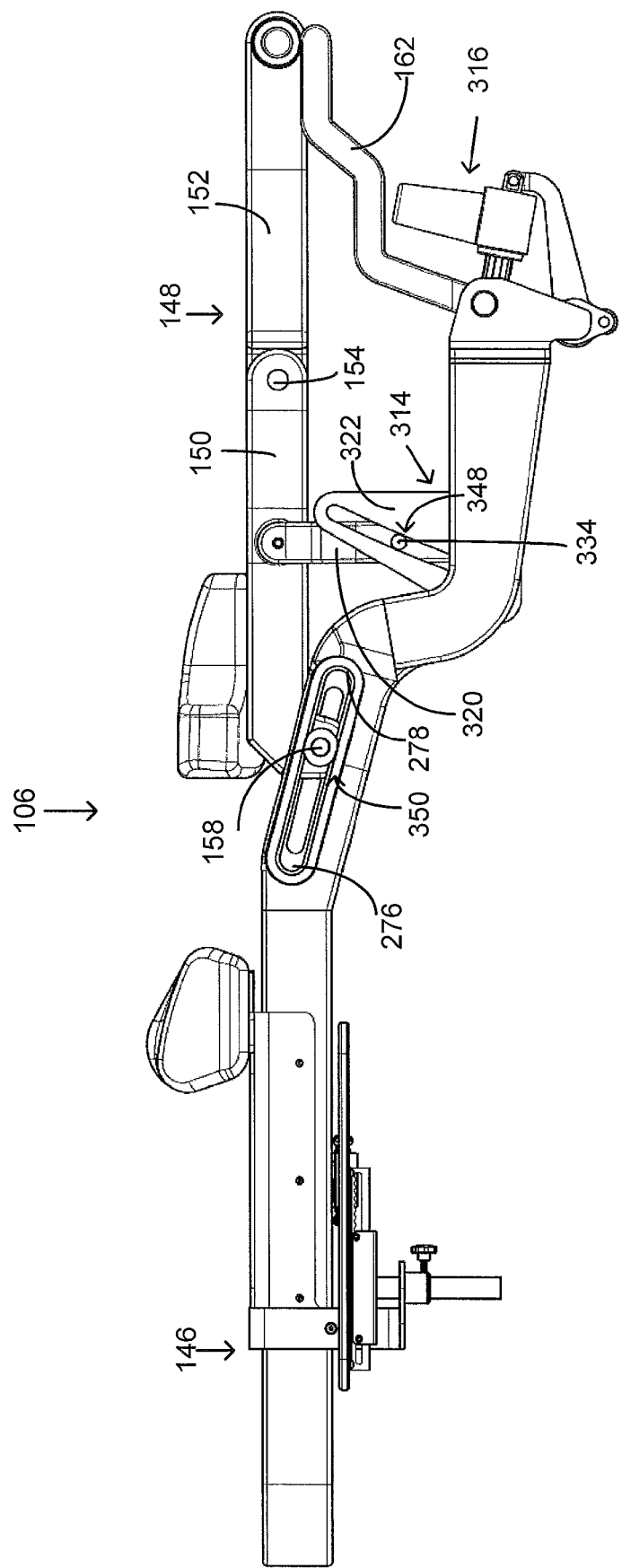
FIG. 57 is an opposite side view of the patient support as shown in FIG. 56.
Figure 58:
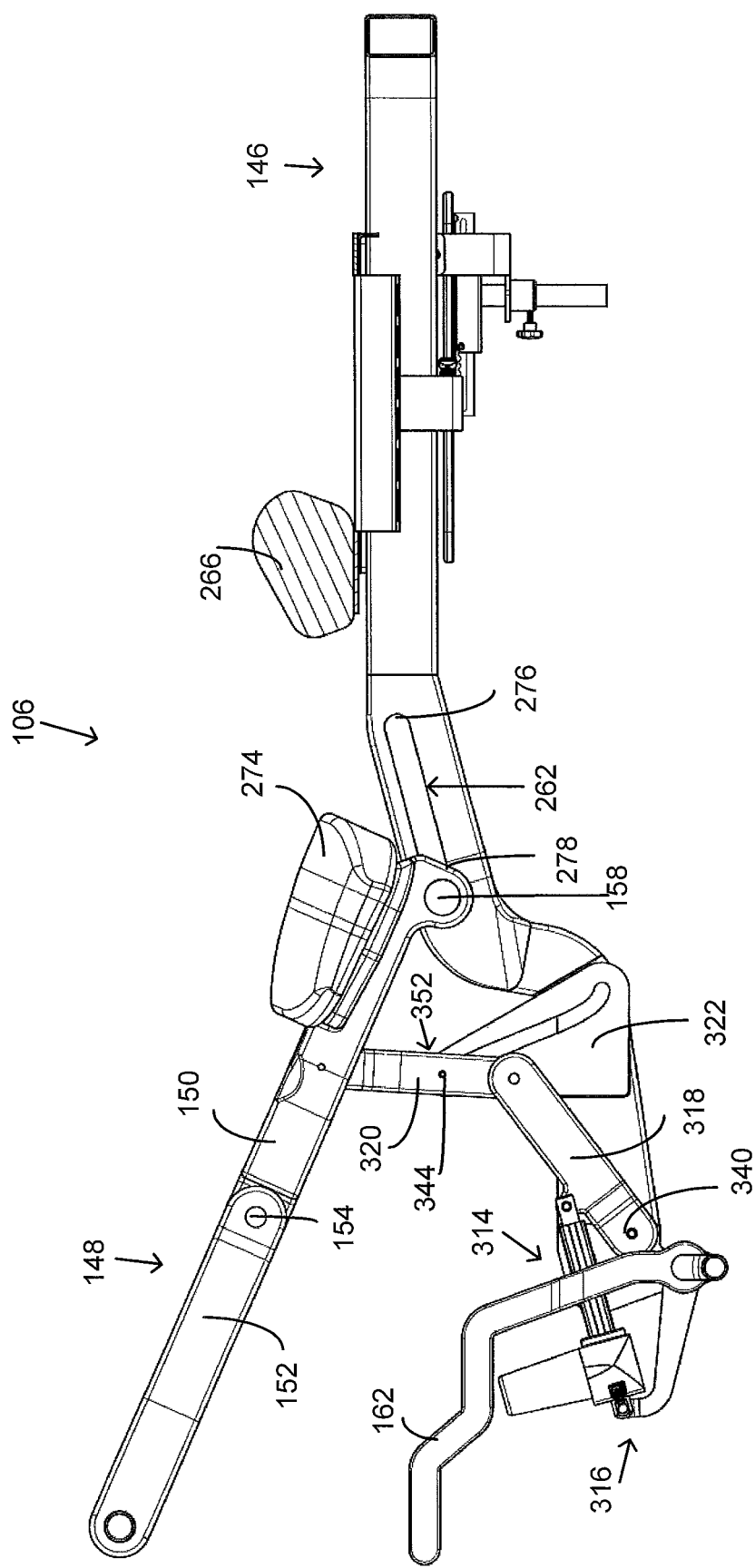
FIG. 58 is a side view of the patient support in an extended position.
Figure 59:
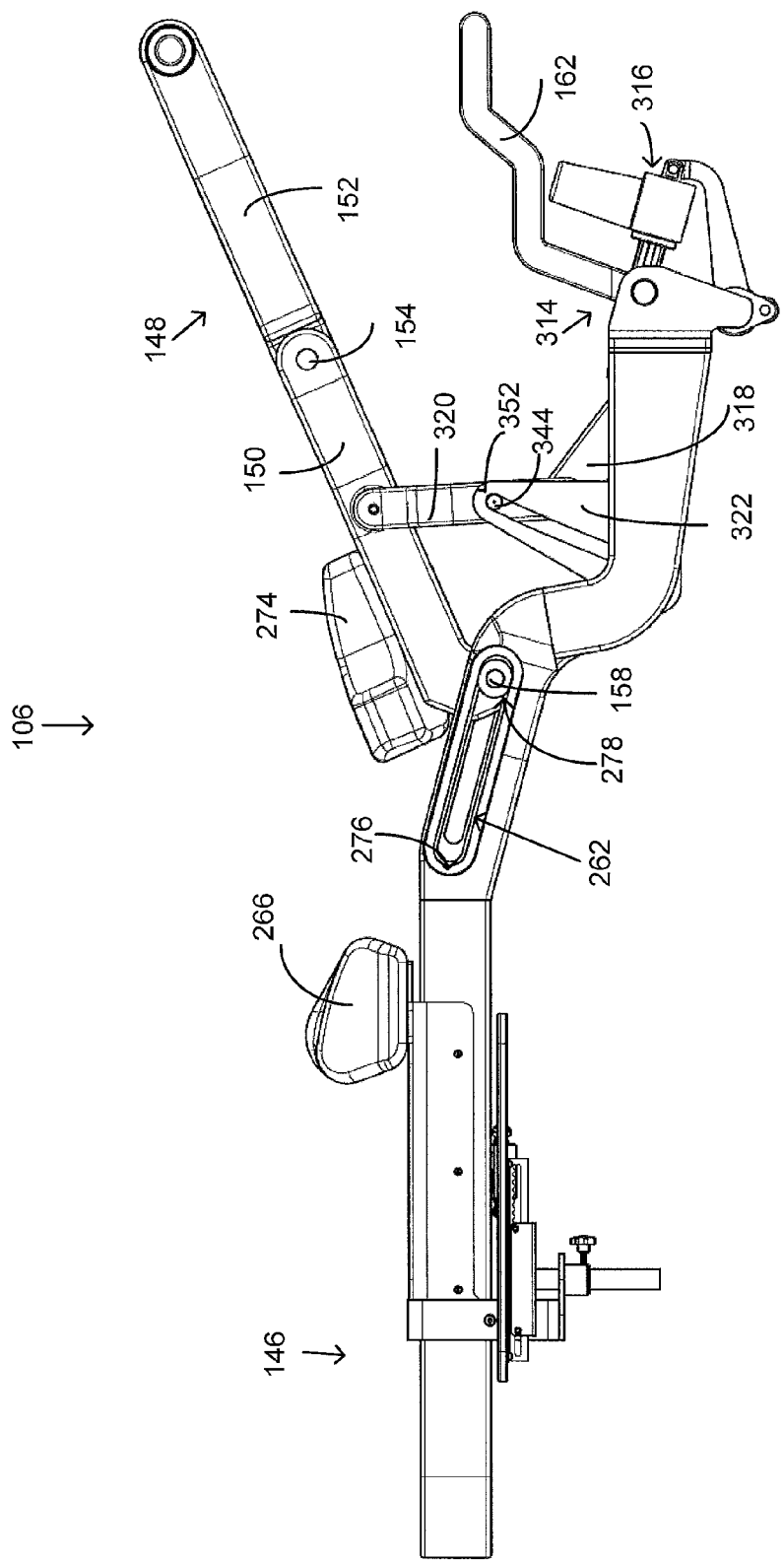
FIG. 59 is an opposite side view of the patient support as shown in FIG. 58.

Reference is made to FIGS. 56-63, which depict various longitudinal cross-sectional side views of the patient support 106 with the inner frame 148 in various degrees of articulation. As seen in FIGS. 56-57, which are opposite side views of the patient support 106 with the inner frame 148 in a neutral position, the cam follower 334 is positioned at a midsection 348 of the cam path plate 322 and the sliding and translating hinge 158 is positioned at a midsection 350 of the slot 262. As illustrated in FIGS. 58-59, as the linear actuator 316 pivots the lower articulation link member 318 counterclockwise, using the view in FIG. 58 as a reference, about the bearing shaft 340, the cam follower 334 is caused to translate towards an upper most end 352 of the guide slot 338 and the sliding and translating hinge 158 is caused to translate towards the foot end 278 of the slot 262. It is noted that positioning the patient in extension, with the patient support 106 as shown in FIGS. 58-59, positions the sliding and translating hinge 158 and, thus, the hip pads 274 furthest away from the chest pads 266. As such, moving from a neutral position, as shown in FIGS. 56-57, to an extended position, as shown in FIGS. 58-59, causes the inner frame 148 to pivot upwards to angle the patients' legs upward while simultaneously translating the hip pads 274 rearwardly. This movement of the various components of the patient support 106 enables the patient's torso to remain stationary on the torso assembly 246 while the patient is moved from a neutral position to an extended position, among others.

Figure 60:
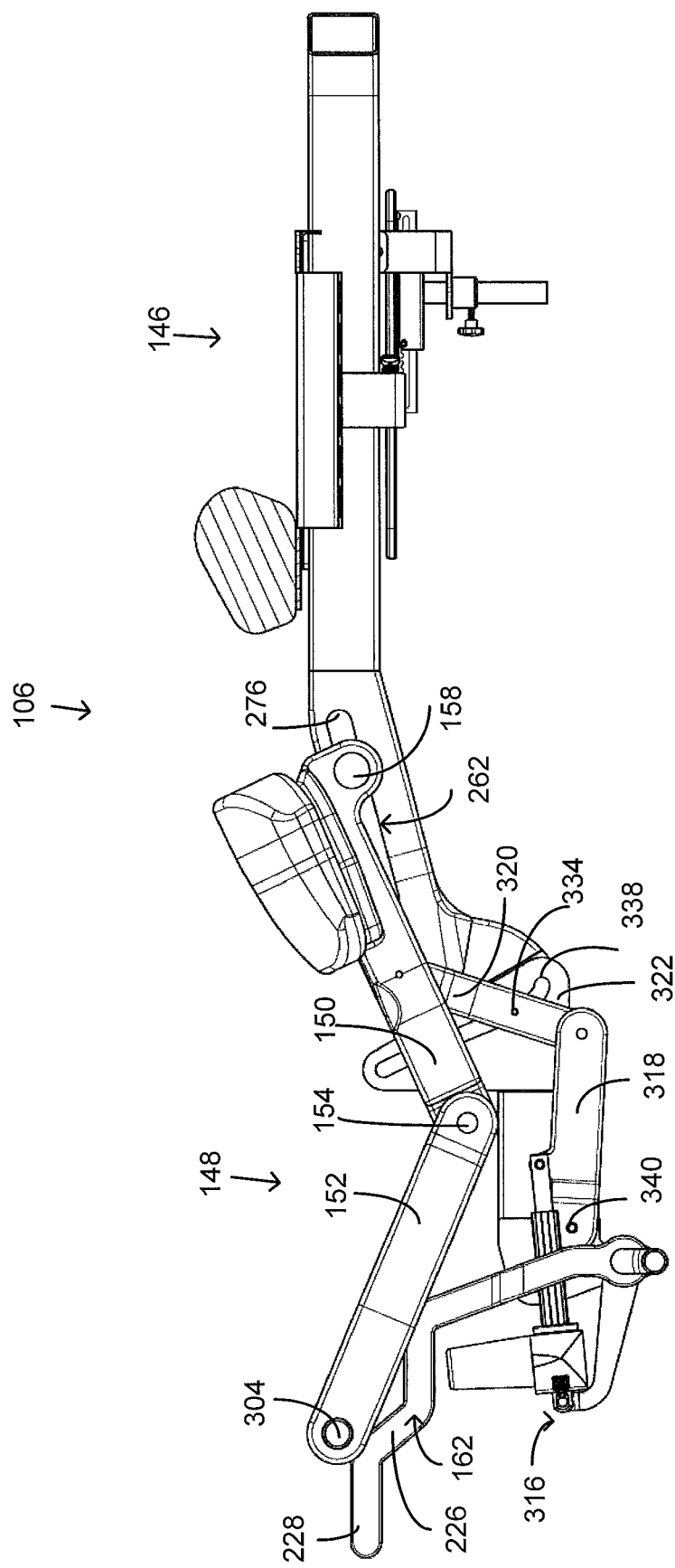
FIG. 60 is a side view of the patient support in a partially flexed position.
Figure 61:
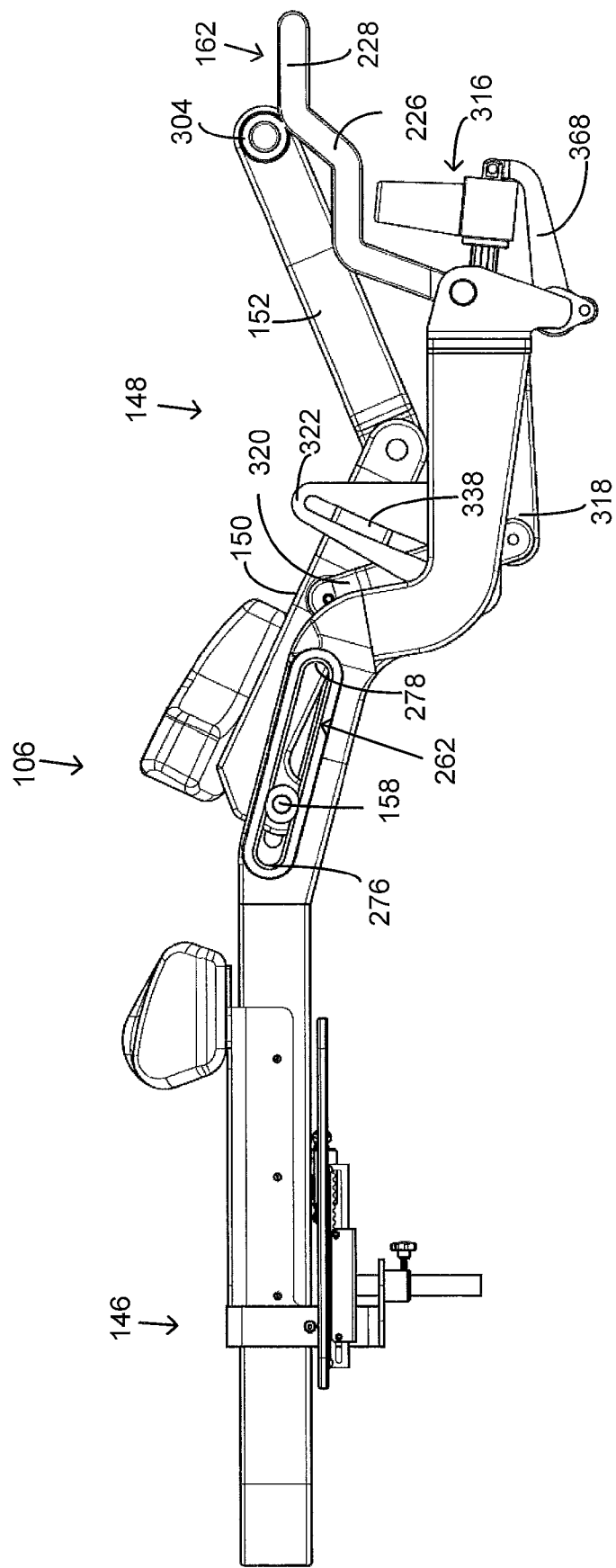
FIG. 61 is an opposite side view of the patient support as shown in FIG. 60.
Figure 62:
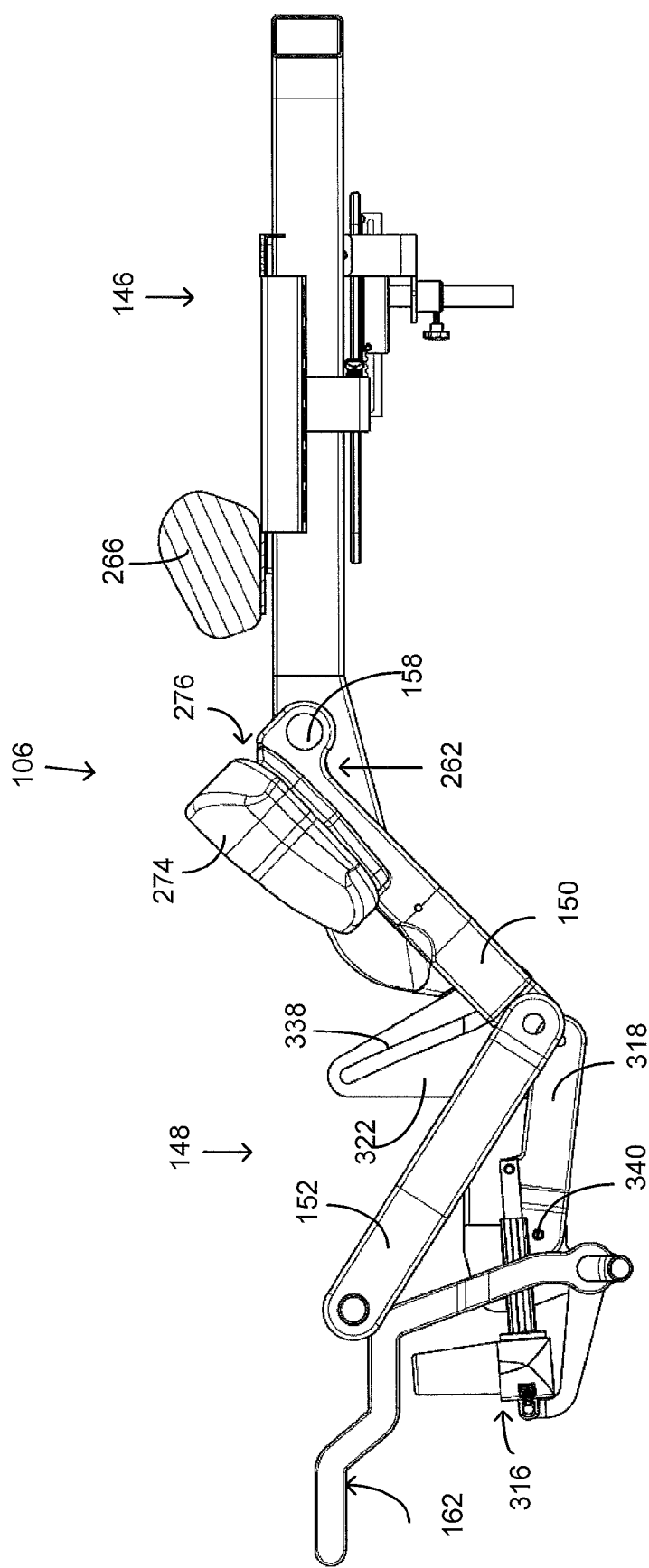
FIG. 62 is a side view of the patient support in a fully flexed position.
Figure 63:
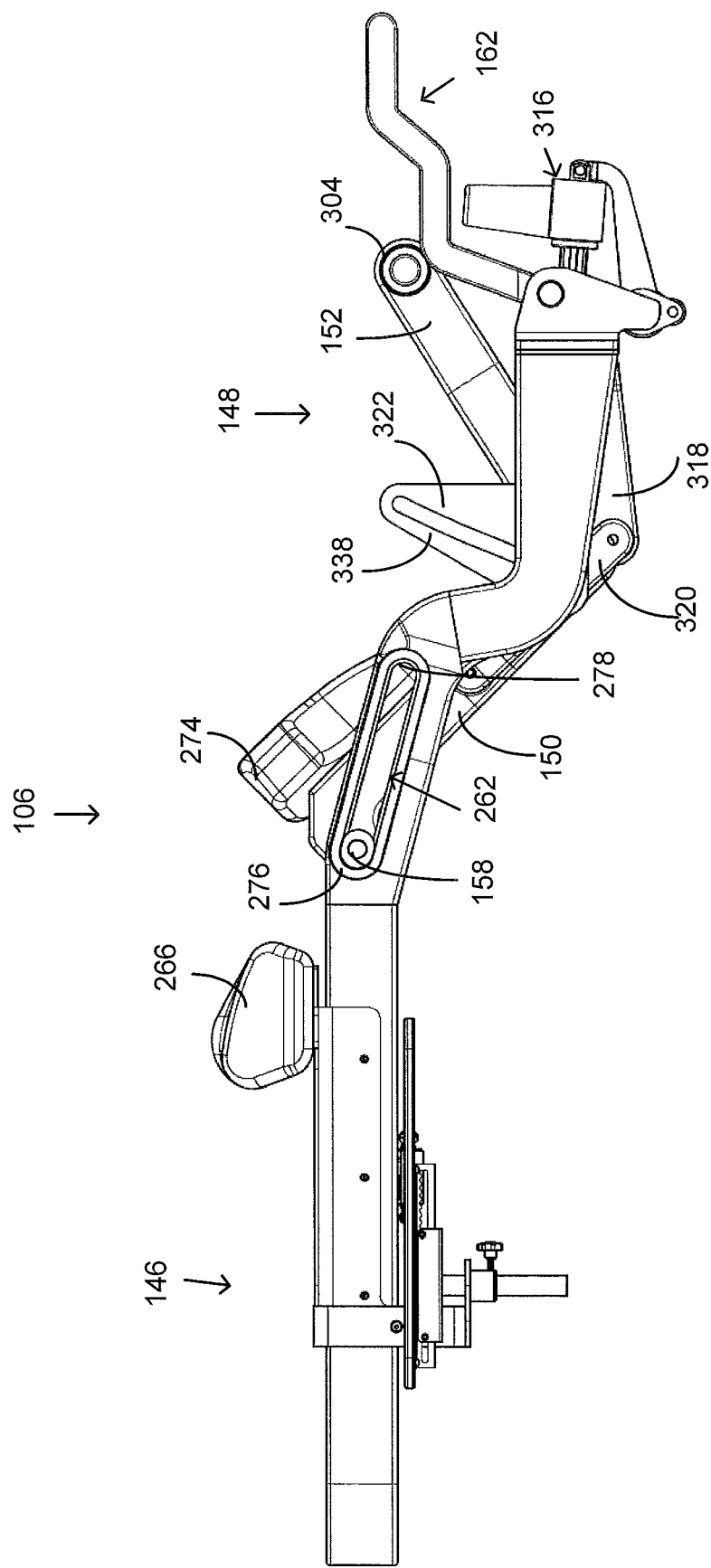
FIG. 63 is an opposite side view of the patient support as shown in FIG. 62.

FIGS. 60-63 illustrate the patient support 106 in two states of flexion. FIGS. 60-61 illustrate the patient support 106 in a half-flexed position while FIGS. 62-63 illustrate the patient support 106 in full flexion. As seen in FIGS. 60-61, as the linear actuator 316 pivots the lower articulation link member 318 about the bearing shaft 340 in a clockwise direction, using the view in FIG. 60 as a reference, the cam follower 334 is caused to translate downward along the guide 338 (relative to the neutral position, shown in FIGS. 56-57) and the sliding and translating hinge 158 is caused to translate towards the head end 276 of the slot 262. The sliding and translating hinge 158 is also caused to pivot counterclockwise, as seen in FIG. 60, which causes the upper and lower leg members 150, 152 to articulation relative to each other. It can be seen in FIG. 61 that, in this orientation, the guide bushing 304 is positioned at an intersection of the third angled section 226 and the fourth horizontal section 228 of the guide member 162.

As seen in FIGS. 62-63, as the linear actuator 316 further pivots the lower articulation link member 318 about the bearing shaft 340, the cam follower 334 is caused to translate to a lower end 354 of the guide slot 338 and the sliding and translating hinge 158 is caused to translate towards the head end 276 of the slot 262. As seen in the figures, when in full flexion, the hip pads 274 and the chest pads 266 are at their closest approximation.

II. Movement of the Surgical Table

Figure 64:
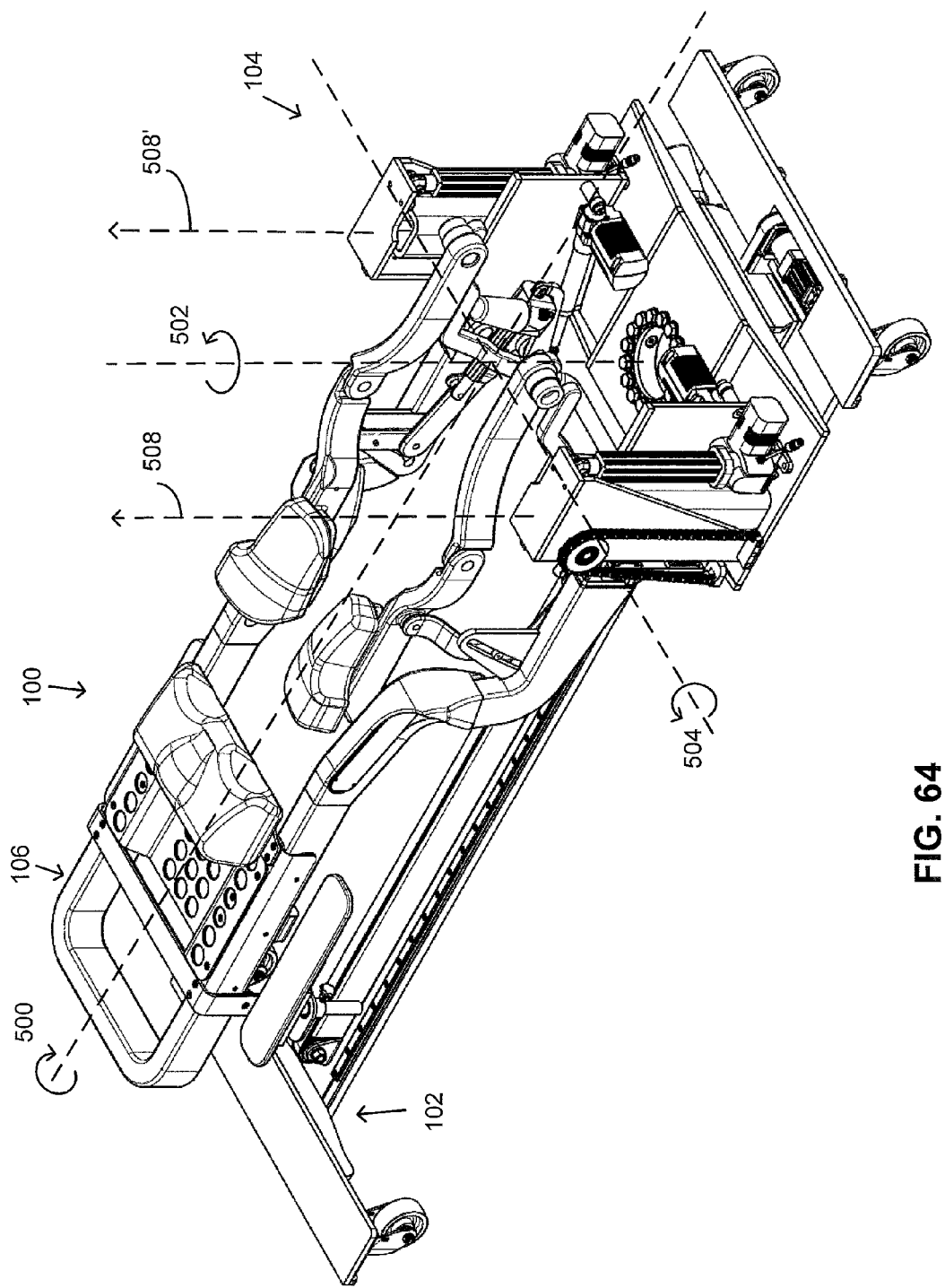
FIG. 64 is an isometric foot end view of the surgical table of FIG. 1 showing various axes of movement, pivoting, etc.

For a detailed description of the movement of the surgical table 100 relative to a plurality of axes, reference is made to FIG. 64. In one implementation, the plurality of axes includes, without limitation, a longitudinally extending roll axis 500, a vertical pivot axis 502, an angulation axis 504, a longitudinal axis 506 of the base 102, and vertically extending longitudinal axes 508, 508' of the column assemblies 138, 138'.

As can be understood from FIG. 64, in one implementation, the roll axis 500 extends longitudinally along a length of the patient support 106 and generally through a midpoint between the cylindrical shafts 210, 210' extending through the bearing blocks 208, 208'. The vertical pivot axis 502 extends vertically upward from a midpoint of the slewing ring bearing 134 positioned within the base 102. The vertically extending longitudinal axes 508, 508' extend vertically upward from each of the column assemblies 138, 138'. The angulation axis 504 extends generally through the cylindrical shafts 216, 216' extending transversely through the bearing blocks 208, 208'. And, the longitudinal axis 506 of the base 102 extends generally along the track 124 extending between the forward end 112 and back end 126 of the base 102.

As described in detail herein, the support column 104 is configured to translate along the longitudinal axis 506 of the base 102 and is configured to pivot about the vertical pivot axis 502 at any point along the longitudinal axis 506. Additionally, the support column 104 is configured to tilt, angle, or pivot the patient support 106 about the angulation axis 504 at any point along the longitudinal axis 506 of the base 102. The support column 104 is also configured to roll or pivot the patient support 106 about the longitudinally extending roll axis 500 at any point along the longitudinal axis 506 of the 102. And, the support column 104 is configured to raise and lower the column assemblies 138, 138' in tandem to facilitate raising and lowering the patient support 106 about the vertically extending longitudinal axes 508, 508', and is configured to raise and lower the column assemblies 138, 138' independently to facilitate rolling or pivoting of the patient support 106 about the longitudinally extending roll axis 500. In one implementation, the surgical table 100 is configured to perform any combination of the above described movements at a given time without limitation.

In one implementation, the support column 104 is configured to translate about 60 inches along the base 102 and the support column 104 is configured to angle the patient support 106 about 12 degrees on either side of a neutral position (i.e., longitudinal axis of patient support is parallel with longitudinal axis of base). In one implementation, the column assemblies 138, 138' are configured to raise the patient support 106 about 400 millimeters (mm) along the vertically extending longitudinal axes 508, 508' and are configured to independently operate such that the patient support 106 can roll about the roll axis 500 about 20 degrees on either side of a neutral position. Finally, in one implementation, the support column 104 is configured to pivot or rotate about the vertical pivot axis 502 about 12 degrees on either side of a neutral position.

Figure 65A:
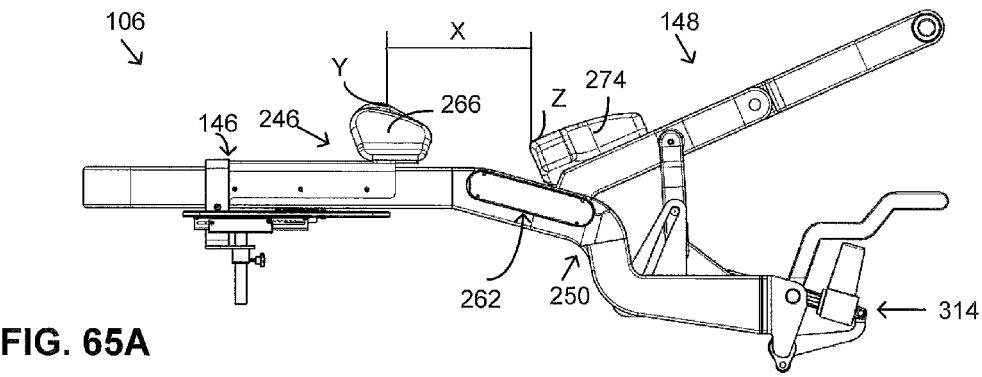
FIG. 65A-65C are side views of the patient support shown in extension, neutral, and flexion with a constant distance between a point on the chest pad and a point on the hip pad.
Figure 65B:
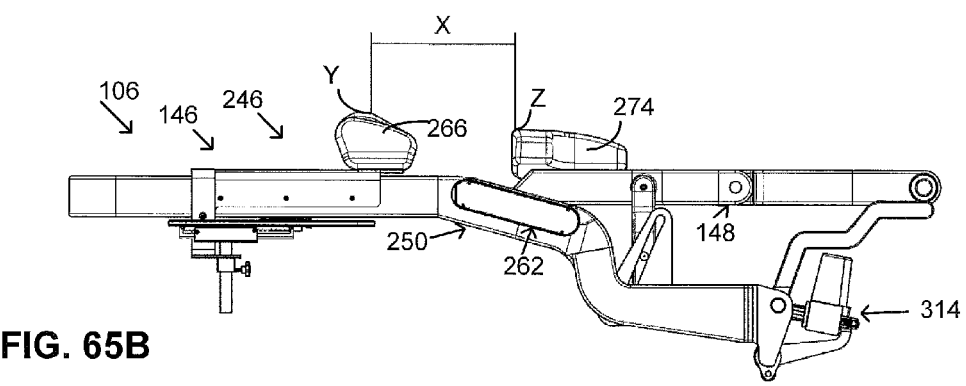
Figure 65C:
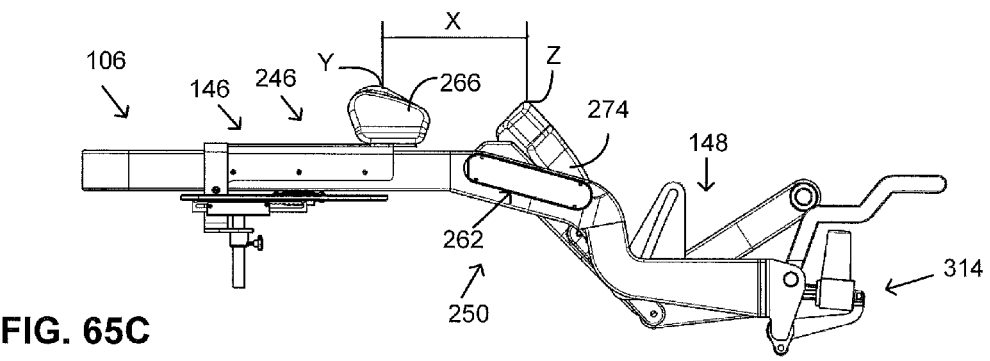

In one implementation and referring to FIGS. 65A-65C, which depicts a side view of a patient support 106 in extension, neutral, and flexion, the surgical table 100 is configured to articulate around the various axes described above so as to keep the surgical field stationary. Stated differently, the patient's upper body may remain stationary, which is beneficial when the patient is under anesthesia, while the table 100 articulates with the various assemblies described herein. To facilitate keeping the patient's upper body stationary during articulation of the inner frame 148 relative to the rigid outer frame 146, the surgical table 100 is configured to maintain a substantially constant or fixed longitudinal distance X between a point Y on the chest pad 266 and a point Z on the pelvic pad 274. As seen in FIGS. 65A-65C, the longitudinal distance X remains substantially fixed during extension (FIG. 65A), neutral (FIG. 65B), and flexion (FIG. 65C), among all other points in between. The dimensions and orientations of the slot 262 within the middle section 250 of the rigid frame 146 along with the movements and articulations of the linkage and drive assembly 314 facilitate the distance X being substantially constant during the various stages of articulation.

As discussed in related U.S. Patent Application No. 62/021,595, filed on Jul. 7, 2014, titled "PATIENT SUPPORT STRUCTURE WITH PIVOTING AND TRANSLATING HINGE", the slot 262 is angled about 15 degrees from horizontal and may include a length of about 9 inches, and may further include a translational movement of about 3.5 inches when moving from a neutral position to an extended position of about twenty-five degrees. And, the slot 262 may include a translational movement of about 5.5 inches when moving from a neutral position to a flexed position of about forty-five degrees. Stated differently, to move from a neutral position to an extended position, the pivoting and translating hinge 158 pivots about twenty-five degrees and translates about 3.5 inches caudally within the slot 262 which angles downward as it extends caudally. And, to move from a neutral position to a flexed position, the pivoting and translating hinge 158 pivots about forty-five degrees and translates about 5.5 inches cranially within the slot 262. In certain implementations, the pivoting and translating hinge 158 may translate within the slot 262 about one inch for about every 8 degrees +/− about 2 degrees of rotation when moving from a neutral position to a flexed position. And, in certain implementations, the pivoting and translating hinge 158 may translate within the slot 262 about one inch for about every 7 degrees +/− about 2 degrees of rotation when moving from a neutral position to an extended position. The exact length and angular orientation of the slot 262, however, may be different depending on the particular needs of the surgical table 100, the surgical procedure, or the patient, among other variables.

When a patient's torso and pelvis are manipulated with the surgical table 100, shown in FIGS. 65A-65B, from a neutral position to an extended position, for example, the pelvis must rotate around the hips, wherein the top of the sacrum gets closer to the trunk region while the lumbar spine increases its lordosis. To compensate for this, the torso must either move away from the sacrum and pelvis in a cephalad direction, which is undesirable as it moves the patient towards anesthesia equipment, or the pelvis must move caudad, which is more desirable. As stated previously, it is preferable for the torso, including the patient's head, to remain stationary during articulation and angulation of the inner frame 148 about the pivoting and translating hinge 158 so that access to the patient's upper body is undisturbed. This is better for anesthesia and the safety of the patient under a general anesthesia. If this type of movement does not occur, the lumbar spine can undergo unwanted compression, which can be harmful, especially to neurologic structures.

When a patient's torso and pelvis are manipulated into flexion, as shown in FIGS. 65B-65C, the pelvis must rotate considerably around the hips in an opposite direction from that of extension described above. To avoid unwanted distraction of the lumbar spine, the torso and head must move, or the pelvis must move cephalad leaving the torso and head unchanged in position with respect to the torso assembly 246 and relative to personnel providing anesthesia. In this way, the distance X between fixed points Y, Z on the chest and pelvic pads remains substantially constant and unchanging with full flexion and extension of the inner frame 148 relative to the outer frame 146 of the surgical table 100.

Figure 66:
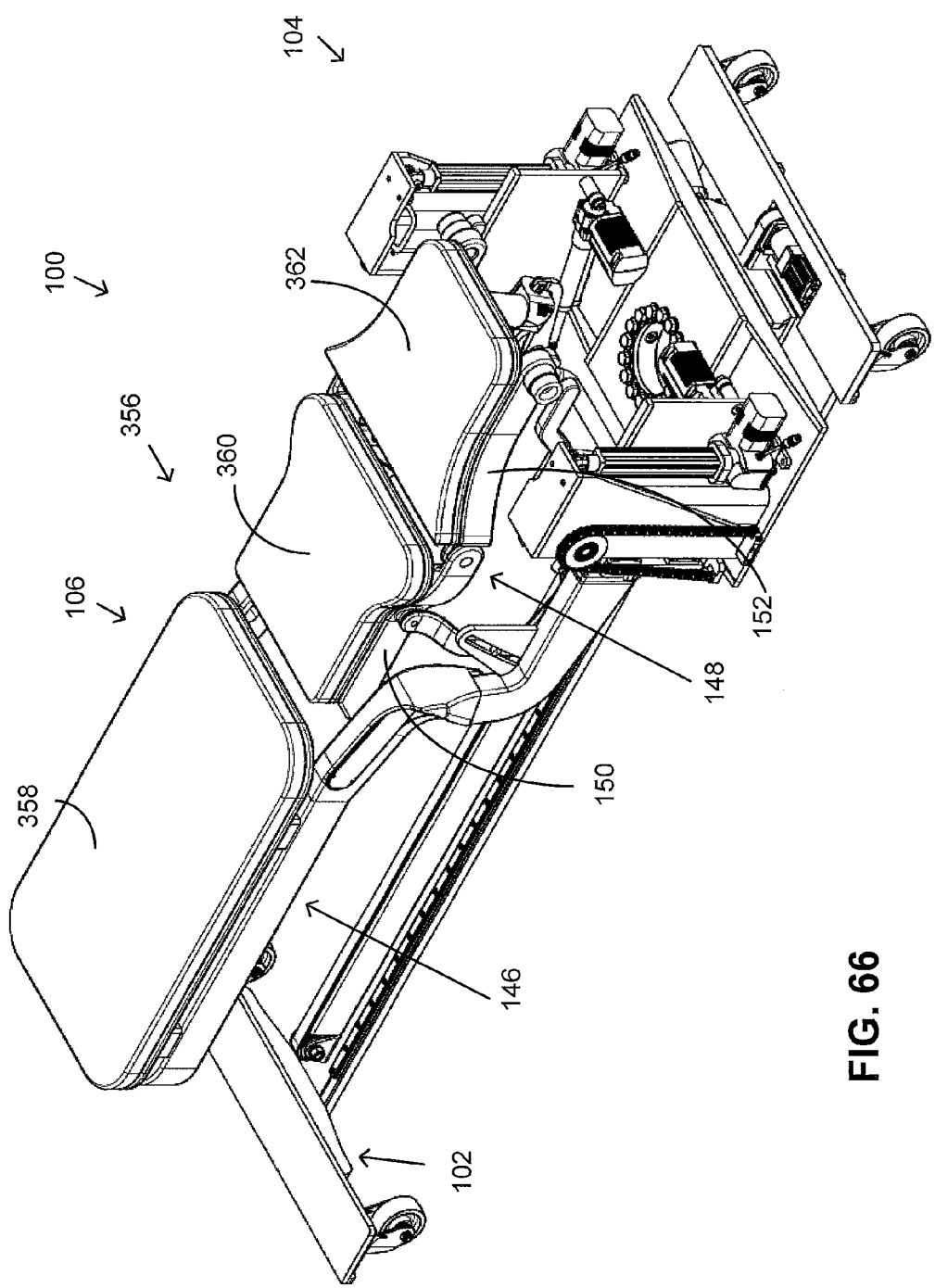
FIG. 66 is an isometric foot end view of the surgical table of FIG. 1, except the table of FIG. 66 includes flat-top pads and supports for positioning a patient in a supine position, for example.
Figure 67A:
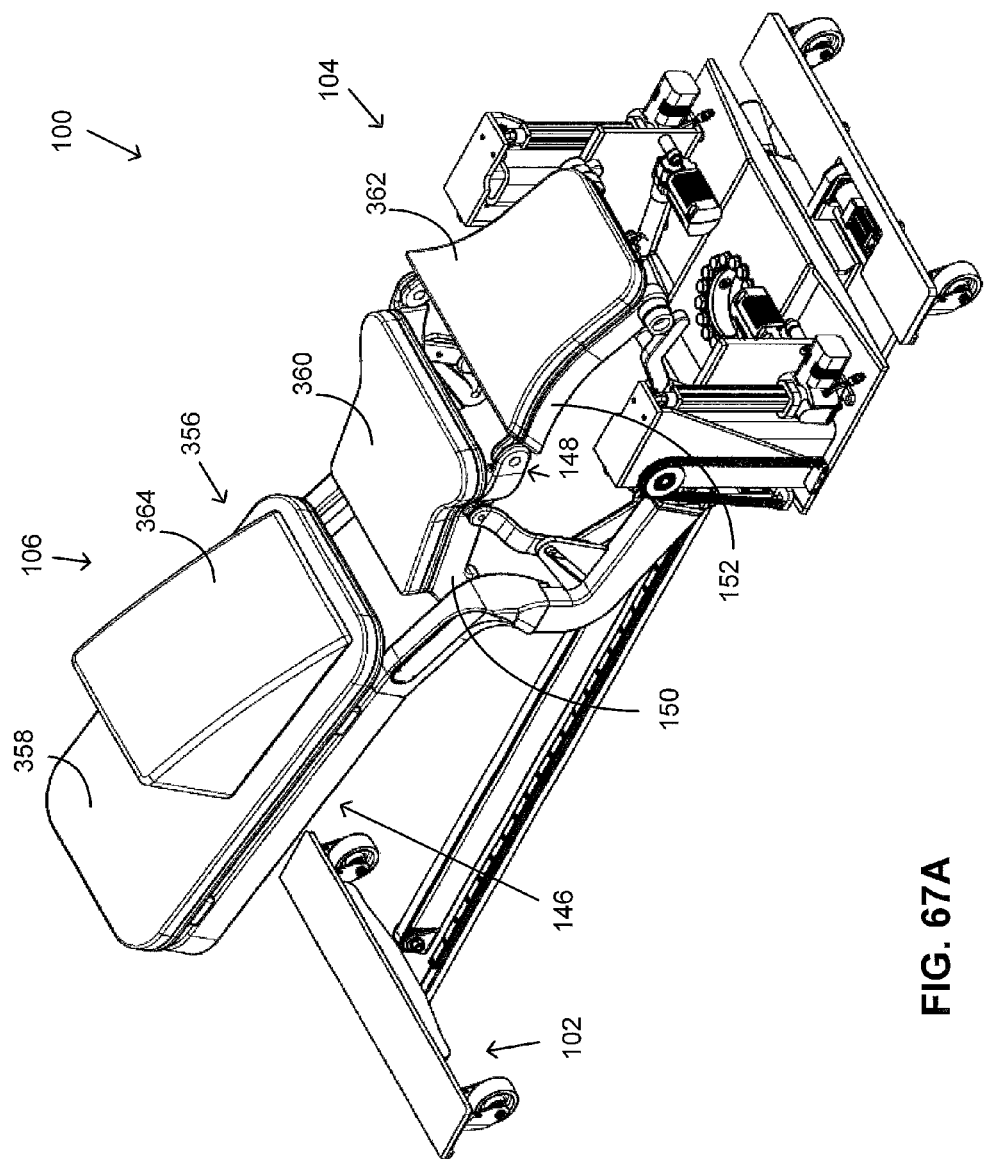
FIG. 67A is an isometric foot end view of the surgical table of FIG. 1, except the table of FIG. 67A includes flat-top pads and supports for positioning a patient in a seated position, for example.

As mentioned previously and now referring to FIGS. 66-67, the surgical table 100 may include alternative pads, cushions, and supports to support a patient on the patient support 106 in a multitude of positions. As seen in FIG. 66, which is an isometric view of the surgical table 100 in a neutral position, the patient support 106 is fitted with a set of flat-top pads 356 to support a patient in a number of positions, including, but not limited to supine, lateral decubitus, and seated. As seen in FIGS. 66-67, the flat-top pads 356 include an upper body pad 358 removably positioned on the rigid outer frame 146 (e.g., with Velcro), an upper leg pad 360 removably positioned on the upper leg member 150 of the inner frame 148, and a lower leg pad 362 removably positioned on the lower leg member 152 of the inner frame 148. As seen in FIG. 67A, additional pillows or cushions 364 may be used with the flat-top pads 356 of the patient support 106 to aid in the patient being positioned in a seated position, for example. Other arrangements of pillows, cushions, and pads are possible and contemplated by the present disclosure.

As seen in FIG. 67A, the upper and lower leg members 150, 152 are rotated (i.e., on a topside angle) beyond or greater than one hundred eighty degrees, relative to each other, so as to accommodate a patient's lower body being in a seated position with the knees bent. As shown and discussed previously with respect to FIGS. 44-45 and 58-59, among others, the upper and lower leg members 150, 152 are generally parallel to each other when the patient support 106 is in an extended position. That is, the upper and lower leg members 150, 152 are prevented from rotating past one hundred eighty degrees, relative to each other, but are permitted to rotate less than one hundred eighty degrees into flexion, for example and as shown in FIGS. 42-43 and 60-63, among others. To prevent rotation of the upper and lower leg members 150, 152 beyond one hundred eighty degrees, the hinge 154 may include a pull-pin, push-pin, or other device (not shown) that prevents or locks the leg members from rotating beyond one hundred eighty degrees relative to each other. The pull-pin, for example, may be engaged with the hinge 154 to prevent rotation and disengaged with the hinge 154 to allow passive rotation of the leg members 150, 152 beyond one hundred eighty degrees. Thus, FIG. 67A shows an exemplary embodiment of the surgical table 100 where the pull-pin may be disengaged to allow the leg members to rotate beyond one hundred eighty degrees to position the inner frame 148 in a seated position. Once the inner frame 148 is set to a desired angle between the upper and lower leg members 150, 152, the pull-pin may be re-engaged or re-inserted into the hinge 154 to lock the leg members in the desired orientation/angle. Other mechanisms are possible to accomplish the function of limiting rotation at the hinge 154 while allowing rotation at the hinge 154 under certain circumstances. It is foreseen that other mechanisms besides a push-pin or pull-pin may be utilized to accomplish this. For example, the hinge may be electronically controlled with sensors and actuators that are controlled by a user device such as, for example, a computer or hand-held controller.

Figure 67B:
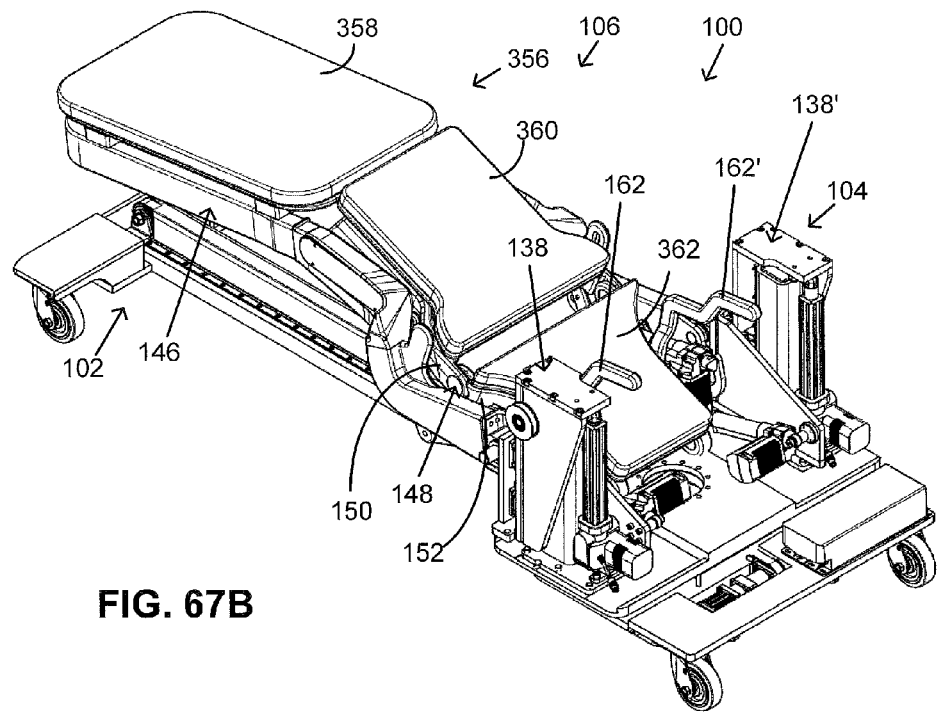
FIG. 67B is an isometric foot end view of the surgical table of FIG. 1, except the table of FIG. 67B includes flat-top pads and supports for positioning a patient in a lateral decubitus position, for example.
Figure 67C:
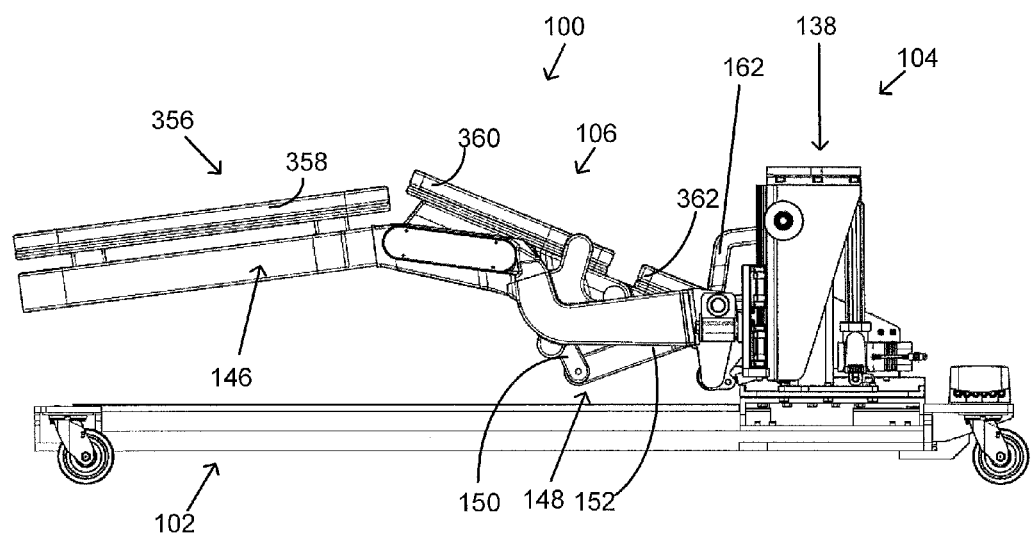
FIG. 67C is a side view of the table of FIG. 67B.

Reference is now made to FIGS. 67B and 67C, which are, respective, isometric foot end and side views of the surgical table of as shown in FIG. 67A, except the table of FIG. 67B does not include the pillows or cushions 364 and the patient support 106 is positioned to support a patient in a lateral decubitus position. In this position, the patient (not shown) may be lying on his or her side. The inner frame 148 of the patient support 106 is partially flexed at the joint 158 to accommodate the patient's hips. In particular, the upper leg member 150 is angled downward relative to the outer frame 146 and the lower leg member 152 is generally parallel to the upper leg member 150. To facilitate the lower leg pad 362 being positioned between the column assemblies 138, 138', as seen in the figures, the guide bushings 304 are removed such that the lower leg member 152 is not guided by the guide members 162, 162'.

As seen with reference to the flexed position of the patient support 106 in FIGS. 42-43 and 60-63, among others, the inner frame 148 is configured to articulate at the joint or hinge 154 when the upper leg member 150 articulates at the sliding hinge 158 relative to the outer frame 146 at angles (i.e., topside angles) greater than about one hundred eighty degrees. That is, when the upper leg member 150 rotates downward relative to the outer frame 146, the lower leg member 152 also rotates towards the upper leg member 150 so as to position a patient in flexion. Turning back to FIGS. 67B and 67C, and similarly described with reference to the seated position, in FIG. 67A, a pull-pin, push-pin, or other mechanism (not shown) may be utilized to allow the lower leg member 152 to remain parallel to the upper leg member 150 when the inner frame 148 is angled downward at the hinge 158 relative to the outer frame 146 (i.e., instead of articulating into flexion about the hinge 154). The pull-pin, for example, may cause the upper and lower leg members 150, 152 to articulate relative to each other when the pin is inserted or engaged with the hinge 154. Disengagement of the pull-pin with the hinge 154 may allow the upper and lower leg members 150, 152 to freely or passively rotate relative to each other. Thus, a surgeon may disengage the pull-pin from the hinge 154 and position the lower leg member 152 to be parallel to the upper leg member 150, as shown in the figures, and then the surgeon may re-engage the pull-pin with the hinge 154 to lock the position of the leg members 150, 152 in place. As with the discussion above, it is foreseen that many different mechanisms may accomplish the functions described herein and the present disclosure is not limited to a pull-pin or push-pin.

The following is a brief discussion of a possible clinical use of the surgical table 100 described herein with reference to the various figures. For a particular surgical procedure on a patient requiring access to the thoracic and lumbar spine of the patient, the surgical table 100 may be configured with chest pads 266 on the torso assembly 246 and hip and pelvic pads 274 on the winged members 280 of the upper leg member 150 of the inner frame 148 to position the patient in a prone position. A sling may additionally be positioned between the lower leg members 152 of the inner frame 148 to support the patient's lower legs in place during articulation of the inner frame 148 relative to the outer frame 146. To begin the procedure, the patient is, typically, anesthetized on a stretcher or gurney and, then, rolled onto the patient support 106 of the surgical table 100 and into a prone position. At this point, the torso assembly 246 may be slid into proper placement such that the patient's sternum is securely supported on the chest pad 266. The hip pads may be properly positioned underneath the patient's pelvis and then the torso assembly 246 may be locked in place. The patient's lower body may then be carefully manipulated at the hips and knees to ensure that the torso region of the patient remains stationary and that the fixed distance X between points on the pads Y, Z remains constant. That is, it is important to ensure that the patient's spine is not distacted or compressed during flexion and extension. If needed, adjustments may be made to the patient's positioning on the various pads at this time. The torso assembly 246 may also be longitudinally adjusted, if necessary. Once the patient's lower body can be manipulated without movement of the torso region and without compressing or distracting the patient's spine, the procedure may continue according to the specifics of the particular procedure.

III. The Surgical Table—Dual Column

For a description of another example of a surgical table 1000 for positioning and supporting a patient during medical procedures, such as surgery and imaging, reference is made to FIGS. 68-80. In one implementation, the table 1000 includes a base assembly or base 1002 supported on a floor surface, a patient support structure or patient support 1004, and a pair of centrally offset and opposing end support or support column assemblies 1006, 1008. The patient support 1004 is detachable from the end support column assemblies 1006, 1008 for convenient swapping of different patient supports 1004. Since the patient support 1004 described herein includes mechanisms to articulate the lower body of the patient with respect to the upper body of the patient, the base 1002 and end support columns 1006, 1008 do not need any mechanisms to articulate the patient in this way. Rather, the base 1002 and the end support columns 1006, 1008 need only be able to lift the ends of the patient support 1004, rotate the patient support 1004, and provide for longitudinal compensation when the patient support 1004 is raised at different heights by the opposing outer end support columns 1006, 1008.

Figure 68:
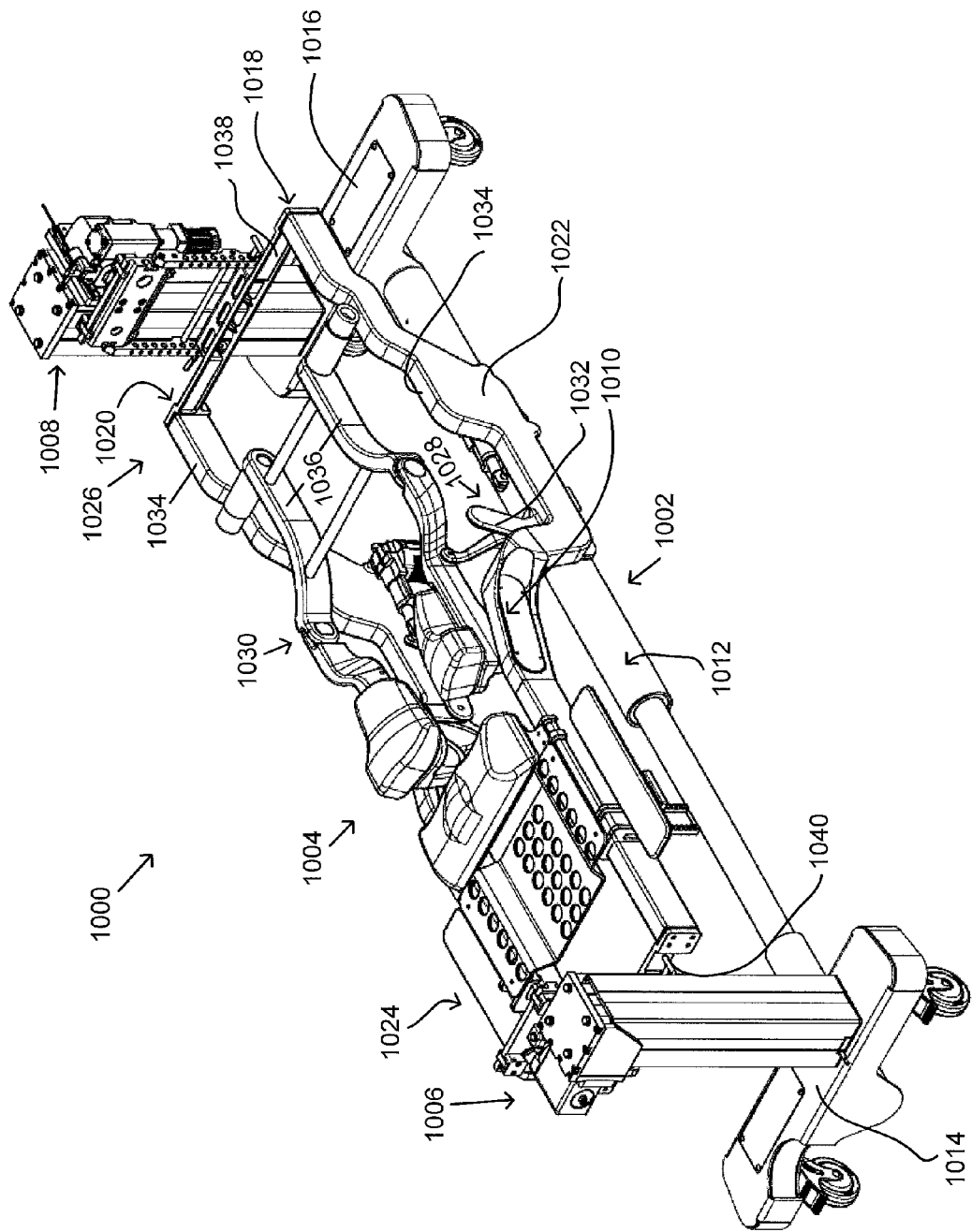
FIG. 68 is an isometric head end view of another example surgical table with a patient support extending from a pair of centrally offset support columns, wherein the patient support is shown in a neutral position.

To begin, reference is made to FIG. 68, which shows an isometric head end view of the surgical table 1000 with the patient support 1004 in a neutral position. The neutral position is defined by the patient support 1004 being generally level. That is, there is generally no rotation about a longitudinal axis of the patient support 1004 or about a transverse axis extending through an area near the hinges 1010.

As seen in FIG. 68, the base assembly 1002 includes a telescoping assembly 1012 including one or more telescoping members extending between a head end support member 1014 and a foot end support member 1016. The head and foot end support members 1014, 1016 are supported on lockable caster wheels.

The patient support 1004 is similar to the patient support previously described in reference to FIGS. 36-63, among others, and the discussion of its various components and features are incorporated into the present discussion. The patient support 1004 can be generally divided into a left side 1018 and a right side 1020, which is mostly a mirror of the left side 1018. Both the left and right sides 1018, 1020 include a rigid outer frame 1022 that is supported at a head end 1024 and a foot end 1026 of the patient support 1004 by the, respective, head end and foot end support column assemblies 1006, 1008. The hinge 1010 and the linkage and drive assembly 1028 for articulating an inner flexible, lower leg, frame 1030 is similar to the previously described embodiments, except that the cam path plate 1032 is integrally formed with the rigid outer frame 1022.

Still referring to FIG. 68, the rigid outer frame 1022 includes integrated guide members 1034 for the inner frame 1030 to guide the articulation of the lower leg members 1036 as the inner frame 1030 articulates into flexion (not shown), for example. Otherwise, the shape and function of the guide members 1034 is the same as previously described. In the present embodiment, a foot end of the guide members 1034 is coupled to the foot end support column assembly 1008 via a foot end bracket 1038. On the opposite end of the patient support 1004, the head end 1024 of the patient support 1004 is coupled to the head end support column assembly 1006 via a head end bracket 1040. The patient support 1004 is detachable from the head and foot end support columns 1006, 1008 at their respective brackets 1040, 1038.

Figure 69:
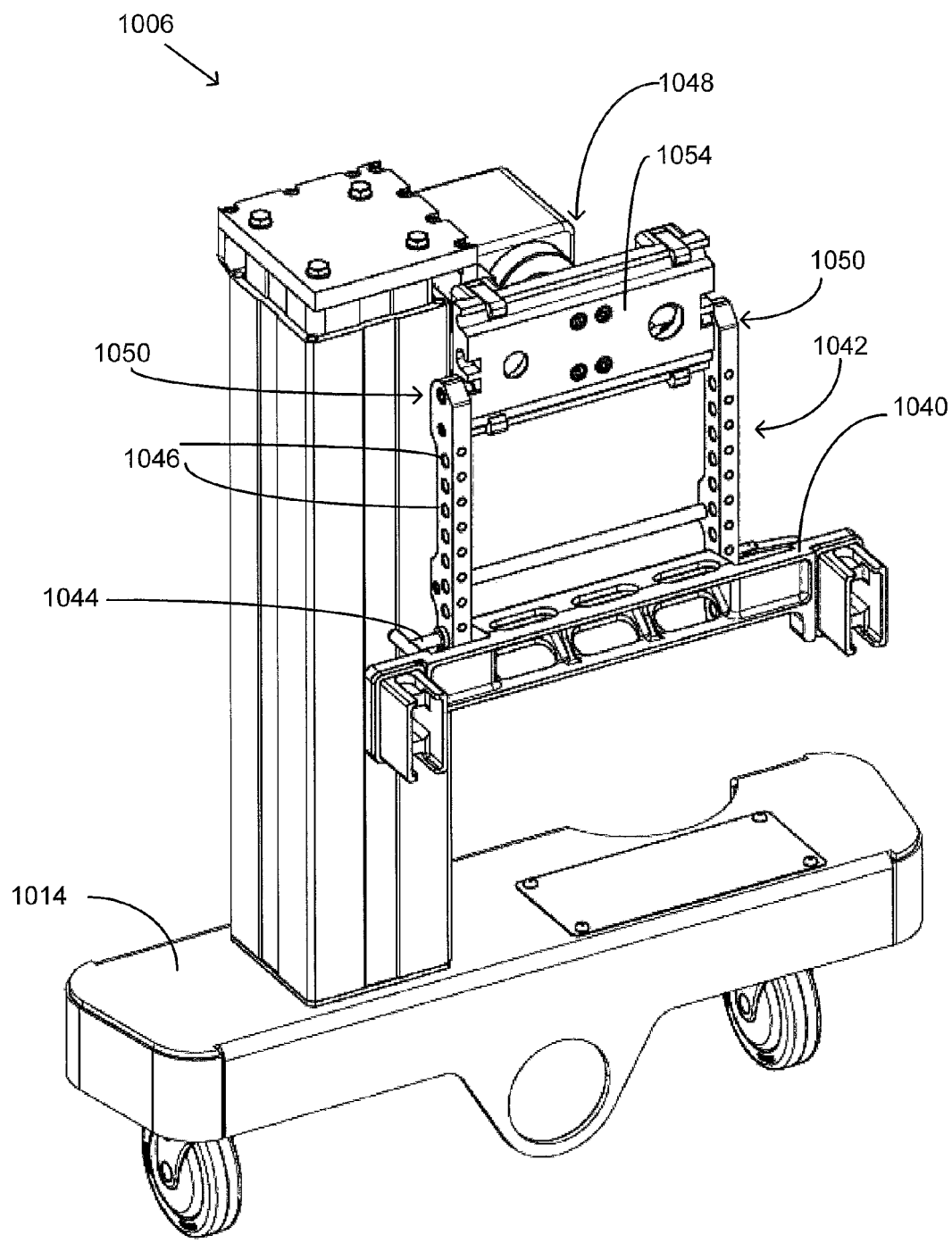
FIG. 69 is an isometric front view of a head end support column assembly of the surgical table of FIG. 68.
Figure 70:
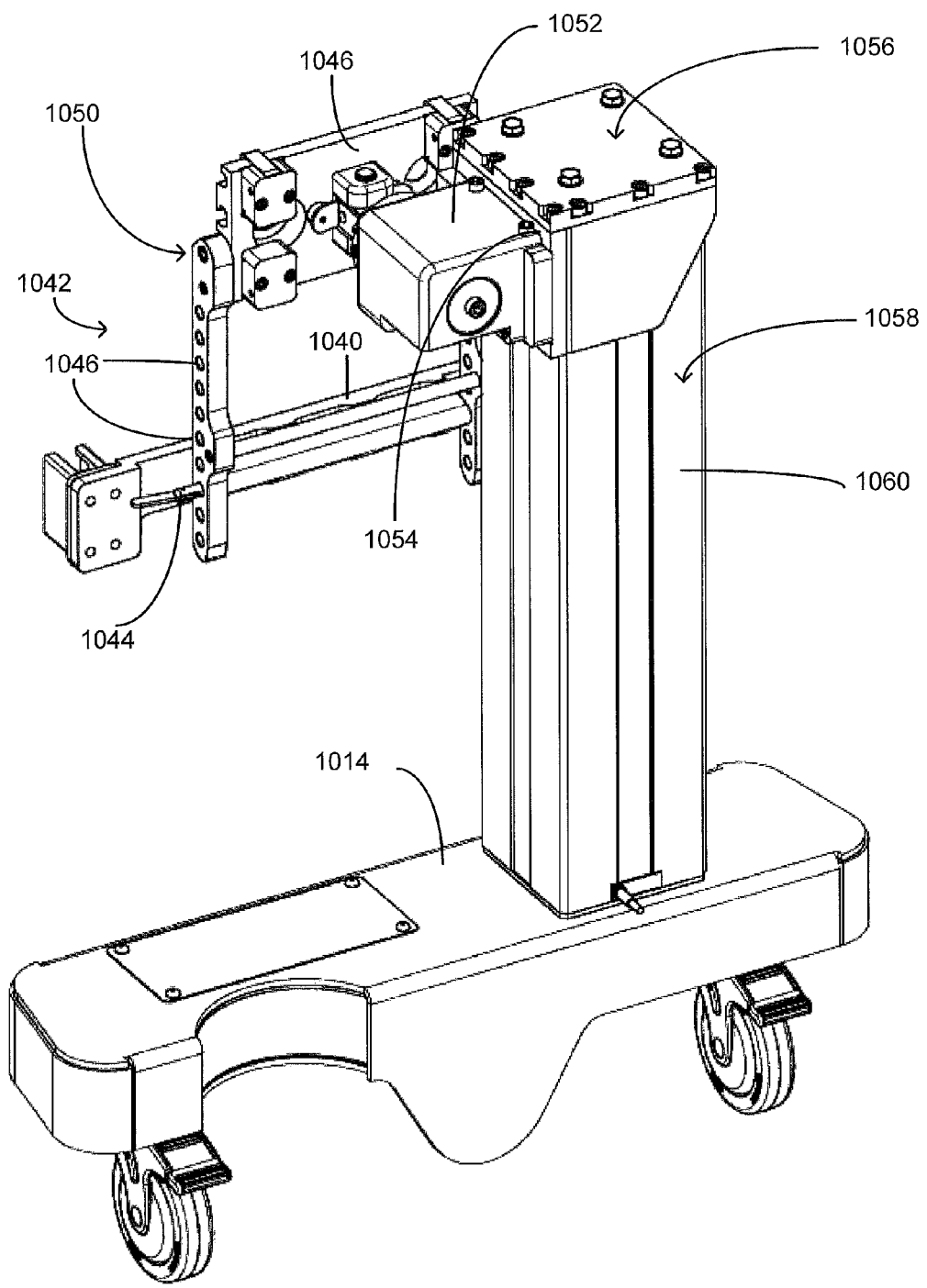
FIG. 70 is an isometric rear view of the head end support column assembly of the surgical table of FIG. 68.

Reference is now made to FIG. 69, which is a front isometric view of the head end support column 1006 with the telescoping assembly 1012 and the patient support 1004 hidden from view. As seen in the figure, the bracket 1040 supporting the head end 1024 of the patient support 1004 is pivotally coupled to an H-bar frame member 1042 at a lower end of the member via a pin 1044. The pin 1044 may be positioned within a variety of through holes 1046 in the H-bar frame member 1042 to raise or lower the head end 1024 of the patient support 1004 prior to a surgical procedure. A top end of the H-bar frame member 1042 is pivotally coupled with a mounting plate 1054 of a rotation subassembly 1048 at pins or screws 1050. Turning to FIG. 70, which is a back isometric view of the head end support column 1006, the mounting plate 1046 is rotationally coupled with a shaft of a motor 1052 near a center point of the plate 1046 such that the mounting plate 1046 and, thus, the H-bar frame member 1042, bracket 1040, and the patient support 1004 can rotate around a longitudinal axis of the patient support 1004.

As seen in FIGS. 69-70, the motor 1052 is coupled to a side plate 1054 of a mounting structure 1056 that couples the rotation subassembly 1048 to a vertical lift assembly 1058 including telescoping members 1060 that are driven by linear actuators within the members 1060. As seen in the figure, the rotation subassembly 1048 is coupled to a side portion of the vertical lift assembly 1058. In this way, the linear actuators may be activated to raise or lower the mounting structure 1056, which, in turn, raises and lowers the rotation subassembly 1048 and the head end 1024 of the patient support 1004. The rotation subassembly 1048 and vertical lift assembly 1058, among other components, are described in other applications, such as, for example, U.S. patent application Ser. No. 7,565,708, filed Apr. 20, 2007, entitled PATIENT POSITIONING SUPPORT STRUCTURE, which is hereby incorporated by reference in its entirety. And while the foot end support column 1008 and the head end support column 1006 are described in a certain way, the columns 1008, 1006 may be differently configured. For example, the support columns 1006, 1008 may be similar to the head and foot end supports of the surgical table in U.S. Provisional Patent Application No. 62/021,630, filed on Jul. 7, 2014, titled "SURGICAL TABLE WITH PATIENT SUPPORT HAVING FLEXIBLE INNER FRAME SUPPORTED ON RIGID OUTER FRAME", which is hereby incorporated by reference in its entirety into the present application. For example, the support columns 1008, 1006 in the present application may include powered pitch assemblies, as described in the incorporated application.

Figure 71:
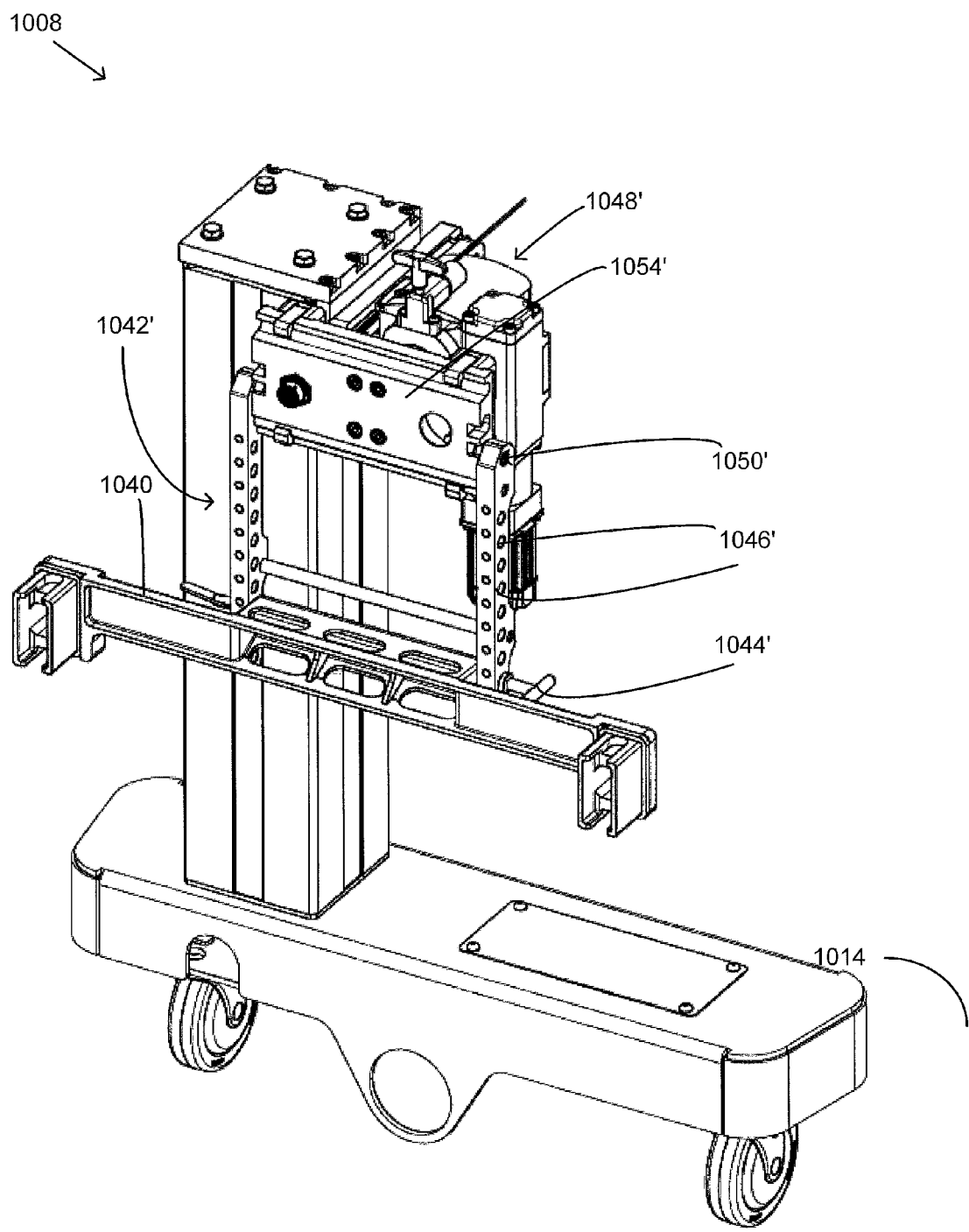
FIG. 71 is an isometric front view of a foot end support column assembly of the surgical table of FIG. 68.
Figure 72:
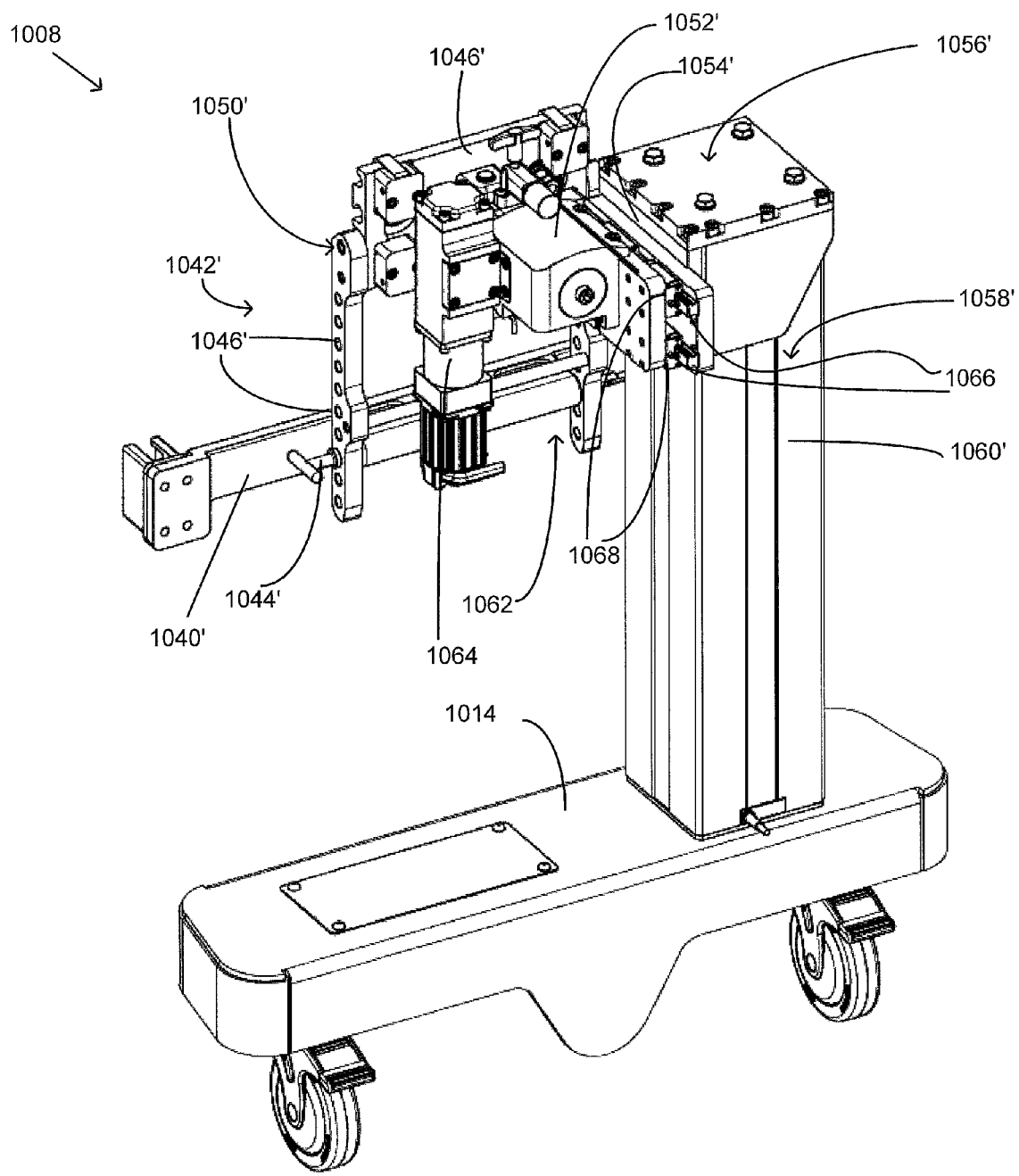
FIG. 72 is an isometric rear view of the foot end support column assembly of the surgical table of FIG. 68.

Reference is now made to FIG. 71, which is a front isometric view of the foot end support column 1008 with the telescoping assembly 1012 and the patient support 1004 hidden from view. As seen in the figure, the bracket 1038 supporting the foot end 1026 of the patient support 1004 is pivotally coupled to an H-bar frame member 1042' at a lower end of the member via a pin 1044'. The pin 1044' may be positioned within a variety of through holes 1046' in the H-bar frame member 1042' to raise or lower the foot end 1026 of the patient support 1004 prior to a surgical procedure. A top end of the H-bar frame member 1042' is pivotally coupled with a mounting plate 1054' of a rotation subassembly 1048' at pins or screws 1050'. Turning to FIG. 72, which is a back isometric view of the foot end support column 1008, the mounting plate 1046' is rotationally coupled with a shaft of a motor 1052' near a center point of the plate 1046' such that the mounting plate 1046' and, thus, the H-bar frame member 1042', bracket 1040', and the patient support 1004 can rotate around a longitudinal axis of the patient support 1004.

As seen in FIGS. 71-72, the motor 1052' is coupled to a side plate 1054' of a mounting structure 1056' that couples the rotation subassembly 1048' to a vertical lift assembly 1058' including telescoping members 1060' that are driven by linear actuators within the members 1060'. In this way, the linear actuators may be activated to raise or lower the mounting structure 1056', which, in turn, raises and lowers the rotation subassembly 1048' and the head end 1024 of the patient support 1004.

Continuing with FIGS. 71-72, the foot end support column 1008 includes a translational compensation mechanism 1062 that facilities the rotation subassembly 1048', along with the H-bar frame member 1042', bracket 1040', and the foot end 1026 of the patient support 1004 translating or moving toward and away from the opposite support column 1006 when the vertical lift assemblies 1058, 1058' are actuated in such a way as to tilt the patient support 1004 about a transverse axis of the patient support. That is, when the vertical lift assemblies 1058, 1058' are lifted to differing heights, the patient support 1004 will not be in a neutral position, but be titled so as to be non-perpendicular with respect to the support columns 1006, 1008.

The translational compensation mechanism 1062 moves toward and away from the opposing end support column 1006 because the patient support 1004 is of a fixed length and a horizontal distance between the brackets 1040, 1040' is longest when the patient support is in the neutral position (i.e., perpendicular with the end support columns 1006, 1008). When the patient support 1004 is rotated or pivoted about a transverse axis to the longitudinal axis of the patient support 1004 (i.e., when the vertical list assemblies 1058, 1058' are at different heights), the horizontal distance between the brackets 1040, 1040' is shortened (i.e., in this instance, the longitudinal axis of the patient support is the hypotenuse of a triangle, which is longer than the horizontal distance). Thus, when the patient support 1004 is in the neutral position (i.e., the longest horizontal distance), the translational compensation mechanism 1062 is configured to position the rotation subassembly 1048', the H-bar frame member 1042', bracket 1040', and the foot end 1026 of the patient support 1004 at its furthest position away from the opposing end support column 1006.

Figure 73:
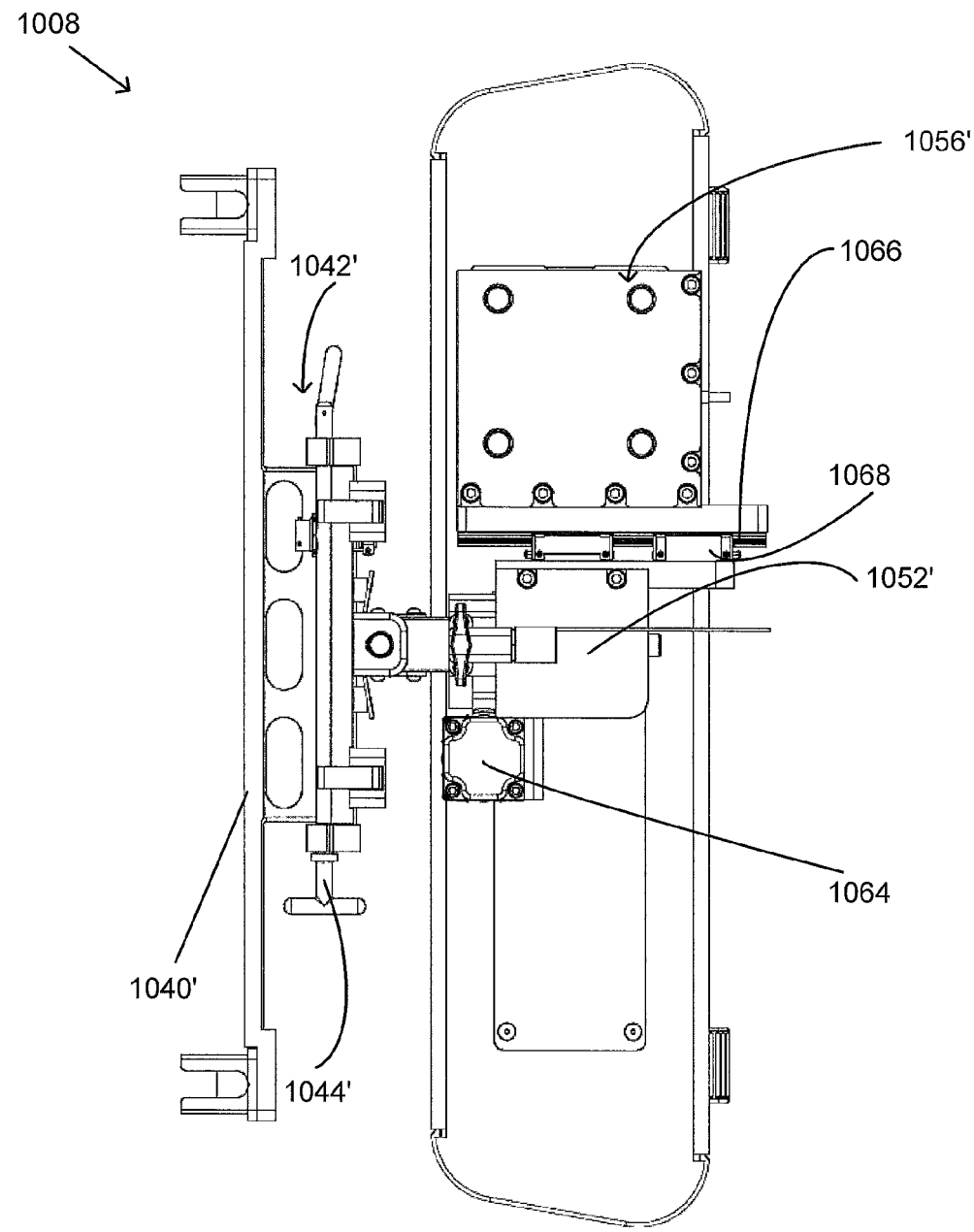
FIG. 73 is a top view of the foot end support column assembly of the surgical table of FIG. 68.

As seen in FIGS. 71-73, the translational compensation mechanism 1062 includes a motor 1064, two rails 1066 on a plate that is coupled to the side plate 1054', and four carriages 1068 on a plate that are movably coupled to the rails 1066 on one side and the motor 1052' of the rotation subassembly 1048 on the other side. In this way, the motor 1064 can cause the rotation subassembly 1048', H-bar frame member 1042', bracket 1040', and the foot end of 1026 of the patient support 1004 to translate via the carriages 1068 on the rails 1066 toward and away from the opposing end support 1006 to compensate for the changing horizontal distance between the head and foot ends 1024, 1026 of the patient support 1004 when the patient support 1004 is pivoted about an axis transverse to a longitudinal axis of the patient support 1004.

Figure 74:
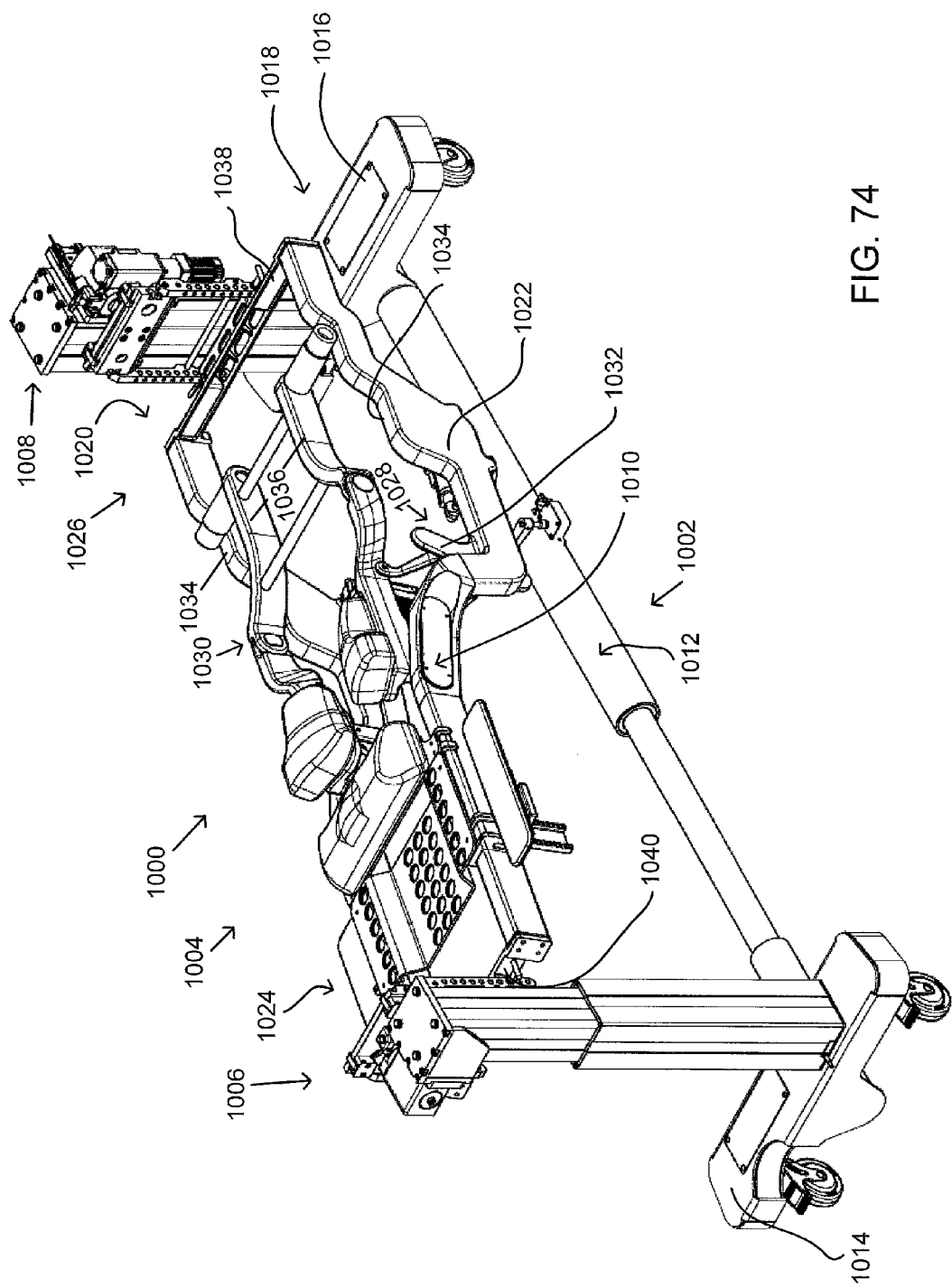
FIG. 74 is an isometric head end view of the surgical table of FIG. 68, wherein the patient support is shown in reverse Trendelenburg.

Turning to FIG. 74, which is an isometric head end view of the surgical table 1000 with the patient support 1004 in reverse Trendelenburg, the head end 1024 of patient support 1004 lifted about the foot end 1026. In this position, the vertical lift assembly 1058 and, in particular, the telescoping members 1060 of the head end support column 1006 are vertically raised by the linear actuators higher than the vertical lift assembly 1058' on the foot end support column 1008.

Figure 75:
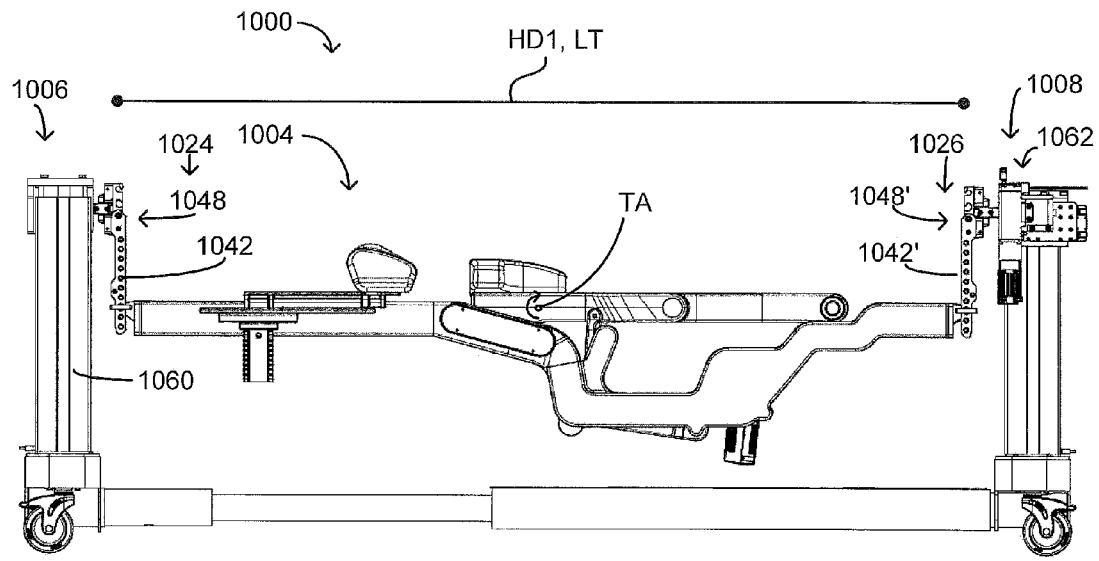
FIGS. 75 and 76 are respective side views of the surgical table of FIG. 68, wherein the patient support is shown in a neutral position and in reverse Trendelenburg.
Figure 76:
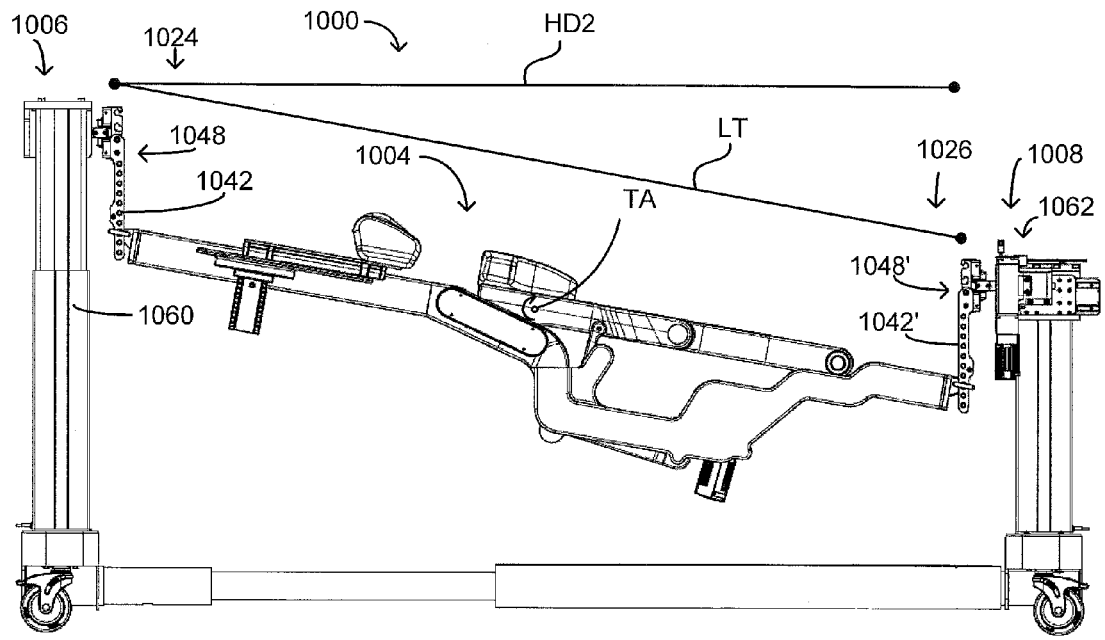

Reference is made to FIGS. 75-76, which are, respective, side views of the surgical table 1000 with the patient support 1004 in a neutral position and reverse Trendelenburg. As seen in these FIG. 75, the head end support column 1006 and the foot end support column 1008 are at equal heights such that the patient support 1004 is generally level with the floor and generally perpendicular to the end support columns 1006, 1008. In this position, the patient support 1004 is not pivoted relative to a transverse axis TA of the patient support 1004. In contrast, the patient support 1004 of FIG. 76 is rotated clockwise about the transverse axis TA by the telescoping members 1060 of the head end support column 1006 vertically extending via the linear actuators such that the head end 1024 of the patient support 1004 is positioned above the foot end 1026 of the patient support 1004. In this position, the rotation subassembly assembly 1048, and the H-bar frame member 1042, among other components at the top of the head end support column 1006 are also positioned above the rotation subassembly 1048', the H-bar frame member 1042', among the other components at the top of the foot end support column 1008. As seen in the figure, the H-bar frame members 1042, 1042' passively act at the pins 1044, 1044', 1050, 1050', but the translational compensation mechanism 1062 translates appropriately such that the H-bar frame members 1042, 1042' remain substantially parallel to each other.

As seen in FIG. 75, the translational compensation mechanism 1062 is positioned in an aft or rearward position. The horizontal distance HD1 between the head and foot ends 1024, 1026 of the patient support 1004 (shown in FIGS. 75 and 76 as the horizontal distance between the pins 1044, 1044') is at its maximum in this position and is equal to the length LT of the patient support 1004. In contrast, the translational compensation mechanism 1062 is translated to a fore or forward position when the patient support 1004 is pivoted about the transverse axis TA, as seen in FIG. 76. The horizontal distance HD2 between the head and foot ends 1024, 1026 of the patient support 1004 is decreased in this position. The amount of change in the distance between HD1 and HD2 is a simple trigonometric function based on the length LT of the patient support 1004 and the angle of pivot about the transverse axis TA.

Figure 77:
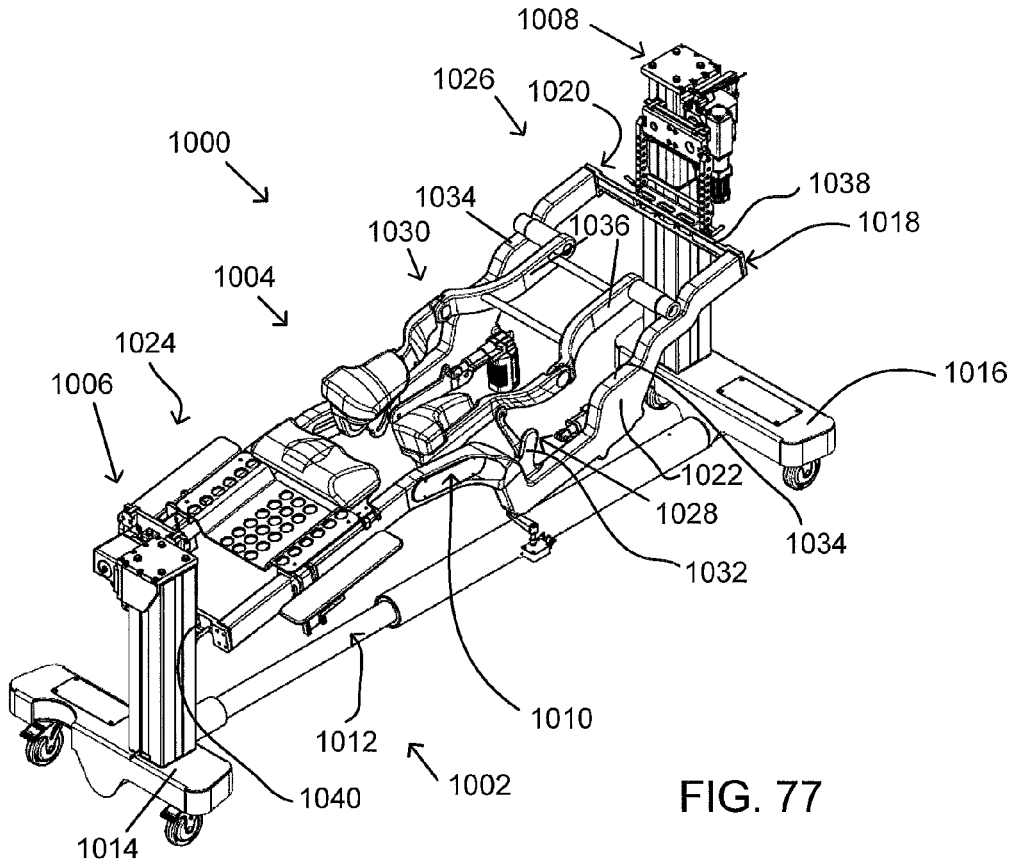
FIG. 77 is an isometric head end view of the surgical table of FIG. 68, wherein the patient support is shown in Trendelenburg.
Figure 78:
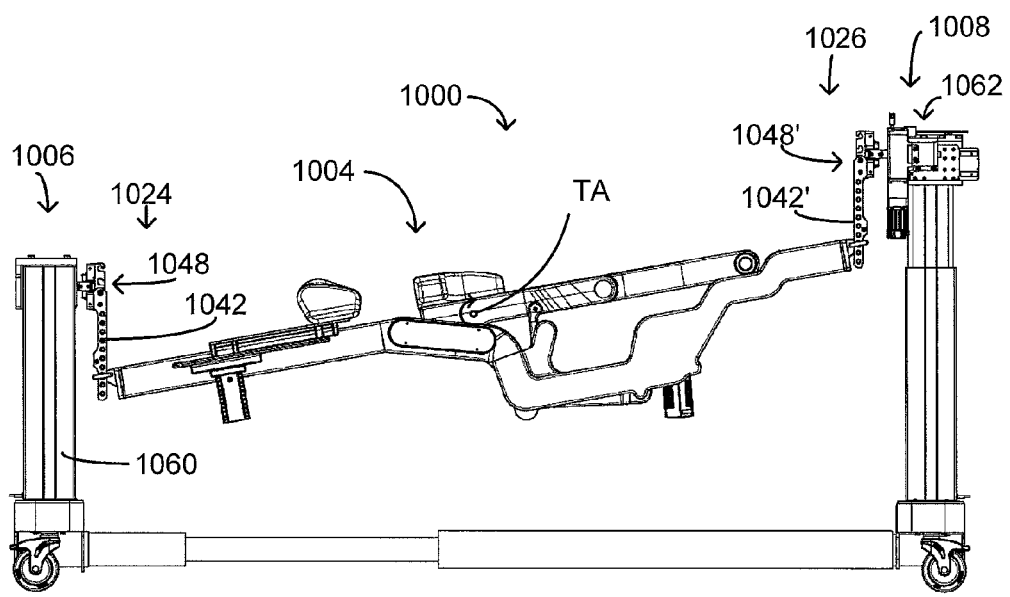
FIG. 78 is a side view of the surgical table as shown in FIG. 77.

The surgical table 1000 may function to position a patient in Trendelenburg, as seen in FIGS. 77-78, which are, respective, head end isometric and side views of the surgical table 1000. In this position, the foot end support column 1008 is raised via the linear actuators in the telescoping members 1060' of the vertical lift assembly 1058' such that foot end 1026 of the patient support 1004 is positioned higher than the head end 1024 of the patient support 1004. In this position, the patient support 1004 is rotated counterclockwise (from the neutral position) about the transverse axis TA. As seen in FIG. 78, the translational compensation mechanism 1062 is positioned in a forward or fore position to compensate for the decreased length of the horizontal distance between of the patient support 1004.

Figure 79:
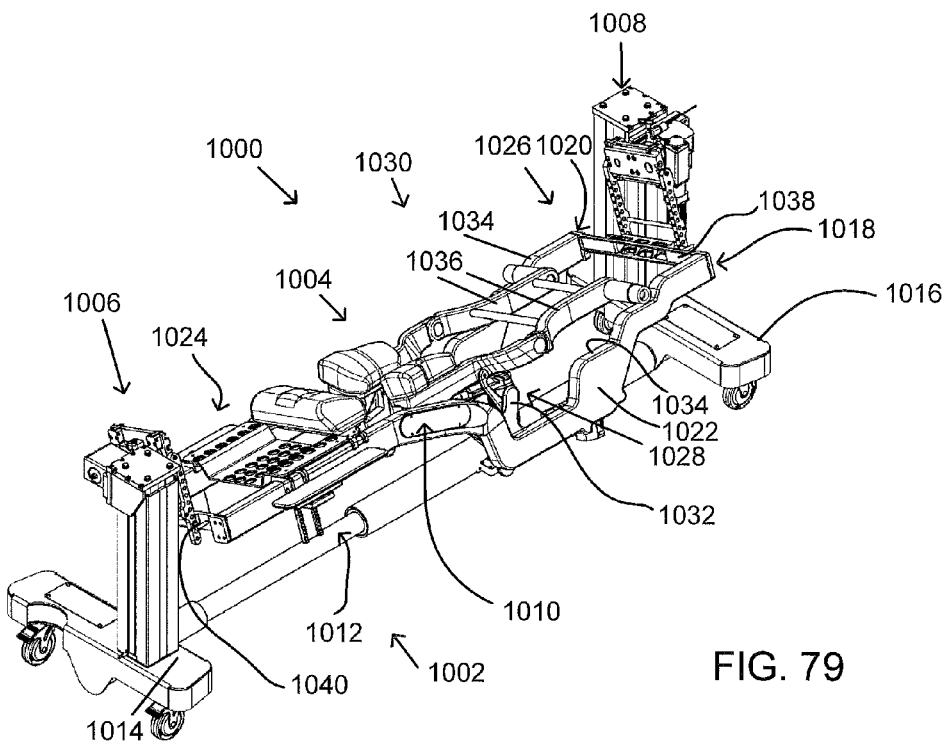
FIG. 79 is an isometric head end view of the surgical table of FIG. 68, wherein the patient support is shown tilted about a longitudinal axis of the patient support.
Figure 80:
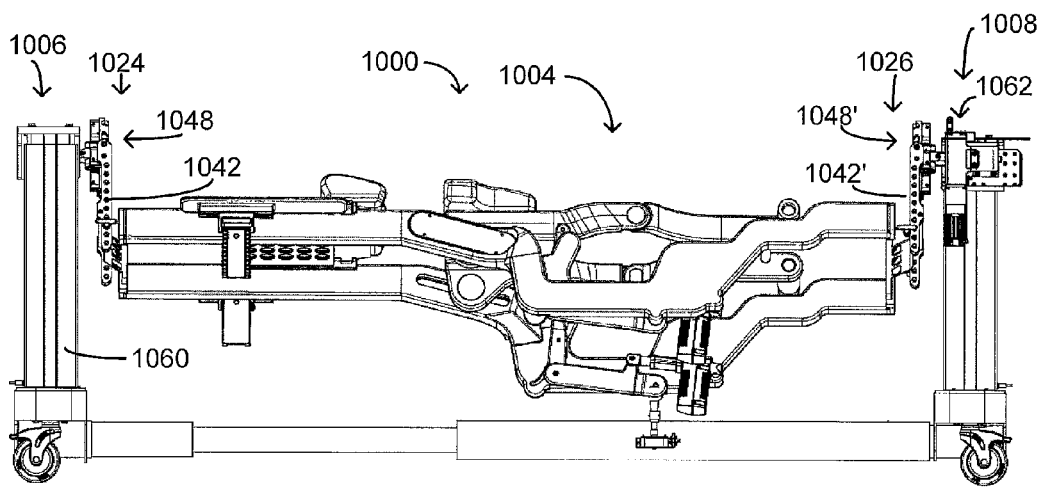
FIG. 80 is a side view of the surgical table as shown in FIG. 79.

FIGS. 79 and 80 depict, respective, head end isometric and side views of the surgical table 1000 in a tilted or rolled position. In particular, the patient support 1004 is rotated about a longitudinal axis of the patient support extending between the head and foot ends 1024, 1026 of the patient support 1004. As seen in the figures, the rotation subassemblies 1048, 1048' are positioned above the outer ends 1024, 1026 of the patient support 1004 and are configured to pivot, rotate, or roll the patient support from a neutral position 180 degrees, 360 degrees, or any other degree, about the longitudinal axis of the patient support 1004.

As seen in FIGS. 68-74, among others, the head end support column 1006 and the foot end support column 1008 are laterally offset or off-center from a center point on their respective head end support member 1014 and foot end support member 1016. This enables the rotation subassembly 1048, 1048' to be positioned beside the telescoping members 1060, 1060' instead of in front of, on top of, or inside a portion of the telescoping members 1060, 1060'.

Referring to these figures, the H-bar frame members 1042, 1042', function as an angulation assembly to facilitate pivoting of the outer ends 1024, 1026 of the patient support 1004. The translational compensation mechanism 1062 acts such that the H-bar frame members 1042, 1042' may remain substantially perpendicular to the floor and substantially parallel to the support columns while still being passive at the pins 1044, 1044' and 1050, 1050'.

Figure 81:
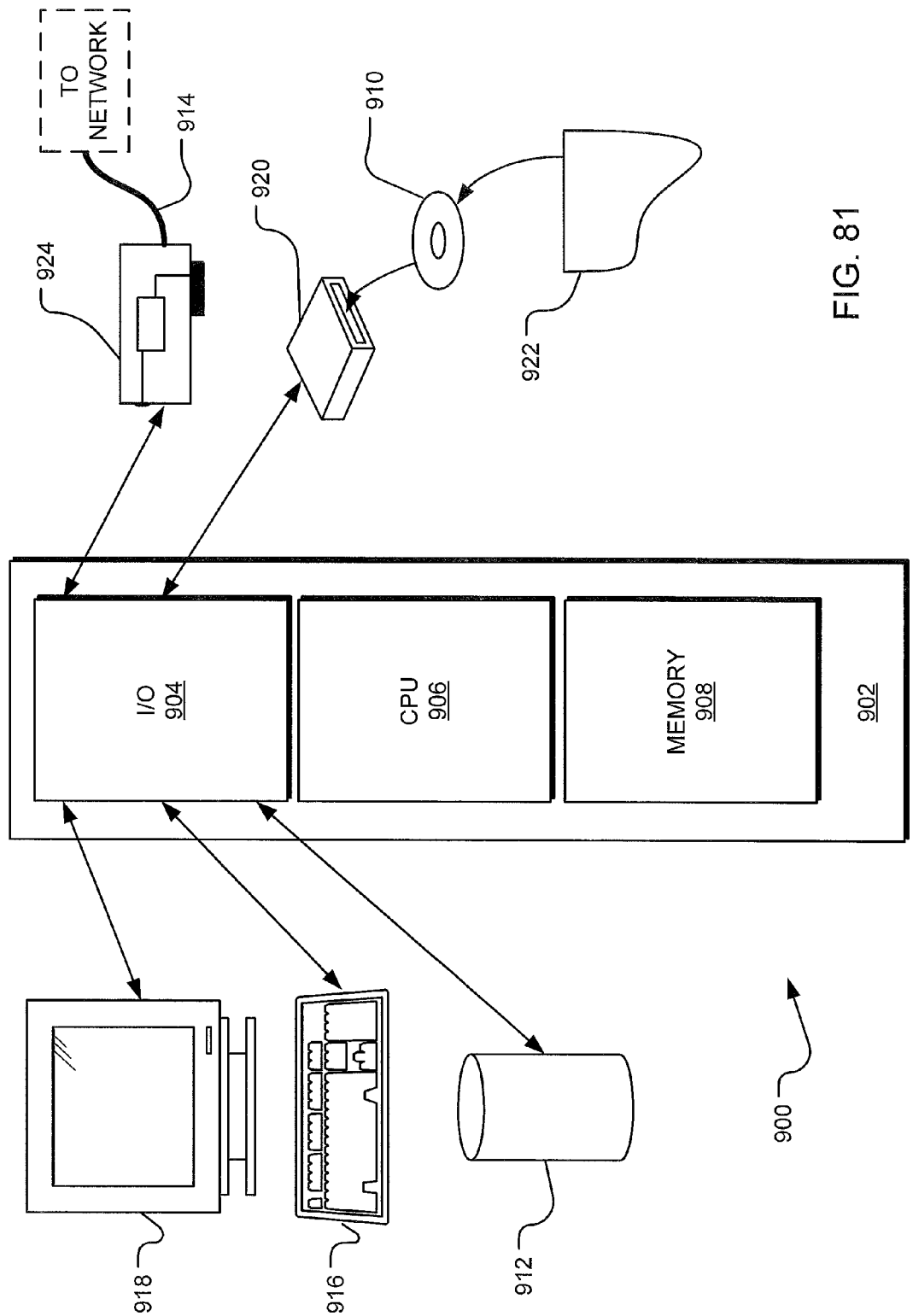
FIG. 81 is an example computing system that may be specifically configured to implement the various systems and methods discussed herein.

Referring to FIG. 81, a detailed description of an example computing system 900 having one or more computing units that may implement various systems and methods discussed herein is provided. The computing system 900 may be applicable to a user device 312, a server in communication with a network, or other computing devices. It will be appreciated that specific implementations of these devices may be of differing possible specific computing architectures not all of which are specifically discussed herein but will be understood by those of ordinary skill in the art.

The computer system 900 may be a general computing system that is capable of executing a computer program product to perform a computer process. Data and program files may be input to the computer system 900, which reads the files and executes the programs therein. Some of the elements of a general purpose computer system 900 are shown in FIG. 66 wherein a processor 902 is shown having an input/output (I/O) section 904, a Central Processing Unit (CPU) 906, and a memory section 908. There may be one or more processors 902, such that the processor 902 of the computer system 900 comprises a single central-processing unit 906, or a plurality of processing units, commonly referred to as a parallel processing environment. The computer system 900 may be a conventional computer, a distributed computer, or any other type of computer, such as one or more external computers made available via a cloud computing architecture. The presently described technology is optionally implemented in software devices loaded in memory 908, stored on a configured DVD/CD-ROM 910 or storage unit 912, and/or communicated via a wired or wireless network link 914, thereby transforming the computer system 900 in FIG. 38 to a special purpose machine for implementing the described operations.

The I/O section 904 is connected to one or more user-interface devices (e.g., a keyboard 916 and a display unit 918), a disc storage unit 912, and a disc drive unit 920. In the case of a tablet, a smart phone device, or similar computing device, there may not be a physical keyboard but rather a touch screen with a computer generated touch screen keyboard. Generally, the disc drive unit 920 is a DVD/CD-ROM drive unit capable of reading the DVD/CD-ROM medium 910, which typically contains programs and data 922. Computer program products containing mechanisms to effectuate the systems and methods in accordance with the presently described technology may reside in the memory section 904, on a disc storage unit 912, on the DVD/CD-ROM medium 910 of the computer system 900, or on external storage devices made available via a cloud computing architecture with such computer program products, including one or more database management products, web server products, application server products, and/or other additional software components. Alternatively, a disc drive unit 920 may be replaced or supplemented by an optical drive unit, a flash drive unit, magnetic drive unit, or other storage medium drive unit. Similarly, the disc drive unit 920 may be replaced or supplemented with random access memory (RAM), magnetic memory, optical memory, and/or various other possible forms of semiconductor based memories.

The network adapter 924 is capable of connecting the computer system 900 to a network via the network link 914, through which the computer system can receive instructions and data. Examples of such systems include personal computers, Intel or PowerPC-based computing systems, AMD-based computing systems and other systems running a Windows-based, a UNIX-based, or other operating system. It should be understood that computing systems may also embody devices such as terminals, workstations, personal computers, mobile phones, tablets or slates, multimedia consoles, gaming consoles, set top boxes, etc.

When used in a LAN-networking environment, the computer system 900 is connected (by wired connection or wirelessly) to a local network through the network interface or adapter 924, which is one type of communications device. When used in a WAN-networking environment, the computer system 900 typically includes a modem, a network adapter, or any other type of communications device for establishing communications over the wide area network. In a networked environment, program modules depicted relative to the computer system 900 or portions thereof, may be stored in a remote memory storage device. It is appreciated that the network connections shown are examples of communications devices for and other means of establishing a communications link between the computers may be used.

In an example implementation, table articulation data, imaging data, patient data, a plurality of internal and external databases, source databases, and/or cached data on servers are stored as the memory 908 or other storage systems, such as the disk storage unit 912 or the DVD/CD-ROM medium 910, and/or other external storage devices made available and accessible via a network architecture. Table articulation software, imaging software, and other modules and services may be embodied by instructions stored on such storage systems and executed by the processor 902.

Some or all of the operations described herein may be performed by the processor 902. Further, local computing systems, remote data sources and/or services, and other associated logic represent firmware, hardware, and/or software configured to control operations of the table 100, the user device 312, and/or other computing units or components in communication with the table 100 and/or the user device 312. Such services may be implemented using a general purpose computer and specialized software (such as a server executing service software), a special purpose computing system and specialized software (such as a mobile device or network appliance executing service software), or other computing configurations. In addition, one or more functionalities disclosed herein may be generated by the processor 902 and a user may interact with a Graphical User Interface (GUI) using one or more user-interface devices (e.g., the keyboard 916, the display unit 918, and the user device 312). The system set forth in FIG. 66 is but one possible example of a computer system that may employ or be configured in accordance with aspects of the present disclosure.

In the present disclosure, the methods disclosed may be implemented as sets of instructions or software readable by a device. Further, it is understood that the specific order or hierarchy of steps in the methods disclosed are instances of example approaches. Based upon design preferences, it is understood that the specific order or hierarchy of steps in the method can be rearranged while remaining within the disclosed subject matter. The accompanying method claims present elements of the various steps in a sample order, and are not necessarily meant to be limited to the specific order or hierarchy presented.

The described disclosure may be provided as a computer program product, or software, that may include a non-transitory machine-readable medium having stored thereon instructions, which may be used to program a computer system (or other electronic devices) to perform a process according to the present disclosure. A machine-readable medium includes any mechanism for storing information in a form (e.g., software, processing application) readable by a machine (e.g., a computer). The machine-readable medium may include, but is not limited to, magnetic storage medium (e.g., floppy diskette), optical storage medium (e.g., CD-ROM); magneto-optical storage medium, read only memory (ROM); random access memory (RAM); erasable programmable memory (e.g., EPROM and EEPROM); flash memory; or other types of medium suitable for storing electronic instructions.

The description above includes example systems, methods, techniques, instruction sequences, and/or computer program products that embody techniques of the present disclosure. However, it is understood that the described disclosure may be practiced without these specific details.

Although various representative implementations have been described above with a certain degree of particularity, those skilled in the art could make numerous alterations to the disclosed embodiments without departing from the spirit or scope of the inventive subject matter set forth in the specification. All directional references (e.g., distal, proximal, front, back, side, top, bottom, fore, aft, right, left, etc.) are only used for identification purposes to aid the reader's understanding of the implementations, and do not create limitations, particularly as to the position, orientation, or use of the invention unless specifically set forth in the claims. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other.

It is believed that the present disclosure and many of its attendant advantages will be understood by the foregoing description, and it will be apparent that various changes may be made in the form, construction and arrangement of the components without departing from the disclosed subject matter or without sacrificing all of its material advantages. The form described is merely explanatory, and it is the intention of the following claims to encompass and include such changes.

While the present disclosure has been described with reference to various embodiments, it will be understood that these embodiments are illustrative and that the scope of the disclosure is not limited to them. Many variations, modifications, additions, and improvements are possible. More generally, embodiments in accordance with the present disclosure have been described in the context of particular implementations. Functionality may be separated or combined in blocks differently in various embodiments of the disclosure or described with different terminology. These and other variations, modifications, additions, and improvements may fall within the scope of the disclosure as defined in the claims that follow.

What is claimed is:

1. A surgical table for supporting a patient over a floor, the table comprising:
   a base assembly supported on the floor and comprising a first end comprising a first base plate including a first pair of spaced apart supports, a second end opposite the first end and comprising a second base plate including a second pair of spaced apart supports, wherein the first pair and second pair of spaced apart supports comprise wheels, and a single track member extending along a base longitudinal axis between the first and second ends, the first and second base plates extending transversely to the base longitudinal axis of the track member so as to define an I-beam shape for the base assembly;
   a support column assembly moveably coupled with the base assembly and configured to translate between the first and second ends of the base assembly along the track member extending therebetween, the support column assembly being the only support column assembly coupled with the base assembly; and
   a patient support structure comprising a first end, a second end opposite the first end, and a longitudinal axis extending between the first and second ends, the second end of the patient support structure supported off of the support column assembly in a cantilevered fashion, the patient support structure having a first width substantially wider than a second width of the track member.

2. The surgical table of claim 1, wherein the support column assembly is rotationally coupled with the base assembly about a vertical pivot axis such that the support column assembly and the patient support structure are configured to pivot about the vertical pivot axis.

3. The surgical table of claim 2, wherein, when pivoting about the vertical pivot axis, the longitudinal axis of the patient support structure angles relative to the base longitudinal axis.

4. The surgical table of claim 1, wherein the support column assembly comprises a lift assembly configured to raise or lower the patient support structure.

5. The surgical table of claim 4, wherein the lift assembly comprises a pair of lift assemblies operably coupled with opposite side ends of the second end of the patient support structure.

6. The surgical table of claim 5, wherein each of the pair of lift assemblies comprises a primary and a secondary elevator.

7. The surgical table of claim 6, wherein each of the primary elevators comprises an electric linear actuator, and each of the secondary elevators comprises a chain lift.

8. The surgical table of claim 1, wherein the support column assembly is configured to pivot the patient support structure about the longitudinal axis of the patient support structure.

9. The surgical table of claim 8, wherein the support column assembly comprises a pair of spaced apart lift assemblies, wherein lifting the pair of spaced apart lift assemblies to different heights pivots the patient support structure.

10. The surgical table of claim 1, wherein the support column assembly is configured to pivot the patient support structure about an angulation axis so as to increase or decrease an angle between the longitudinal axis of the patient support structure and the vertical pivot axis.

11. The surgical table of claim 10, wherein the support column assembly comprises an angulation assembly comprising at least one electric linear actuator configured to cause the patient support structure to pivot about the angulation axis.

12. The surgical table of claim 1, wherein the base assembly comprises a track assembly and a motor, the support column assembly is configured to translate between the first and second ends of the base assembly via the track assembly and the motor.

13. The surgical table of claim 12, wherein the support column assembly is supported on a carriage assembly that is moveably coupled with the track assembly.

14. The surgical table of claim 1, wherein the wheels comprise caster wheels.

15. The surgical table of claim 1, wherein the first width extends transversely to the longitudinal axis of the patient support structure, and the second width extends transversely to the base longitudinal axis of the track member.

16. The surgical table of claim 1, wherein the first base plate has a third width extending transversely to the base longitudinal axis of the track member, the second base plate has a fourth width extending transversely to the base longitudinal axis of the track member, each of the third width and the fourth width being substantially wider than the second width of the track member.

17. The surgical table of claim 16, wherein the track member extends along the base longitudinal axis to: a first middle line of the first base plate across the third width at the first end of the base assembly; and to a second middle line of the second base plate across the fourth width at the second end of the base assembly.

* * * * *